(12) United States Patent
Surkov et al.

(10) Patent No.: US 12,053,567 B2
(45) Date of Patent: Aug. 6, 2024

(54) METHOD AND DEVICE FOR REMOVAL OF CIRCULATING CELL FREE DNA

(71) Applicant: SANTERSUS AG, Zürich (CH)

(72) Inventors: Kirill Surkov, St. Petersburg (RU); Andrew Aswani, London (GB)

(73) Assignee: SANTERSUS AG, Zürich (CH)

( * ) Notice: Subject to any disclaimer, the term of this patent is extended or adjusted under 35 U.S.C. 154(b) by 0 days.

(21) Appl. No.: 17/971,016

(22) Filed: Oct. 21, 2022

(65) Prior Publication Data

US 2023/0201439 A1 Jun. 29, 2023

Related U.S. Application Data

(60) Provisional application No. 63/294,024, filed on Dec. 27, 2021.

(51) Int. Cl.
A61M 1/34 (2006.01)

(52) U.S. Cl.
CPC ........ A61M 1/3496 (2013.01); A61M 1/3486 (2014.02); A61M 2202/0415 (2013.01)

(58) Field of Classification Search
None
See application file for complete search history.

(56) References Cited

U.S. PATENT DOCUMENTS

| | | | |
|---|---|---|---|
| 4,824,432 A | 4/1989 | Skurkovich et al. | |
| 6,046,046 A | 4/2000 | Hassanein | |
| 6,080,404 A | 6/2000 | Branham | |
| 6,528,057 B1 | 3/2003 | Ambrus et al. | |
| 6,774,102 B1 | 8/2004 | Bell et al. | |
| 7,612,032 B2 | 11/2009 | Genkin et al. | |
| 8,388,951 B2 | 3/2013 | Genkin et al. | |
| 8,431,123 B2 | 4/2013 | Genkin et al. | |
| 8,535,663 B2 | 9/2013 | Genkin et al. | |
| 8,916,151 B2 | 12/2014 | Genkin et al. | |
| 9,128,086 B2 | 9/2015 | Bawden et al. | |
| 9,248,166 B2 | 2/2016 | Genkin et al. | |
| 9,364,601 B2 | 6/2016 | Ichim et al. | |
| 9,402,944 B2 | 8/2016 | Selden et al. | |
| 9,642,822 B2 | 5/2017 | Wagner et al. | |
| 10,639,405 B2 | 5/2020 | Kiriyama | |
| 10,746,746 B2 | 8/2020 | Eccleston et al. | |
| 2007/0092509 A1 | 4/2007 | Mittra et al. | |
| 2008/0004561 A1 | 1/2008 | Genkin et al. | |
| 2009/0117099 A1 | 5/2009 | Esmon et al. | |
| 2011/0125286 A1 | 5/2011 | Selden et al. | |
| 2012/0226258 A1 | 9/2012 | Otto et al. | |
| 2012/0301487 A1 | 11/2012 | Mittra et al. | |
| 2013/0320858 A1 | 9/2013 | Cantor | |
| 2014/0099293 A1 | 4/2014 | Mittra et al. | |
| 2017/0035955 A1 | 2/2017 | Eliaz | |
| 2018/0024141 A1 | 1/2018 | Micallef et al. | |
| 2020/0261639 A1 | 8/2020 | Surkov | |

FOREIGN PATENT DOCUMENTS

| | | |
|---|---|---|
| CN | 105319374 A | 2/2016 |
| EP | 1666055 | 6/2006 |
| EP | 2390662 A1 | 11/2011 |
| JP | 2004350502 | 12/2004 |
| RU | 2441674 | 10/2012 |
| TW | 201819922 | 6/2018 |
| WO | 2005025650 | 3/2005 |
| WO | 2007049286 | 3/2007 |
| WO | 2008047364 | 4/2008 |
| WO | 2013084002 | 6/2013 |
| WO | 2014020564 | 2/2014 |
| WO | 2017049279 | 3/2017 |
| WO | 2017068371 | 4/2017 |
| WO | 2017137495 | 8/2017 |
| WO | 2018119422 | 6/2018 |
| WO | 2019053243 | 3/2019 |
| WO | 2021038010 | 3/2021 |
| WO | 2021064463 | 4/2021 |

OTHER PUBLICATIONS

Muhlbacher, F. et al., Trans. Proc., 1999, pp. 2069-2070.*
Weissenbacher, A. et al., Trans. Int., 2019, vol. 32: pp. 586-597.*
First Office Action issued in Application No. CN 201880067725.9 mailed Feb. 27, 2023; with English Translation; 6 pages.
Tanaka et al., "Expression and purification of recombinant human histones" Methods, 2004, 33(1):3-11.
Dyer et al., "Reconstitution of Nucleosome Core Particles from Recombinant Histones and DNA" Methods Enzymol., 2003, 375:23-44.
Ross et al., "Optimization of ligand presentation for immunoadsorption using star-configured polythylene glycols" J Biomed Mater Res, 2000, 51:29-36.
International Search Report and Written Opinion mailed Apr. 18, 2023 in connection with PCT/IB2022/000665.
Office Action issued Nov. 21, 2022 in connection with U.S. Appl. No. 16/648,045.
Atamaniuk, J. et al., "Apoptotic Cell-Free DNA Promotes Inflammation in Haemodialysis Patients" Nephrol Dial Transplant (2012) vol. 27, pp. 902-905.

(Continued)

*Primary Examiner* — Michael D Burkhart

(74) *Attorney, Agent, or Firm* — Troutman Pepper Hamilton Sanders LLP

(57) ABSTRACT

The invention provides apheresis devices and their use for substantial removal of all types of cfDNA for treatment of various diseases and during perfusion of an organ and/or anatomical cavity, to limit the negative effects of circulating cfDNA during organ transplantation and thus improve the quality and survival of transplanted organs, and reduce unfavorable transplantation outcomes such as transplant dysfunction, ischemia-reperfusion injury, graft rejection, and organ failure.

22 Claims, 24 Drawing Sheets

Specification includes a Sequence Listing.

(56) References Cited

OTHER PUBLICATIONS

Brockers, K. et al., "Histone H1, the Forgotten Histone" Epigenomics (2019) vol. 11, No. 4, pp. 363-366.
Cao, H. et al., "Circulatory Mitochondrial DNA is a Pro-Inflammatory Agent in Maintenance Hemodialysis Patients" PLOS One (2014) vol. 9, No. 12, 14 pages total.
Communication (International Search Report) issued by the International Searching Authority in International Application No. PCT/EP2018/075014 dated Jan. 9, 2019, 4 pages total.
Communication (International Preliminary Report on Patentability) issued by the International Searching Authority in International Application No. PCT/EP2018/075014 dated Mar. 24, 2020, 7 pages total.
Communication (Written Opinion) issued by the International Searching Authority in International Application No. PCT/EP2018/075014 dated Jan. 9, 2019, 6 pages total.
Czamanski-Cohen, J. et al., "Increased Plasma Cell-Free DNA is Associated with Low Pregnancy Rates Among Women Undergoing IVF-Embryo Transfer" Reproductive BioMedicine Online (2013) vol. 26, pp. 36-41.
Davis, JC et al., "Recombinant Human Dnase I (rhDNase) in Patients with Lupus Nephritis" Lupus (1999) vol. 8, pp. 68-76.
Fukama, T., "Gene Therapy and Regulation" Gene Therapy and Regulation (2000) 2 pages total.
Gunjan, A. et al., "Effects of H1 Histone Variant Overexpression on Chromatin Structure" The Journal of Biological Chemistry (1999) vol. 274, No. 53, pp. 37950-37956.
Hergeth, S.P. et al., "The H1 Linker Histones: Multifunctional Proteins Beyond the Nucleosomal Core Particle" EMBO Reports (2015) vol. 16, No. 11, pp. 1439-1453.
Kumar, P. et al., "Normal and Cancerous Tissues Release Extrachromosomal Circular DNA (eccDNA) into the Circulation" Mol Cancer Res (2017) vol. 15, No. 9, pp. 1197-1205.
Kusaoi, M. et al., "Separation of Circulating MicroRNAs Using Apheresis in Patients with Systemic Lupus Erythematosus" Therapeutic Apheresis and Dialysis (2016) vol. 20, No. 4, pp. 358-353.
Lintern, K.B. et al., "Immobilisation of Lactate Oxidase and Deoxyribonuclease I for Use Within a Bio-Artificial Liver Assist Device for the Treatment of Acute Liver Failure" University College London (2013) 209 pages total.
Simakova, E.S. et al., "An Experimental Support of the Use of Immobilized Decoxyribonuclease of Type I in the Treatment of Systemic Lupus Erythematosus" Abstract of Medical Science PhD Thesis (2011) 53 pages total.
Smith, B.J. et al., "Structural Homology Between a Mammalian H1 Subfraction and Avian Erythrocyte-Specific Histone H5" FEBS Letters (1980) vol. 112, No. 1, pp. 42-44.
Su, K-Y et al., "Mutational Monitoring of EGFR T790M in cfDNA for Clinical Outcome Prediction in EGFR-Mutant Lung Adenocarcinoma" PLOS One (2018) vol. 13, No. 11, 15 pages total.
"Terman et al., ""Degardation of DNA and DNA: Anti-DNA Complexes by Extracorporeal Circulation over Nuclease Immobolized on Nylon Microspheres"" Abstract: The American Society of Nephrology (1975) 2 pages total."
Terman et al., ""Degradation of Circulating DNA by Extracorporeal Circulation over Nuclease Immobilized on Nylon Microcapsules" The Journal of Clinical Investigation (1976) vol. 57, pp. 1201-1212.".
Terrell, J. et al., "Enrichment of Circulating Tumor DNA from Cell-Free DNA of Hematopoietic Origin" Journal of Clinical Oncology (2020) vol. 38, Issue 15, supplement, 3 pages total.
Trofimenko, A.S. et al., "Extracorporal Correction of Deteriorations of Catabolism of Nucleoproteins in a Model of Systemic Lupus Erythematosus. Efficiency and Safety Assessment in the Acute Experiment" Biomedical Chemistry (2015) vol. 61, pp. 622-627.
Tullis, R.H. et al., "Affinity Hemodialysis for Antiviral Therapy with Specific Application to HIV" Journal of Theoretical Medicine (2002) vol. 4, No. 3, pp. 157-166.

Wang, Z. et al., "Water-Soluble Adsorbent [beta]-cyclodextrin-grafted Polyethyleneimine for Removing Bilirubin from Plasma" Transfusion and Apheresis Science (2012) vol. 47, No. 2, pp. 159-165.
Yasuda, T. et al., "Abrupt Pubertal Elevation of Dnase I Gene Expression in Human Pituary Gland of Both Sexes" FEBS Letters (2002) vol. 510, pp. 22-26.
Zachariah, R. et al., "Circulating Cell-Free DNA as a Potential Biomarker for Minimal and Mild Endometriosis" Reproductive Biomedicine Online (2009) vol. 18, No. 3, pp. 407-411.
Communication (pursuant to Article 94(3) EPC) issued by the European Patent Office in European Application No. 18773736.6 dated Mar. 9, 2021, 4 pages total.
Office Action issued Sep. 13, 2021 in connection with Japanese Patent Application No. 2020-537046.
Office Action issued Dec. 2, 2021 in connection with Russian Application No. 2020113528.
G. Tokareva Issledovanye fetalnoy i materinskoy vnekletochnoy DNK pri normalnoy beremennosti i narusheniyakh razvitiay ploda. Abstract of the thesis. Tomsk, 2006, p. 19.
European Search Report issued Feb. 15, 2022 in connection with EP Application No. 21209617.
Atkinson A. et al., "Precipitation of nucleic acids with polyethyleneimine and the chromatography of nucleic acids and proteins on immobilised polyethyleeneimine", Biochimica Et Biophysica ACTA, Amsterdam, NL, vol. 308, No. 1, Apr. 21, 1973, pp. 41-52.
Lee J. et al., "Nucleic acid-binding polypers as anti-inflammatory agents", Proceedings of the National Academy of Sciences, vol. 108, No. 34, Aug. 23, 2011, pp. 14055-14060.
Office Action issued Mar. 15, 2022 in connection with Russian Application No. 2020113528.
Marleau A.M. et al., "Exosome removal as a therapeutic adjuvant in cancer", Journal of Translational Medicine, 2012, 10: 134, pp. 1-12.
International Search Report and Written Opinion mailed Jan. 19, 2021 in connection with International Application No. PCT/IB2020/000817.
Lau P. P. et al., "A Rapid Method for the Purification of Supercoiled PM2 DNA by Affinity Chromatography on H1 Histone Covalently Coupled to Agarose", Biochimica et Biophysica Acta, 563 (1979) pp. 313-319.
Yu S. et al., "Chromatography of Different Forms of DNA on Immobilized Histone Columns", Biochimica et Biophysica Acta, 517 (1978) pp. 31-42.
International Preliminary Report on Patentability issued Apr. 14, 2022 in connection with PCT Application No. PCT/IB2020/000817.
European Search Report issued May 10, 2022 in connection with EP Application No. 21209611.9.
Licht et al., "Plasma levels of nucleosomes and nucleosome-autoantibody complexes in murine lupus: Effects of disease progression and lipopolysaccharide administration", Athritis and Rheumatism, vol. 44, No. 6, Jun. 1, 2001, pp. 1320-1330.
Bauden et al., "Cirulating nucleosome as epigenic biomarkers in pancreatic cancer", Clinical Epigentics, Biomed Central Ltd., London, UK, vol. 7, No. 1, Oct. 7, 2015, p. 106.
International Search Report and Written Opinion mailed Sep. 19, 2022 in connection with PCT/IB2022/000192.
Thalin Charlotte et al., "Quantification of citrullinated histones: Development of an improved assay to reliability quantify nucleosomal H3Cit in human plasma" Journal of Thrombosis and Haemostasis, vol. 18, No. 10, Aug. 8, 2020, pp. 2732-2743.
Tsourouktsoglou Theodora-Dorita et al., "Histones, DNA, and Citrullination Promote Neutrophil Extracellular Trap Inflammation by Regulating the Localization and Activation of TLR4", Cell Reports, vol. 31, No. 5, May 1, 2020, pp. 107602.
Office Action issued Feb. 23, 2023 in connection with U.S. Appl. No. 16/648,045.
Lui et al. "Predominant Hematopoietic Origin of Cell-freeDNA in Plasma and Serum after Sex-mismatchedBone Marrow Transplantation", Clin Chem. 48(3):421-7, 2002.
Moss et al. "Comprehensive human cell-type methylation atlasreveals origins of circulating cell-free DNA in healthand disease", Nature Communications vol. 9, 5068, 2018.

(56) References Cited

OTHER PUBLICATIONS

Laurent et al. "Absolute measurement of the tissue originsof cell-free DNA in the healthy state andfollowing paracetamol overdose", BMC Medical Genomics vol. 13, 60, 2020.
Sun et al. "Plasma DNA tissue mapping by genome-widemethylation sequencing for noninvasive prenatal,cancer, and transplantation assessments", PNAS, vol. 112, No. 40, 2015.
Camprubí-Rimblas et al. "Anticoagulant therapy in acute respiratory distress syndrome", Ann Transl Med. 6(2): 36, 2018.
Noda et al. "Impact of Heparin on EndothelialGlycocalyx in Lung Grafts during ExVivo Lung Perfusion", J Heart Lung Transplantation, 2021; 40: S344-345, Abstract.

* cited by examiner

↑ - blood flow directions

A - A 1, 10 – cap
2, 9 – cover
3, 8 – sealing ring
4, 7 – filter
5 – housing*
6 – threaded ring

* Threaded ring is glued to the housing with cyanoacrylate glue.

EVLP Base　　　　4h EVLP + NucleoCapture

SEQUENCE LISTING

Sequence total quantity: 16
SEQ ID NO: 1          moltype = AA  length = 222
FEATURE               Location/Qualifiers
REGION                1..222
                      note = Description of Sequence:human histone H1.3
source                1..222
                      mol_type = protein
                      organism = Homo sapiens
SEQUENCE: 1
MMSETAPLAP TIPAPAEKTP VKKKAKKAGA TAGKRKASGP PVSELITKAV AASKERSGVS    60
LAALKKALAA AGYDVEKNNS RIKLGLKSLV SKGTLVQTKG TGASGSFKLN KKAASGEGKP   120
KAKKAGAAKP RKPAGAAKKP KKVAGAATPK KSIKKTPKKV KKPATAAGTK KVAKSAKKVK   180
TPQPKKAAKS PAKAKAPKPK AAKPKSGPK VTKAKKAAPK KK                        222

SEQ ID NO: 2          moltype = AA  length = 193
FEATURE               Location/Qualifiers

```
REGION                          1..193
                                note = Description of Sequence: human histone H1.0
source                          1..193
                                mol_type = protein
                                organism = Homo sapiens
SEQUENCE: 2
TENSTSAPAA KPKRAKASKK STDHPKYSDM IVAAIQAEKN RAGSSRQSIQ KYIKSHYKVG   60
ENADSQIKLS IKRLVTTGVL KQTKGVGASG SFRLAKSDEP KKSVAFKKTK KEIKKVATPK  120
KASKPKKAAS KAPTKKPKAT PVKKAKKKLA ATPKKAKKPK TVKAKPVKAS KPKKAKPVKP  180
KAKSSAKRAG KKK                                                    193

SEQ ID NO: 3                    moltype = AA   length = 193
FEATURE                         Location/Qualifiers
REGION                          1..193
                                note = Description of Sequence: Anser anser histone H5
source                          1..193
                                mol_type = protein
                                organism = Anser anser
SEQUENCE: 3
TDSPIPAPAP AAKPKRARAP RKPASHPTYS EMIAAAIRAD KSRGGSSRQS IQKYVKSHYK   60
VGGQHADLQIK LAIRRLLTTG VLKQTKGVGA SGSFRLAKGD KAKRSPAGRK KKKAARKST  120
SPKKAARPRK ARSPAKKPKA AARKARKKSR ASPKKAKKPK TVKAKSLKTS KPKKARRSKP  180
RAKSGARKSP KKK                                                    193

SEQ ID NO: 4                    moltype = AA   length = 190
FEATURE                         Location/Qualifiers
REGION                          1..190
                                note = Description of Sequence: Gallus gallus histone H5
source                          1..190
                                mol_type = protein
                                organism = Gallus gallus
SEQUENCE: 4
MTESLVLSPA PAKPKRVKAS RRSASHPTYS EMIAAAIRAE KSRGGSSRQS IQKYIKSHYK   60
VGHNADLQIK LSIRRLLAAG VLKQTKGVGA SGSFRLAKSD KAKRSPGKKK KAVRRSTSPK  120
KAARPRKARS PAKKPKATAR KARKKSRASP KKAKKPKTVK AKSRKASKAK KVKRSKPRAK  180
SGARKSPKKK                                                        190

SEQ ID NO: 5                    moltype = AA   length = 194
FEATURE                         Location/Qualifiers
REGION                          1..194
                                note = Description of Sequence: human histone H1.0
source                          1..194
                                mol_type = protein
                                organism = Homo sapiens
SEQUENCE: 5
MTENSTSAPA AKPKRAKASK KSTDHPKYSD MIVAAIQAEK NRAGSSRQSI QKYIKSHYKV   60
GENADSQIKL SIKRLVTTGV LKQTKGVGAS GSFRLAKSDE PKKSVAFKKT KKEIKKVATP  120
KKASKPKKAA SKAPTKKPKA TPVKKAKKKL AATPKKAKKP KTVKAKPVKA SKPKKAKPVK  180
PKAKSSAKRA GKKK                                                   194

SEQ ID NO: 6                    moltype = AA   length = 215
FEATURE                         Location/Qualifiers
REGION                          1..215
                                note = Description of Sequence: human histone H1.1
source                          1..215
                                mol_type = protein
                                organism = Homo sapiens
SEQUENCE: 6
MSETVPPAPA ASAAPEKPLA GKKAKKPAKA AAASKKKPAG PSVSELIVQA ASSSKERGGV   60
SLAALKKALA AAGYDVEKNN SRIKLGIKSL VSKGTLVQTK GTGASGSFKL NKKASSVETK  120
PGASKVATKT KATGASKKLK KATGASKKSV KTPKKAKKPA ATRKSSKNPK KPKTVKPKKV  180
AKSPAKAKAV KPKAAKARVT KPKTAKPKKA APKKK                            215

SEQ ID NO: 7                    moltype = AA   length = 213
FEATURE                         Location/Qualifiers
REGION                          1..213
                                note = Description of Sequence: human histone H1.2
source                          1..213
                                mol_type = protein
                                organism = Homo sapiens
SEQUENCE: 7
MSETAPAAPA AAPPAEKAPV KKKAAKKAGG TPRKASGPPV SELITKAVAA SKERSGVSLA   60
ALKKALAAAG YDVEKNNSRI KLGLKSLVSK GTLVQTKGTG ASGSFKLNKK AASGEAKPKV  120
KKAGGTKPKK PVGAAKKPKK AAGGATPKKS AKKTPKKAKK PAAATVTKKV AKSPKKAKVA  180
KPKKAAKSAA KAVKPKAAKP KVVKPKKAAP KKK                               213

SEQ ID NO: 8                    moltype = AA   length = 219
FEATURE                         Location/Qualifiers
REGION                          1..219
```

```
                            note = Description of Sequence: human histone H1.4
source                      1..219
                            mol_type = protein
                            organism = Homo sapiens
SEQUENCE: 8
MSETAPAAPA APAPAEKTPV KKKARKSAGA AKRKASGPPV SELITKAVAA SKERSGVSLA    60
ALKKALAAAG YDVEKNNSRI KLGLKSLVSK GTLVQTKGTG ASGSFKLNKK AASGEAKPKA   120
KKAGAAKAKK PAGAAKKPKK ATGAATPKKS AKKTPKKAKK PAAAAGAKKA KSPKKAKAAK   180
PKKAPKSPAK AKAVKPKAAK PKTAKPKAAK PKKAAAKKK                          219

SEQ ID NO: 9                moltype = AA   length = 226
FEATURE                     Location/Qualifiers
REGION                      1..226
                            note = Description of Sequence: human histone H1.5
source                      1..226
                            mol_type = protein
                            organism = Homo sapiens
SEQUENCE: 9
MSETAPAETA TPAPVEKSPA KKKATKKAAG AGAAKRKATG PPVSELITKA VAASKERNGL    60
SLAALKKALA AGGYDVEKNN SRIKLGLKSL VSKGTLVQTK GTGASGSFKL NKKAASGEAK   120
PKAKKAGAAK AKKPAGATPK KAKKAAGAKK AVKKTPKKAK KPAAAGVKKV AKSPKKAAA    180
AKPKKATKSP AKPKAVKPKA AKPKAAKPKA AKPKAAKAKK AAAKKK                  226

SEQ ID NO: 10               moltype = AA   length = 207
FEATURE                     Location/Qualifiers
REGION                      1..207
                            note = Description of Sequence: human histone H1.7
source                      1..207
                            mol_type = protein
                            organism = Homo sapiens
SEQUENCE: 10
MSETVPAASA SAGVAAMEKL PTKKRGRKPA GLISASRKVP NLSVSKLITE ALSVSQERVG    60
MSLVALKKAL AAAGYDVEKN NSRIKLSLKS LVNKGILVQT RGTGASGSFK LSKKVIPKST   120
RSKAKKSVSA KTKKLVLSRD SKSPKTAKTN KRAKKPRATT PKTVRSGRKA KGAKGKQQQK   180
SPVKARASKS KLTQHHEVNV RKATSKK                                       207

SEQ ID NO: 11               moltype = AA   length = 193
FEATURE                     Location/Qualifiers
REGION                      1..193
                            note = Description of Sequence: recombinant H1.0 histone
source                      1..193
                            mol_type = protein
                            organism = synthetic construct
SEQUENCE: 11
TENSTSAPAA KPKRAKASKK STDHPKYSDM IVAAIQAEKN RAGSSRQSIQ KYIKSHYKVG    60
ENADSQIKLS IKRLVTTGVL KQTKGVGASG SFRLAKSDEP KKSVAFKKTK KEIKKVATPK   120
KASKPKKAAS KAPTKKPKAT PVKKAKKKLA ATPKKAKKPK TVKAKPVKAS KPKKAKPVKP   180
KAKSSAKRAG KKK                                                      193

SEQ ID NO: 12               moltype = AA   length = 207
FEATURE                     Location/Qualifiers
REGION                      1..207
                            note = Description of Sequence: recombinant histone H1.X of
                                Caenorhabditis elegans
source                      1..207
                            mol_type = protein
                            organism = synthetic construct
SEQUENCE: 12
MSETVPAASA SAGVAAMEKL PTKKRGRKPA GLISASRKVP NLSVSKLITE ALSVSQERVG    60
MSLVALKKAL AAAGYDVEKN NSRIKLSLKS LVNKGILVQT RGTGASGSFK LSKKVIPKST   120
RSKAKKSVSA KTKKLVLSRD SKSPKTAKTN KRAKKPRATT PKTVRSGRKA KGAKGKQQQK   180
SPVKARASKS KLTQHHEVNV RKATSKK                                       207

SEQ ID NO: 13               moltype = AA   length = 218
FEATURE                     Location/Qualifiers
REGION                      1..218
                            note = Description of Sequence: recombinant human histone
                                H1.4 (HIST1H1E)
source                      1..218
                            mol_type = protein
                            organism = synthetic construct
SEQUENCE: 13
SETAPAAPAA PAPAEKTPVK KKARKSAGAA KRKASGPPVS ELITKAVAAS KERSGVSLAA    60
LKKALAAAGY DVEKNNSRIK LGLKSLVSKG TLVQTKGTGA SGSFKLNKKA ASGEAKPKAK   120
KAGAAKAKKP AGAAKKPKKA TGAATPKKSA KKTPKKAKKP AAAAGAKKAK SPKKAKAAKP   180
KKAPKSPAKA KAVKPKAAKP KTAKPKAAKP KKAAAKKK                           218

SEQ ID NO: 14               moltype = DNA   length = 19
FEATURE                     Location/Qualifiers
```

```
misc_feature           1..19
                       note = Description of sequence: bacterial 16S rDNA forward
                       primer
source                 1..19
                       mol_type = other DNA
                       organism = synthetic construct
SEQUENCE: 14
tcctacggga ggcagcagt                                                     19

SEQ ID NO: 15          moltype = DNA  length = 26
FEATURE                Location/Qualifiers
misc_feature           1..26
                       note = Description of sequence: bacterial 16S rDNA reverse
                       primer
source                 1..26
                       mol_type = other DNA
                       organism = synthetic construct
SEQUENCE: 15
ggactaccag ggtatctaat cctgtt                                             26

SEQ ID NO: 16          moltype = DNA  length = 23
FEATURE                Location/Qualifiers
misc_feature           1..23
                       note = Description of sequence: bacterial 16S rDNA probe
source                 1..23
                       mol_type = other DNA
                       organism = synthetic construct
modified_base          1
                       mod_base = OTHER
                       note = Modified base: 6-Carboxyfluorescein
modified_base          23
                       mod_base = OTHER
                       note = Modified base: Carboxytetramethylrhodamine
SEQUENCE: 16
cgtattaccg cggctgctgg cac                                                23
```

METHOD AND DEVICE FOR REMOVAL OF CIRCULATING CELL FREE DNA

CROSS-REFERENCE TO RELATED APPLICATION

This application claims priority from U.S. Provisional Patent Application No. 63/294,024, filed Dec. 27, 2021, the disclosure of which is herein incorporated by reference in its entirety.

SEQUENCE LISTING

A Sequence Listing conforming to the rules of WIPO Standard ST.26 is hereby incorporated by reference. The Sequence Listing has been filed as an electronic document via EFS-Web in ASCII format. The electronic document, created on Dec. 8, 2022, is entitled "252176000045.xml", and is 25,236 bytes in size.

FIELD OF THE INVENTION

The invention provides devices (e.g., apheresis devices) and their use for the substantial removal of all types of cell free DNA (cfDNA), including nucleosome-bound cfDNA, exosome-bound cfDNA and unbound cfDNA (including double stranded DNA [dsDNA], single stranded DNA [ssDNA] and oligonucleotides) for treatment of various diseases and during perfusion of an organ and/or anatomical cavity, to limit the negative effects of circulating cfDNA during organ transplantation and thus improve the quality and survival of transplanted organs, and reduce unfavorable transplantation outcomes such as transplant dysfunction, ischemia-reperfusion injury), graft rejection, and organ failure.

BACKGROUND OF THE INVENTION

Circulating extracellular DNA (eDNA), also called cell free DNA (cfDNA), is present in small amounts in the blood and other bodily fluids of healthy individuals.

Increased levels of circulating cfDNA are now a widely accepted marker for a number of diseases and pathological conditions including but not limited to cancer, metastatic cancer, acute organ failure, organ infarction (including myocardial infarction and ischemic stroke), hemorrhagic stroke, autoimmune disorders, graft-versus-host-disease (GVHD), graft rejection, sepsis, systemic inflammatory response syndrome (SIRS), multiple organ dysfunction syndrome (MODS), traumatic injury, proinflammatory status in aged individuals, diabetes, atherosclerosis, neurodegenerative disease, eclampsia, infertility, coagulation disorders, pregnancy-associated complications and infection. Different subtypes of circulating cfDNA might play a significant role in the progression of certain diseases and pathological conditions.

The systemic administration of a deoxyribonuclease (DNase) enzyme, which hydrolyzes circulating cfDNA for treatment of infertility, cardiovascular disorders, cancer, sepsis, graft-versus-host-disease (GVHD), organ failure, diabetes, atherosclerosis, and delayed-type hypersensitivity reactions, was proposed. See, e.g., U.S. Pat. Nos. 8,916,151; 9,642,822; 9,248,166; 8,535,663; 7,612,032; 8,388,951; 8,431,123.

However, contrary to early-stage animal models, data in real-world clinical settings has shown that the systemic application of DNase enzyme has limited effects on reducing the quantity of circulating cfDNA. For example, Hazout (Int. Pat. Appl. Pub. WO2014/020564 and U.S. Pat. Appl. Pub. No. 2015/246103) has described 10 women with high levels of circulating cfDNA (>80 ng/μl) treated with 0.1 mg/kg of DNase I daily via intramuscular route twice a day for seven days and observed only an average 26% decrease in the level of circulating cfDNA. These observations were in line with Davis et al., who failed to demonstrate the reduction of circulating level of alpha DS DNA in lupus nephritis patients receiving a 25 μg/kg dose of human recombinant DNase as a total of one intravenous and ten subcutaneous injections over a period of 19 days despite achievement in plasma of catalytically effective DNase concentrations between 40-100 ng/ml (Davis J. C. et al., Recombinant human DNase I (rhDNase) in patients with lupus nephritis Lupus (1999) Vol 8 (1), pp. 68-76).

The most abundant type of circulating cfDNA is represented by nucleosome-bound DNA. A nucleosome is a subunit of nuclear chromatin and consists of a central core protein formed by an octamer of the double-represented core histones and about 147 base pairs of double-stranded DNA (Oudet P, Gross-Bellard M, Chambon P. Electron microscopic and biochemical evidence that chromatin structure is a repeating unit. Cell. 1975; 4:281-300). Nucleosome-bound cfDNA might circulate in blood as mononucleosomes or higher order structures such as oligonucleosomes or even fragments of chromatin containing over $50\text{-}100 \times 10^3$ base pairs of DNA. This particular type of circulating cfDNA originates from cells undergoing necrosis or apoptosis. Another source of circulating cfDNA is neutrophil NETosis. Neutrophil extracellular traps (NETs), which are extracellular strands of decondensed DNA expelled from activated neutrophils, have over $15 \times 10^3$ base pairs of DNA length that are organized in 3D net structures of 10-30 nm. NETosis originating cfDNA might be either particle free or particle bound. NETs also contain highly cytotoxic enzymes and cytotoxic proteins originating from the neutrophil interior space (Sorensen, O. E. and Borregaard, N., Neutrophil extracellular traps—the dark side of neutrophils. J. Clin. Invest. 2016 May 2; 126(5): 1612-20). It has been shown recently that not only neutrophils but also macrophages might produce NET-like structures (Nat Med., 2018, 24(2): 232-238). NETs and their metabolites may trigger thrombosis, endothelial, and tissue damage associated with activation of multiple immune pathways leading to cytokine release and a systemic inflammatory response.

Another important type of circulating particle bound cfDNA is exosome-bound DNA. Exosomes are small membrane vesicles (30-100 nm) of exocytotic origin secreted by most cell types that might contain single-stranded DNA (ssDNA), mitochondrial DNA (mtDNA) and double-stranded (dsDNA) of $2.5\text{-}10 \times 10^3$ base pairs at the inner or outer space of exosome (Thakur, B. K. et al., Double-stranded DNA in exosomes: a novel biomarker in cancer detection, Cell Research (2014) 24:766-769).

A significant part of circulating cfDNA that is truly free of particles is represented by linear and circular dsDNA and ssDNA secreted by cancer cells, activated immune cells and certain other cell types. This type of cfDNA is generally 250-1000 base pairs length or higher and may be enriched in unique genome sequences (Kumar, P. et al., Normal and cancerous tissues release extrachromosomal circular DNA (eccDNA) into the circulation, Mol. Cancer. Res., Jun. 20, 2017 DOI: 10.1158/1541-7786.MCR-17-0095). Another important constituent of circulating cfDNA free of particles is mitochondrial DNA (mtDNA) of different lengths.

Another recently discovered type of particle-free circulating cfDNA is represented by ultra-short double stranded DNA (dsDNA) oligonucleotides and single stranded DNA (ssDNA) oligonucleotides with a subnucleosomal length (i.e., usually less than ~147 base pairs). It was shown that this particular cfDNA is enriched in mitochondrial DNA (mtDNA), DNA of microbial origin and mutated human genome sequences (Burnham P., Single-stranded DNA library preparation uncovers the origin and diversity of ultrashort cell-free DNA in plasma, Scientific Reports 6, Article number: 27859 (2016), doi:10.1038/srep27859). Importantly, this type of circulating cfDNA also contains the low molecular weight DNA fragments which are similar of those that appear following degradation of particle bound DNA by DNase I enzyme in blood of patients.

Several attempts have been made to use extracorporeal removal technologies to purify patient blood by removing certain constituents of the circulating cfDNA pool. See, e.g., U.S. Pat. No. 9,364,601; U.S. Patent Application Publication No. 2007/0092509; Kusaoi et al., Ther. Apher. Dial, 2016, 20:348-353.

However, there remains a need for new methods of treating diseases associated with high circulating levels of cfDNA and for devices to realize such methods.

SUMMARY OF THE INVENTION

As specified in the Background section, above, there is a need for new methods of treating diseases associated with high levels of circulating cfDNA and for devices to realize such methods. The present invention addresses this and other needs by providing devices and associated processes.

In one aspect, the invention provides a device configured to perform apheresis of an organ perfusion solution comprising one or more affinity matrixes, wherein said one or more affinity matrices are capable of capturing one or more cell free DNA (cfDNA) selected from nucleosome-bound cfDNA, exosome-bound cfDNA, and unbound cfDNA from the organ perfusion solution, wherein said organ is perfused extracorporeally or in an anatomical cavity, and wherein at least one of said one or more affinity matrices comprises a DNA binding polymer, a DNA binding protein, an anti-histone antibody, an anti-nucleosome antibody, a DNA intercalating agent, an anti-DNA antibody, a lectin, or any combination thereof.

In some embodiments, said device is integrated into extracorporeal organ perfusion circuit.

In some embodiments, the unbound cfDNA comprises double stranded DNA (dsDNA), single stranded DNA (ssDNA) and oligonucleotides.

In some embodiments, at least one of said one or more affinity matrices comprises a DNA binding protein. In one embodiment, the DNA binding protein is a histone (e.g., a linker histone selected, without limitation, from an H1.0 linker histone, an H1.1 linker histone, an H1.2 linker histone, an H1.3 linker histone, an H1.4 linker histone, an H1.5 linker histone, and H1.7 linker histone). In one embodiment, the linker histone comprises an amino acid sequence which is at least 70% identical to the sequence selected from:

(SEQ ID NO: 1)
MMSETAPLAPTIPAPAEKTPVKKKAKKAGATAGKRKASGPPVSELITK

AVAASKERSGVSLAALKKALAAAGYDVEKNNSRIKLGLKSLVSKGTLV

QTKGTGASGSFKLNKKAASGEGKPKAKKAGAAKPRKPAGAAKKPKKVA

GAATPKKSIKKTPKKVKKPATAAGTKKVAKSAKKVKTPQPKKAAKSPA

KAKAPKPKAAKPKSGKPKVTKAKKAAPKKK;

(SEQ ID NO: 2)
TENSTSAPAAKPKRAKASKKSTDHPKYSDMIVAAIQAEKNRAGSSRQS

IQKYIKSHYKVGENADSQIKLSIKRLVTTGVLKQTKGVGASGSFRLAK

SDEPKKSVAFKKTKKEIKKVATPKKASKPKKAASKAPTKKPKATPVKK

AKKKLAATPKKAKKPKTVKAKPVKASKPKKAKPVKPKAKSSAKRAGKK

K;

(SEQ ID NO: 3)
TDSPIPAPAPAAKPKRARAPRKPASHPTYSEMIAAAIRADKSRGGSSR

QSIQKYVKSHYKVGQHADLQIKLAIRRLLTTGVLKQTKGVGASGSFRL

AKGDKAKRSPAGRKKKKAARKSTSPKKAARPRKARSPAKKPKAAARK

ARKKSRASPKKAKKPKTVKAKSLKTSKPKKARRSKPRAKSGARKSPKK

K;
and (SEQ ID NO: 4)
MTESLVLSPAPAKPKRVKASRRSASHPTYSEMIAAAIRAEKSRGGSSR

QSIQKYIKSHYKVGHNADLQIKLSIRRLLAAGVLKQTKGVGASGSFRL

AKSDKAKRSPGKKKKAVRRSTSPKKAARPRKARSPAKKPKATARKARK

KSRASPKKAKKPKTVKAKSRKASKAKKVKRSKPRAKSGARKSPKKK.

In one embodiment, the DNA binding protein is a high mobility group (HMG) protein.

In some embodiments, the DNA binding polymer is a DNA binding polysaccharide. Non-limiting examples of useful DNA binding polysaccharides include, e.g., 2S,3S,4R,5R,6R)-6-{[(2S,3S,4S,5R,6S)-6-{[(2R,3S,4S,5R)-2-carboxy-4,6-dihydroxy-5-(sulfooxy)oxan-3-yl]oxy}-2-hydroxy-4-(sulfomethyl)-5-(sulfooxy)oxan-3-yl]oxy}-3-{[(2R,3R,4R,5S,6R)-3-acetamido-4,5-dihydroxy-6-[(sulfooxy)methyl]oxan-2-yl]oxy}-4,5-dihydroxyoxane-2-carboxylic acid, and derivatives thereof. In one embodiment, the DNA binding polysaccharide is 4-Methoxybenzaldehyde functionalized agarose.

In some embodiments, the DNA binding polymer is selected from a cationic polymer, polyamidoamine dendrimer, poly-L-lysine, polyethylenimine, and hyperbranched polyethylenimine, In some embodiments, the lectin is selected from *Galanthus nivalis* Lectin (GNA), *Narcissus Pseudonarcissus* Lectin (NPA), Conconavalin A, phytohemagglutinin, and cyanovirin.

In some embodiments, the DNA intercalating agent is polymyxin b.

In some embodiments, the device comprises two or more different affinity matrixes arranged within one device.

In some embodiments, the one or more affinity matrices contained within the device are capable of capturing substantially all of nucleosome-bound cfDNA, exosome-bound cfDNA, and unbound cfDNA from the organ perfusion solution.

In one embodiment, the one or more affinity matrices are placed in a housing comprising a hollow fiber filter disposed within said housing, said filter comprising a plurality of pores and one or more affinity matrices positioned inside the housing and outside the hollow fiber in an extra-lumen space and wherein the pores are 0.2-0.7 μm in size.

In another aspect, the invention provides a method of reducing the level of cell-free DNA (cfDNA) in a perfused organ, the method comprising: (a) performing an apheresis procedure comprising the diversion of a perfusion solution from the perfused organ into the device of the invention (as described above) to produce the perfusion solution with reduced levels of the cfDNA; and (b) returning the perfusion solution with reduced levels of cfDNA into the perfused organ, wherein the apheresis procedure reduces the level of one or more cfDNA selected from nucleosome-bound cfDNA, exosome-bound cfDNA, and unbound cfDNA in the perfusion solution.

In a further aspect, the invention provides a method of reducing an unfavorable transplantation outcome selected from transplant dysfunction, ischemia-reperfusion injury, graft rejection, and organ failure in a subject upon placement of a perfused organ transplant into said subject, the method comprising the following steps performed prior to placing the organ into the subject: (a) performing an apheresis procedure comprising the diversion of a perfusion solution from the perfused organ into the device of the invention (as described above) to produce the perfusion solution with reduced levels of the cfDNA; and (b) returning the perfusion solution with reduced levels of cfDNA into the perfused organ, wherein the apheresis procedure reduces the level of one or more cfDNA selected from nucleosome-bound cfDNA, exosome-bound cfDNA, and unbound cfDNA in the perfusion solution.

In some embodiments of any of the above methods, the unbound cfDNA comprises double stranded DNA (dsDNA), single stranded DNA (ssDNA) and oligonucleotides.

In some embodiments of any of the above methods, the perfused organ is selected from liver, lung, kidney, pancreas, and heart.

In one embodiment of any of the above methods, the perfusion solution comprises whole blood or leukodepleted blood. In another embodiment of any of the above methods, the perfusion solution comprises a mixture of an artificial perfusion solution and erythrocytes. In a further embodiment of any of the above methods, the perfusion solution comprises a cell free artificial perfusion solution.

In one embodiment of any of the above methods, the perfusion is performed ex vivo using an organ support system selected from OrganOx Metra®, Transmedics OCS™ systems, Aferetica PerLife® system, XVIVO System (XPS™), Organ Assist®, and Cleveland.

In another aspect, the invention provides a device (e.g., a device configured to perform apheresis) comprising one or more affinity matrices, wherein said one or more affinity matrices are capable of capturing one or more cell free DNA (cfDNA) selected from nucleosome-bound cfDNA, exosome-bound cfDNA, and unbound cfDNA from a bodily fluid of a subject or from an organ perfusion solution, wherein at least one of said one or more affinity matrices comprises a DNA binding protein.

In some embodiments, the unbound cfDNA comprises double stranded DNA (dsDNA), single stranded DNA (ssDNA) and oligonucleotides.

In some embodiments, the device comprises two or more affinity matrices. In some embodiments, (i) the first of the two or more affinity matrices is capable of capturing nucleosome-bound cfDNA and/or exosome-bound cfDNA and (ii) the second of the two or more affinity matrices is capable of capturing unbound cfDNA, and wherein the first and second affinity matrices are arranged within the device in any order. In some embodiments, (i) the first of the two or more affinity matrices comprises a DNA binding protein, an anti-histone antibody, an anti-nucleosome antibody, a DNA intercalating agent, a DNA binding polymer, an anti-DNA antibody, a lectin, or any combination thereof, and (ii) the second of the two or more affinity matrices comprises a DNA binding protein, a DNA intercalating agent, a DNA binding polymer, an anti-DNA antibody, or any combination thereof, and wherein the first and second affinity matrices are arranged within the device in any order.

In some embodiments, the DNA binding protein is a histone or a high mobility group (HMG) protein. In some embodiments, the histone is a linker histone (e.g., a linker histone H5 or a linker histone H1 [e.g., an H1.0 linker histone, an H1.1 linker histone, an H1.2 linker histone, an H1.3 linker histone, an H1.4 linker histone, an H1.5 linker histone, or H1.7 linker histone]). In some embodiments, the DNA binding protein is a human H1.3 linker histone. In some embodiments, the DNA binding protein is a human H1.0 linker histone. In some embodiments, the linker histone comprises an amino acid sequence which is at least 70% identical to the sequence selected from:

```
                                    (SEQ ID NO: 1)
MMSETAPLAPTIPAPAEKTPVKKKAKKAGATAGKRKASGPPVSELITK

AVAASKERSGVSLAALKKALAAAGYDVEKNNSRIKLGLKSLVSKGTLV

QTKGTGASGSFKLNKKAASGEGKPKAKKAGAAKPRKPAGAAKKPKKVA

GAATPKKSIKKTPKKVKKPATAAGTKKVAKSAKKVKTPQPKKAAKSPA

KAKAPKPKAAKPKSGKPKVTKAKKAAPKKK;

(SEQ ID NO: 2)
TENSTSAPAAKPKRAKASKKSTDHPKYSDMIVAAIQAEKNRAGSSRQS

IQKYIKSHYKVGENADSQIKLSIKRLVTTGVLKQTKGVGASGSFRLAK

SDEPKKSVAFKKTKKEIKKVATPKKASKPKKAASKAPTKKPKATPVKK

AKKKLAATPKKAKKPKTVKAKPVKASKPKKAKPVKPKAKSSAKRAGKK

K;

(SEQ ID NO: 3)
TDSPIPAPAPAAKPKRARAPRKPASHPTYSEMIAAAIRADKSRGGSSR

QSIQKYVKSHYKVGQHADLQIKLAIRRLLTTGVLKQTKGVGASGSFRL

AKGDKAKRSPAGRKKKKAARKSTSPKKAARPRKARSPAKKPKAAARK

ARKKSRASPKKAKKPKTVKAKSLKTSKPKKARRSKPRAKSGARKSPKK

K;
and (SEQ ID NO: 4)
MTESLVLSPAPAKPKRVKASRRSASHPTYSEMIAAAIRAEKSRGGSSR

QSIQKYIKSHYKVGHNADLQIKLSIRRLLAAGVLKQTKGVGASGSFRL

AKSDKAKRSPGKKKKAVRRSTSPKKAARPRKARSPAKKPKATARKARK

KSRASPKKAKKPKTVKAKSRKASKAKKVKRSKPRAKSGARKSPKKK.
```

In some embodiments, the DNA binding protein is a high mobility group (HMG) protein. In some embodiments, the HMG protein is high mobility group box protein 1 (HMGB1).

In some embodiments, the DNA binding polymer is glycosaminoglycan. In some embodiments, the glycosaminoglycan is 2S,3S,4R,5R,6R)-6-{[(2S,3S,4S,5R,6S)-6-{[(2R,3S,4S,5R)-2-carboxy-4,6-dihydroxy-5-(sulfooxy) oxan-3-yl]oxy}-2-hydroxy-4-(sulfomethyl)-5-(sulfooxy) oxan-3-yl]oxy}-3-{[(2R,3R,4R,5S,6R)-3-acetamido-4,5- dihydroxy-6-[(sulfooxy)methyl]oxan-2-yl]oxy}-4,5-dihydroxyoxane-2-carboxylic acid or a derivative thereof.

In some embodiments, the DNA binding polymer is polyamidoamine dendrimer.

In some embodiments, the DNA binding polymer is a cationic polymer. In some embodiments, the cationic polymer is a polysaccharide or a chemically modified polysaccharide.

In some embodiments, the chemically modified polysaccharide is 4-Methoxybenzaldehyde functionalized agarose. In some embodiments, the cationic polymer is poly-L-lysine or polyethylenimine. In some embodiments, the poly-L-lysine is hyper-branched poly-L-lysine. In some embodiments, the polyethylenimine is hyper-branched polyethylenimine.

In some embodiments, the DNA intercalating agent is polymyxin B (see, e.g., Kong et al., Microchim Acta, 2011, 173:207-213), Hoechst 33342 or chloroquine.

In some embodiments, the anti-histone antibody is an anti-histone H2A antibody.

In some embodiments, the lectin is *Galanthus nivalis* Lectin (GNA), *Narcissus Pseudonarcissus* Lectin (NPA), Conconavalin A, phytohemagluttanin, or cyanovirin. In some embodiments, the lectin is *Galanthus nivalis* Lectin (GNA).

In some embodiments, the two or more affinity matrices are sequentially arranged as two or more affinity columns.

In some embodiments, the two or more affinity matrices are arranged within one affinity column.

In some embodiments, the first affinity matrix in the sequence comprises a DNA binding polymer or a DNA intercalating agent. In some embodiments, the DNA binding polymer is a cationic polymer. In some embodiments, the cationic polymer is poly-L-lysine or polyethylenimine. In some embodiments, the poly-L-lysine is hyper-branched poly-L-lysine. In some embodiments, the polyethylenimine is hyper-branched polyethylenimine. In some embodiments, the cationic polymer is polyamidoamine dendrimer. In some embodiments, the DNA intercalating agent is polymyxin B, Hoechst 33342 or chloroquine.

In some embodiments, the device comprises one of the following column combinations arranged in any order:
  (a) (i) DNA intercalating agent Hoechst 33342 affinity column and (ii) anti-DNA antibody affinity column; or
  (b) (i) anti-nucleosome antibody affinity matrix (ANAM) column and (ii) anti-DNA antibody affinity column; or
  (c) (i) anti-nucleosome antibody affinity matrix (ANAM) column and (ii) polyamidoamine dendrimer affinity matrix (PDAM) column; or
  (d) (i) anti-nucleosome antibody affinity matrix (ANAM) column and (ii) hyper-branched poly-L-lysine affinity matrix (PLLAM) column; or
  (e) (i) anti-histone H2A antibody affinity column, (ii) lectin affinity column, and (iii) histone H1 affinity column or polyamidoamine dendrimer affinity matrix (PDAM) column or hyper-branched poly-L-lysine affinity matrix (PLLAM) column or DNA intercalating agent Hoechst 33342 affinity column.

In some embodiments, the device comprises a single affinity matrix. In some embodiments, the affinity matrix comprises a histone. In some embodiments, the histone is a linker histone (e.g., a linker histone H5 or a linker histone H1 [e.g., an H1.0 linker histone, an H1.1 linker histone, an H1.2 linker histone, an H1.3 linker histone, an H1.4 linker histone, an H1.5 linker histone, or H1.7 linker histone]). In some embodiments, the DNA binding protein is a human H1.3 linker histone. In some embodiments, the DNA binding protein is a human H1.0 linker histone. In some embodiments, the linker histone comprises an amino acid sequence which is at least 70% identical to the sequence selected from:

```
                                        (SEQ ID NO: 1)
MMSETAPLAPTIPAPAEKTPVKKKAKKAGATAGKRKASGPPVSELITK

AVAASKERSGVSLAALKKALAAAGYDVEKNNSRIKLGLKSLVSKGTLV

QTKGTGASGSFKLNKKAASGEGKPKAKKAGAAKPRKPAGAAKKPKKVA

GAATPKKSIKKTPKKVKKPATAAGTKKVAKSAKKVKTPQPKKAAKSPA

KAKAPKPKAAKPKSGKPKVTKAKKAAPKKK;

(SEQ ID NO: 2)
TENSTSAPAAKPKRAKASKKSTDHPKYSDMIVAAIQAEKNRAGSSRQS

IQKYIKSHYKVGENADSQIKLSIKRLVTTGVLKQTKGVGASGSFRLAK

SDEPKKSVAFKKTKKEIKKVATPKKASKPKKAASKAPTKKPKATPVKK

AKKKLAATPKKAKKPKTVKAKPVKASKPKKAKPVKPKAKSSAKRAGKK

K;

(SEQ ID NO: 3)
TDSPIPAPAPAAKPKRARAPRKPASHPTYSEMIAAAIRADKSRGGSSR

QSIQKYVKSHYKVGQHADLQIKLAIRRLLTTGVLKQTKGVGASGSFRL

AKGDKAKRSPAGRKKKKAARKSTSPKKAARPRKARSPAKKPKAAARK

ARKKSRASPKKAKKPKTVKAKSLKTSKPKKARRSKPRAKSGARKSPKK

K;
and
                                        (SEQ ID NO: 4)
MTESLVLSPAPAKPKRVKASRRSASHPTYSEMIAAAIRAEKSRGGSSR

QSIQKYIKSHYKVGHNADLQIKLSIRRLLAAGVLKQTKGVGASGSFRL

AKSDKAKRSPGKKKKAVRRSTSPKKAARPRKARSPAKKPKATARKARK

KSRASPKKAKKPKTVKAKSRKASKAKKVKRSKPRAKSGARKSPKKK.
```

In some embodiments, the affinity matrix comprises a high mobility group (HMG) protein. In some embodiments, the HMG protein is high mobility group box protein 1 (HMGB1). In some embodiments, the affinity matrix comprises a DNA binding polymer. In some embodiments, the DNA binding polymer is polyamidoamine dendrimer. In some embodiments, the DNA binding polymer is hyper-branched poly-L-lysine. In some embodiments, the affinity matrix comprises a DNA intercalating agent. In some embodiments, the DNA intercalating agent is polymyxin B, Hoechst 33342 or chloroquine. In some embodiments, the affinity matrix comprises an anti-DNA antibody.

In some embodiments of any of the above devices, the bodily fluid is selected from blood, serum, plasma, cerebrospinal fluid (CSF), endometrial fluid, urine, saliva, lymph, glymph, tear fluid, sweat, synovial fluid, and sputum.

In some embodiments of any of the above devices, the device is configured to perform apheresis.

In some embodiments of any of the above devices, one or more affinity matrices are placed in a housing comprising a hollow fiber filter disposed within said housing, said filter comprising a plurality of pores and one or more affinity matrices positioned inside the housing and outside the hollow fiber in an extra-lumen space. In some embodiments, the pores are 0.2-0.7 μm in size.

In some embodiments of any of the above devices, one or more affinity matrices are continuously perfused through a housing comprising a hollow fiber filter disposed within said housing, said filter comprising a plurality of pores and one or more affinity matrices continuously perfused inside the housing outside the hollow fiber in an extra-lumen space. In some embodiments, the pores are 0.3-0.7 µm in size. In some embodiments, alternatively or additionally to insoluble affinity matrix placed in plasma compartment, a DNA binding ligand is coupled with exterior (plasma) portion of hollow fiber membrane which is facing the extra-lumen space and thus the DNA binding ligand cannot contact blood cells.

In some embodiments of any of the above devices, the device comprises:
  a housing;
  a hollow fiber filter disposed within said housing, said filter comprising a plurality of pores sized and dimensioned to not permit passage of cells and insoluble affinity matrix capable of capturing cfDNA; and
  at least one insoluble matrix capable of capturing cfDNA and positioned inside the housing and outside the hollow fiber in an extra-lumen space.

In another aspect, the invention provides a method of reducing the level of cell free DNA (cfDNA) in a bodily fluid of a subject, the method comprising:
  (a) performing an apheresis procedure comprising the diversion of the bodily fluid from the subject into any of the above devices of to produce the bodily fluid with reduced levels of the cfDNA; and
  (b) returning the bodily fluid with reduced levels of the cfDNA to the subject, wherein the apheresis procedure reduces the level of one or more cfDNA selected from nucleosome-bound cfDNA, exosome-bound cfDNA, and unbound cfDNA in the bodily fluid of the subject.

In a further aspect, the invention provides a method of treating a disease in a subject in need thereof, the method comprising:
  (a) performing an apheresis procedure comprising the diversion of a bodily fluid from the subject into any of the above devices to produce the bodily fluid with reduced levels of the cfDNA; and
  (b) returning the bodily fluid with reduced levels of the cfDNA to the subject, wherein the apheresis procedure reduces the level of one or more cfDNA selected from nucleosome-bound cfDNA, exosome-bound cfDNA, and unbound cfDNA in the bodily of the subject.

In some embodiments of any of the above methods, the subject has a disease characterized by an elevated level of cfDNA in the bodily fluid.

In some embodiments of any of the above methods, the subject has a disease selected from a neurodegenerative disease, a cancer, a chemotherapy-related toxicity, an irradiation induced toxicity, an organ failure, an organ injury, an organ infarct, ischemia, an acute vascular event, a stroke, graft-versus-host-disease (GVHD), graft rejection, delayed graft function sepsis, COVID-19, systemic inflammatory response syndrome (SIRS), multiple organ dysfunction syndrome (MODS), a traumatic injury, aging, diabetes, atherosclerosis, an autoimmune disorder, eclampsia, infertility, a pregnancy-associated complication, a coagulation disorder, and an infection. In some embodiments of any of the above methods, the subject may develop graft-versus-host-disease (GVHD), graft rejection, delayed graft function, organ failure, organ injury, organ infarct, or multiple organ dysfunction syndrome (MODS).

In some embodiments of any of the above methods, the subject has received or is due to receive an organ transplant.

In some embodiments of any of the above methods, the subject is an organ donor. In some embodiments of any of the above methods, the subject has received or is due to receive an anti-cancer therapy.

In some embodiments of any of the above methods, the subject has received or is due to receive an immune checkpoint blockade therapy.

In a further aspect, the invention provides a method of improving efficacy and/or reducing toxicity of an immune checkpoint inhibitor therapy in a subject in need thereof, the method comprising:
  (a) performing an apheresis procedure comprising the diversion of a bodily fluid from the subject into any of the above devices to produce the bodily fluid with reduced levels of the cfDNA; and
  (b) returning the bodily fluid with reduced levels of the cfDNA to the subject, wherein the apheresis procedure reduces the level of one or more cfDNA selected from nucleosome-bound cfDNA, exosome-bound cfDNA, and unbound cfDNA in the bodily of the subject.

In some embodiments of any of the above methods, the subject has received or is due to receive an adoptive cell therapy.

In yet another aspect, the invention provides a method of improving efficacy and/or reducing toxicity of an adoptive cell therapy in a subject in need thereof, the method comprising:
  (a) performing an apheresis procedure comprising the diversion of a bodily fluid from the subject into any of the above devices to produce the bodily fluid with reduced levels of the cfDNA; and
  (b) returning the bodily fluid with reduced levels of the cfDNA to the subject, wherein the apheresis procedure reduces the level of one or more cfDNA selected from nucleosome-bound cfDNA, exosome-bound cfDNA, and unbound cfDNA in the bodily of the subject.

In some embodiments of the above two methods, the adoptive cell therapy is a chimeric antigen receptor (CAR) therapy (e.g., a CAR-T cell therapy or a CAR-NK cell therapy).

In some embodiments of any of the above methods, the subject is human.

In another aspect, the invention provides a method of reducing the level of cell-free DNA (cfDNA) in a perfused organ, the method comprising:
  (a) performing an apheresis procedure comprising the diversion of a perfusion solution from the ex vivo perfused organ into any of the above devices to produce the perfusion solution with reduced levels of the cfDNA; and
  (b) returning the perfusion solution with reduced levels of cfDNA into the ex vivo perfused organ, wherein the apheresis procedure reduces the level of one or more cfDNA selected from nucleosome-bound cfDNA, exosome-bound cfDNA, and unbound cfDNA in the perfusion solution and resulted in improved organ quality and transplantability.

In a further aspect, the invention provides a method of ameliorating a reperfusion injury in a subject upon placement of an ex vivo perfused organ into said subject, the method comprising the following steps performed prior to placing the organ into the subject:
  (a) performing an apheresis procedure comprising the diversion of a perfusion solution from the ex vivo perfused organ into any of the above devices to produce the perfusion solution with reduced levels of the cfDNA; and (b) returning the perfusion solution with reduced levels of cfDNA into the ex vivo perfused organ, wherein the apheresis procedure reduces the level of one or more cfDNA selected from nucleosome-bound cfDNA, exosome-bound cfDNA, and unbound cfDNA in the perfusion solution.

In some embodiments of the above two methods, the ex vivo perfused organ is selected from liver, lung, kidney, pancreas, and heart.

In some embodiments of the above two methods, the organ is perfused prior to recovery from an organ donor (e.g., during donation after a circulatory death).

In some embodiments of the above two methods, the perfusion solution comprises whole blood.

In some embodiments of the above two methods, the perfusion solution comprises a mixture of an artificial perfusion solution and erythrocytes.

In some embodiments of the above two methods, the ex vivo perfusion is performed using an organ support system selected from OrganOx Metra®, Transmedics OCS™ systems, Aferetica PerLife® system, XVIVO System (XPS™), Organ Assist®, and Cleveland.

In some embodiments of any of the above methods, the device comprises one or more affinity matrices, wherein said one or more affinity matrices are capable of capturing one or more cfDNA selected from nucleosome-bound cfDNA, exosome-bound cfDNA, and unbound cfDNA from a bodily fluid of the subject or from the perfusion solution, wherein at least one of said one or more affinity matrices comprises a DNA binding protein. In some embodiments, the DNA binding protein is a high mobility group (HMG) protein. In some embodiments, the HMG protein is high mobility group box protein 1 (HMGB1).

In some embodiments of any of the above methods, the device comprises one or more affinity matrices, wherein said one or more affinity matrices are capable of capturing one or more cfDNA selected from nucleosome-bound cfDNA, exosome-bound cfDNA, and unbound cfDNA from a bodily fluid of the subject or from the perfusion solution, wherein at least one of said one or more affinity matrices comprises a DNA binding antibody.

In some embodiments of any of the above methods, the device comprises one or more affinity matrices, wherein said one or more affinity matrices are capable of capturing one or more cfDNA selected from nucleosome-bound cfDNA, exosome-bound cfDNA, and unbound cfDNA from a bodily fluid of the subject or from the perfusion solution, wherein at least one of said one or more affinity matrices comprises a histone binding antibody.

In some embodiments of any of the above methods, the device comprises one or more affinity matrices, wherein said one or more affinity matrices are capable of capturing one or more cfDNA selected from nucleosome-bound cfDNA, exosome-bound cfDNA, and unbound cfDNA from a bodily fluid of the subject or from the perfusion solution, wherein at least one of said one or more affinity matrices comprises a nucleosome binding antibody.

In some embodiments of any of the above methods, the device comprises one or more affinity matrices, wherein said one or more affinity matrices are capable of capturing one or more cfDNA selected from nucleosome-bound cfDNA, exosome-bound cfDNA, and unbound cfDNA from a bodily fluid of the subject or from the perfusion solution, wherein at least one of said one or more affinity matrices comprises a DNA binding polymer. In some embodiments, the DNA binding polymer is glycosaminoglycan. In some embodiments, the glycosaminoglycan is 2S,3S,4R,5R,6R)-6-{[(2S,3S,4S,5R,65)-6-{[(2R,3S,4S,5R)-2-carboxy-4,6-dihydroxy-5-(sulfooxy)oxan-3-yl]oxy}-2-hydroxy-4-(sulfomethyl)-5-(sulfooxy)oxan-3-yl]oxy}-3-{[(2R,3R,4R,5S,6R)-3-acetamido-4,5-dihydroxy-6-[(sulfooxy)methyl]oxan-2-yl]oxy}-4,5-dihydroxyoxane-2-carboxylic acid or a derivative thereof. In some embodiments, the DNA binding polymer is polyamidoamine dendrimer. In some embodiments, the DNA binding polymer is a cationic polymer. In some embodiments, the cationic polymer is a polysaccharide or a chemically modified polysaccharide. In some embodiments, the chemically modified polysaccharide is 4-Methoxybenzaldehyde functionalized agarose. In some embodiments, the cationic polymer is poly-L-lysine or polyethylenimine. In some embodiments, the poly-L-lysine is hyper-branched poly-L-lysine. In some embodiments, the polyethylenimine is hyper-branched polyethylenimine.

In some embodiments of any of the above methods, the device comprises one or more affinity matrices, wherein said one or more affinity matrices are capable of capturing one or more cfDNA selected from nucleosome-bound cfDNA, exosome-bound cfDNA, and unbound cfDNA from a bodily fluid of a subject or from an organ perfusion solution, wherein at least one of said one or more affinity matrices comprises a DNA intercalating agent. In some embodiments, the DNA intercalating agent is polymyxin B, Hoechst 33342 or chloroquine.

In some embodiments of any of the above methods, the device comprises one or more affinity matrices, wherein said one or more affinity matrices are capable of capturing one or more cfDNA selected from nucleosome-bound cfDNA, exosome-bound cfDNA, and unbound cfDNA from a bodily fluid of the subject or from the perfusion solution, wherein at least one of said one or more affinity matrices comprises a lectin. In some embodiments, the lectin is *Galanthus nivalis* Lectin (GNA), *Narcissus Pseudonarcissus* Lectin (NPA), Conconavalin A, phytohemagluttanin, or cyanovirin.

In another aspect, the invention provides a method of reducing the level of cell free DNA (cfDNA) in an in vivo perfused anatomical cavity, the method comprising:
  (a) performing an apheresis procedure comprising the diversion of a perfusion solution from the in vivo perfused anatomical cavity into any of the above devices to produce the perfusion solution with reduced levels of cfDNA; and
  (b) returning the perfusion solution with reduced levels of the cfDNA into the in vivo perfused anatomical cavity wherein the apheresis procedure reduces the level of one or more cfDNA selected from nucleosome-bound cfDNA, exosome-bound cfDNA, and unbound cfDNA in the perfusion solution.

In some embodiments of the above method, the anatomical cavity is peritoneal cavity or thoracic cavity. In some embodiments the above method, the perfusion solution comprises hyperthermic intraperitoneal chemotherapy or hyperthermic intrathoracic chemotherapy.

In yet another aspect, the invention provides a method of capturing one or more cell free DNA (cfDNA) selected from nucleosome-bound cfDNA, exosome-bound cfDNA, and unbound cfDNA from a perfusion solution, the method comprising contacting the perfusion solution with any of the above devices.

In a further aspect, the invention provides a method of capturing one or more cell free DNA (cfDNA) selected from nucleosome-bound cell free DNA (cfDNA), exosome-bound cfDNA, and unbound cfDNA from a bodily fluid sample, the method comprising contacting the sample with any of the above devices.

In another aspect, the invention provides a method for isolating one or more cell free DNA (cfDNA) selected from nucleosome-bound cfDNA, exosome-bound cfDNA, and unbound cfDNA from a biological sample comprising cfDNA, the method comprising contacting the biological sample with a device of the invention, and then releasing the bound cfDNA from the device. In some embodiments, the method further comprises analyzing the released cfDNA. In some embodiments, the released cfDNA is analyzed quantitatively and/or qualitatively to assess the likelihood of its negative effects on quality and survival of transplanted organs, and the likelihood of unfavorable transplantation outcomes such as transplant dysfunction, ischemia-reperfusion injury, graft rejection, and organ failure. In some embodiments, the released cfDNA is analyzed to monitor a disease. In some embodiments, the method further comprises selecting a therapy for a disease. In some embodiments, the method further comprises administering a therapy to a subject which was used to derive the biological sample.

In some embodiments of the above two methods, the biological sample is a biological fluid sample. In some embodiments, the biological fluid sample is a blood sample, a serum sample, a plasma sample, a cerebrospinal fluid (CSF) sample, an endometrial fluid sample, a urine sample, a saliva sample, a lymph sample, a glymph sample, a tear fluid sample, a sweat sample, a synovial fluid sample, or a sputum sample. In some embodiments, the biological fluid sample is a blood sample, a plasma sample, or a serum sample. In some embodiments, the blood is menstrual blood. In some embodiments, the biological sample is a stool sample or a breath sample. In some embodiments, the breath sample is a condensed breath. In some embodiments, the condensed breath is an extract of condensed breath, a purification of condensed breath, or a dilution of condensed breath. In some embodiments, the biological sample is obtained from a subject. In some embodiments, releasing the cfDNA comprises contacting the complex with a protease. In some embodiments, the protease is proteinase K.

These and other aspects of the present invention will be apparent to those of ordinary skill in the art in the following description, claims and drawings.

BRIEF DESCRIPTION OF THE DRAWINGS

FIG. 2A shows tumors excised from control group mice. FIG. 2B shows tumors excised from mice treated with DNA from an NSCLC T3N2M+ patient purified from nucleosome and exosome bound circulating cfDNA.

Figure 15A:
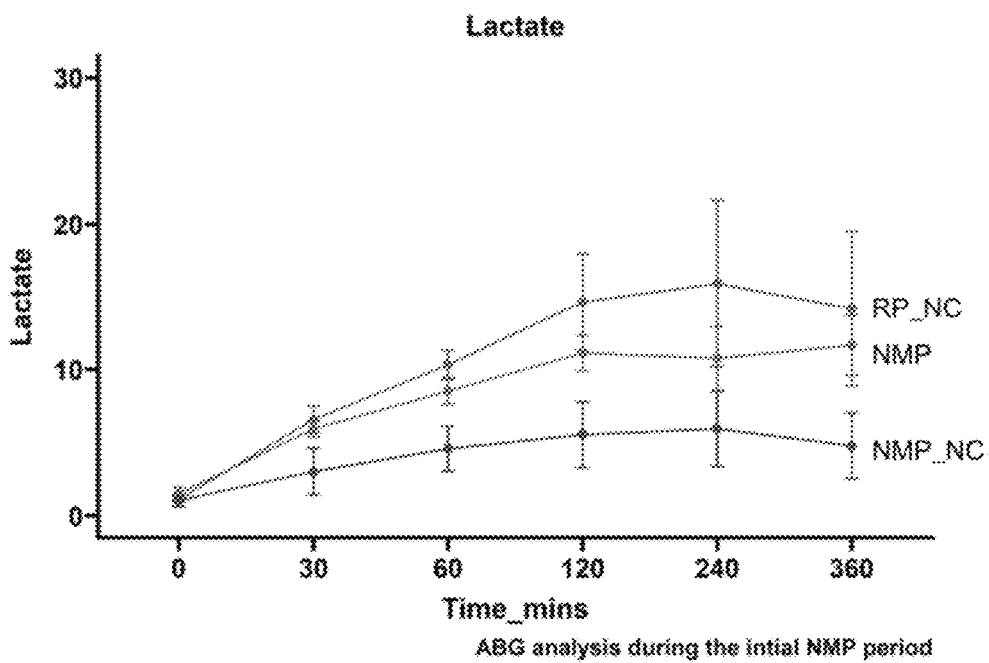
Figure 15B:
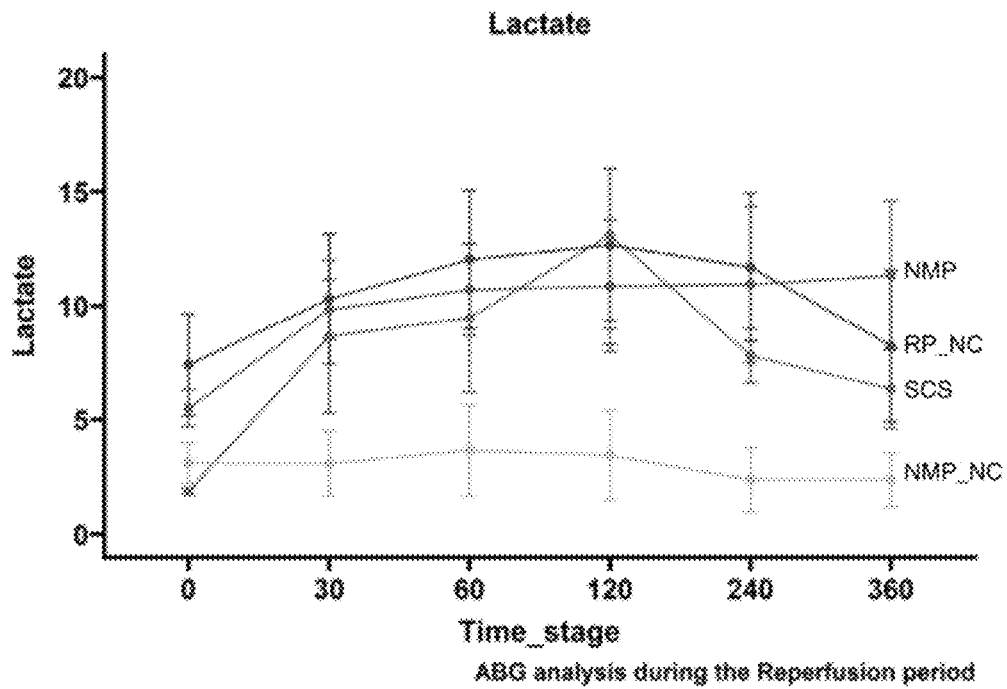
Figure 15C:
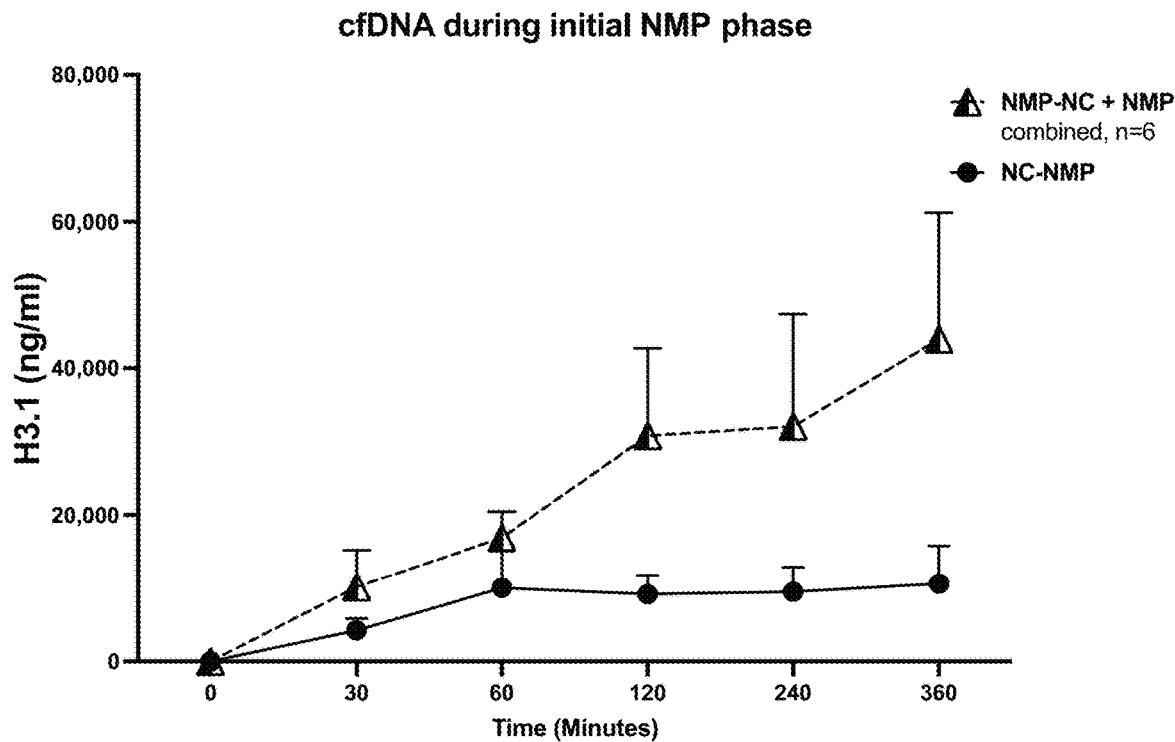
Figure 15D:
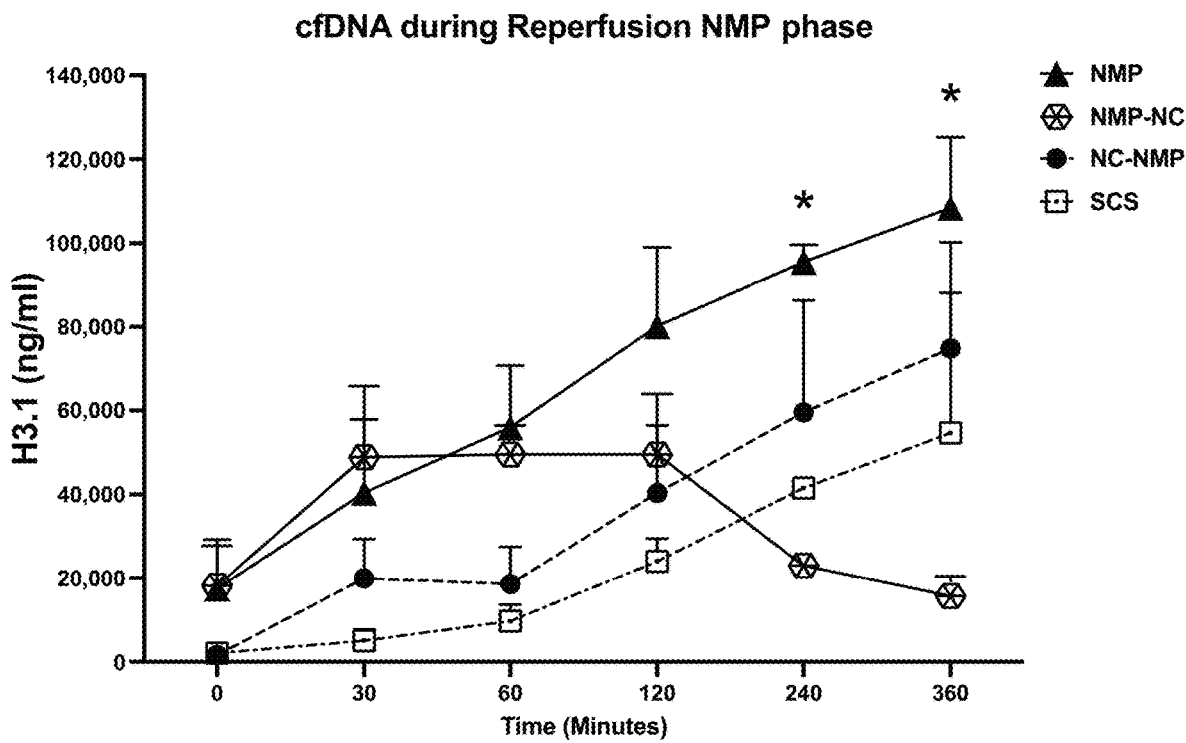

FIGS. 15A-B show the graphs representing the arterial lactate levels in the perfused liver during perfusion and reperfusion stage in 4 experimental groups. Group SCS: 3 livers subjected to 6 hours of cold storage followed by 6 hours of reperfusion with allogeneic porcine blood; Group NMP: 3 livers subjected to 6 hours of Metra normothermic machine perfusion with autologous blood followed by 6 hours of reperfusion with allogeneic porcine blood; Group NMP_NC: 3 livers subjected to 6 hours of Metra normothermic machine perfusion with Metra perfusion solution and use of NucleoCapture device (H1.3 histone affinity matrix) during NMP stage followed by 6 hours of reperfusion with allogeneic porcine blood; Group RP_NC: 3 livers subjected to 6 hours of Metra normothermic machine perfusion with Metra perfusion solution followed by 6 hours of reperfusion with allogeneic porcine blood solution and use of NucleoCapture device during reperfusion stage. FIG. 15C is the graph representing cfDNA content (in ng/ml as measured by the Nu.Q® H3.1 assay) in perfusate during NMP stage (mean values with SEM bars shown). FIG. 15D is the graph representing cfDNA content (ng/ml) in circuit during reperfusion stage.

Figure 16:
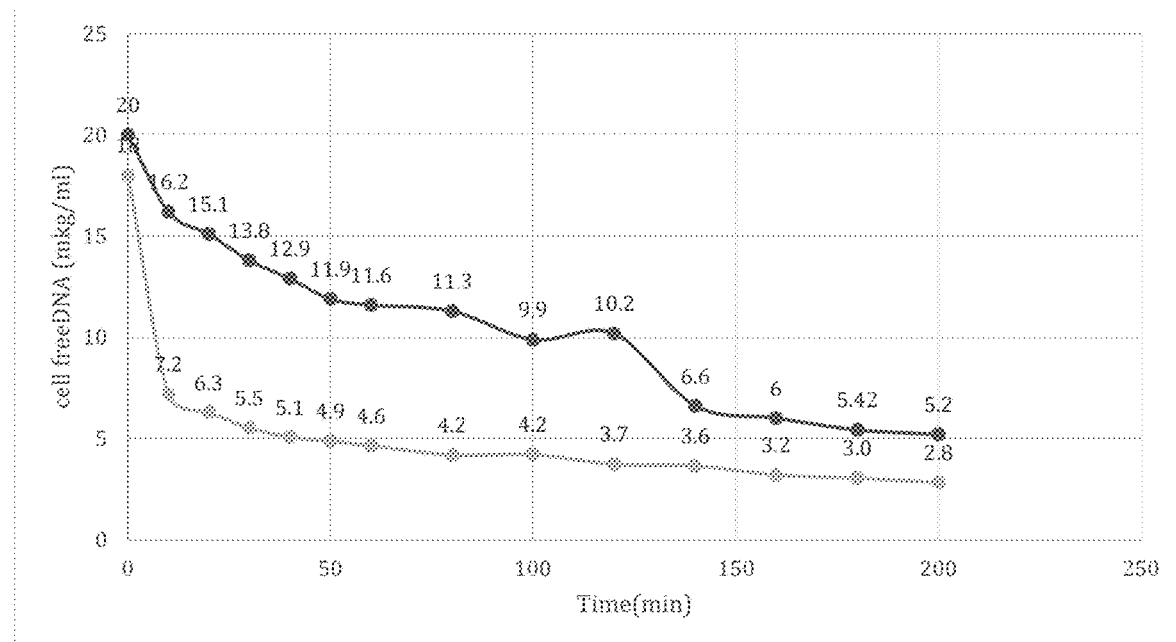

FIG. 16 shows the content of cfDNA in blood during the perfusion. Black line—cfDNA in the inlet; grey line—cfDNA in the outlet.

Figure 17:
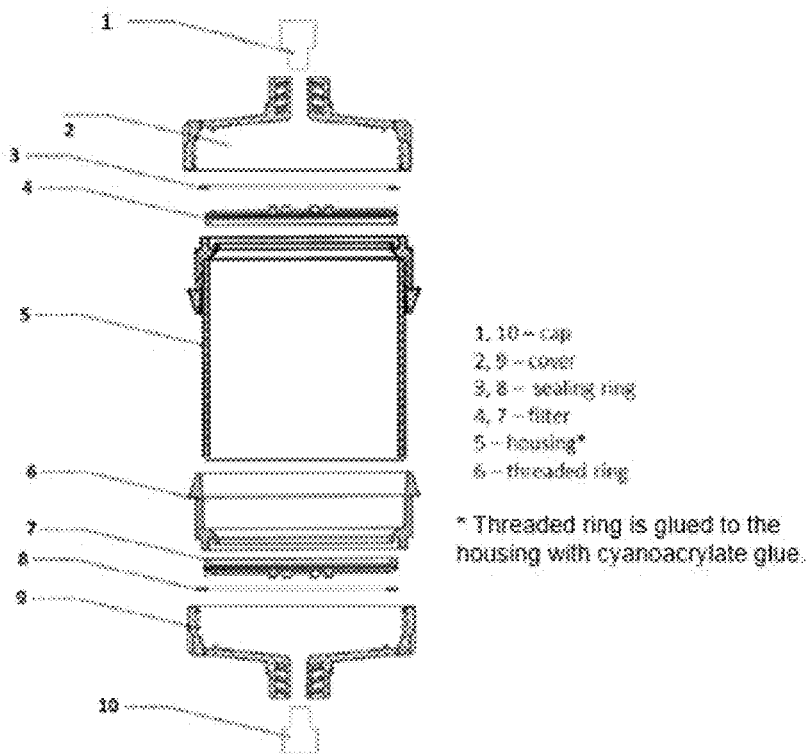

FIG. 17 shows a schematic representation of the plastic housing of the NucleoCapture column (H1.3 histone affinity matrix).

Figure 18A:
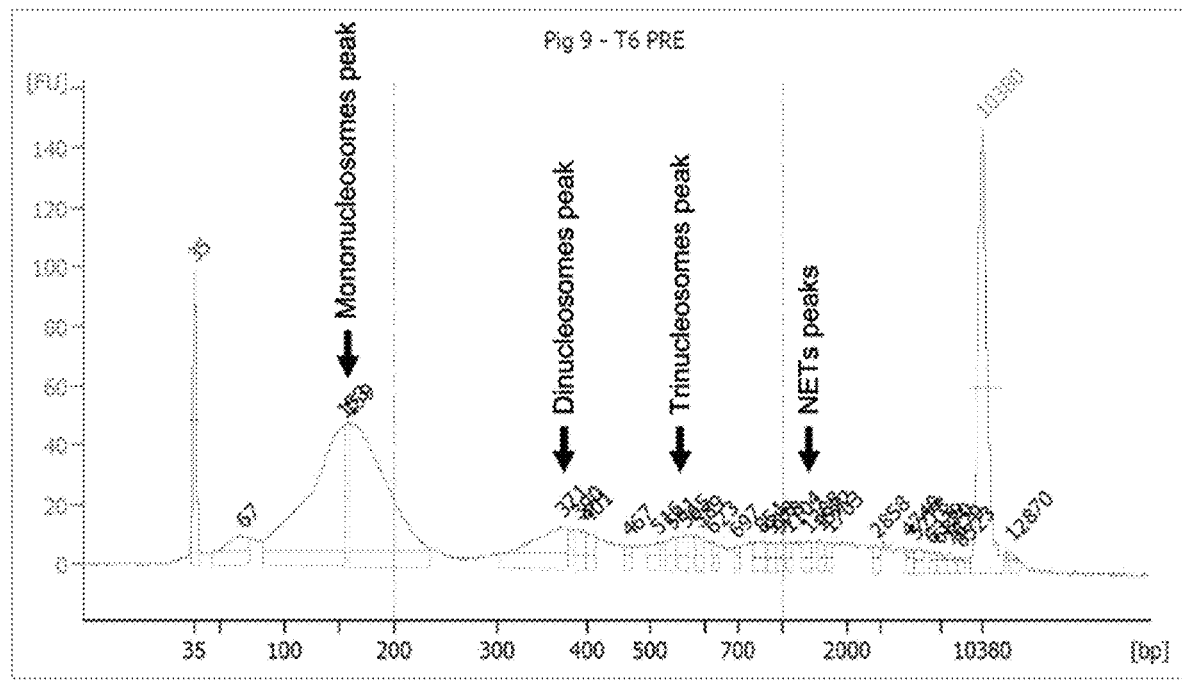
Figure 18B:
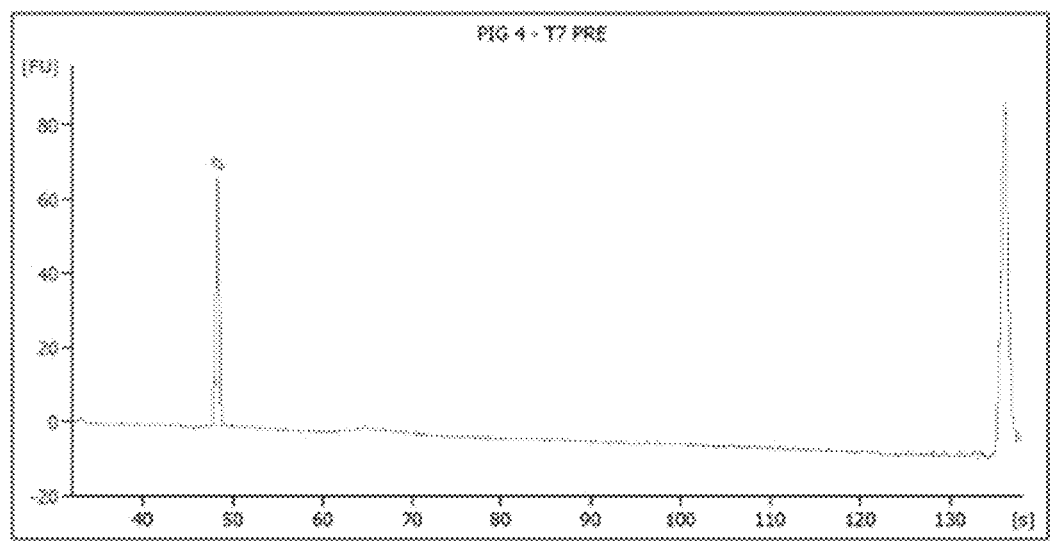

FIGS. 18A-B show bioanalyzer profile of cfDNA in plasma: (A) plasma prior to passage through NucleoCapture column (H1.3 histone affinity matrix)—cfDNA of various molecular weight present in plasma; (B) plasma after passage through NucleoCapture column—no cfDNA detected.

Figure 19:
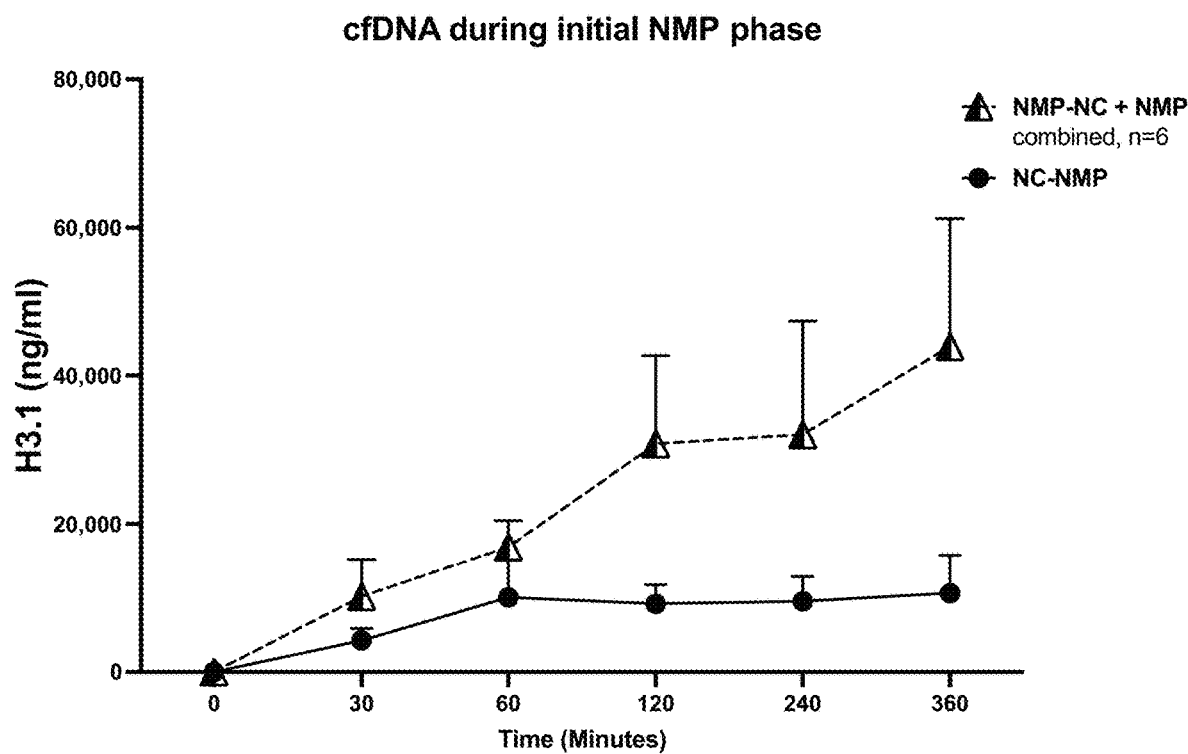

FIG. 19 shows cfDNA levels quantified hourly in perfusion solution using Nu.Q® H3.1 assay in liver perfusate after livers were perfused on the OrganOx Metra® device as standard, with the perfusate composed of autologous leukodepleted blood for 6 hours.

Figure 20:
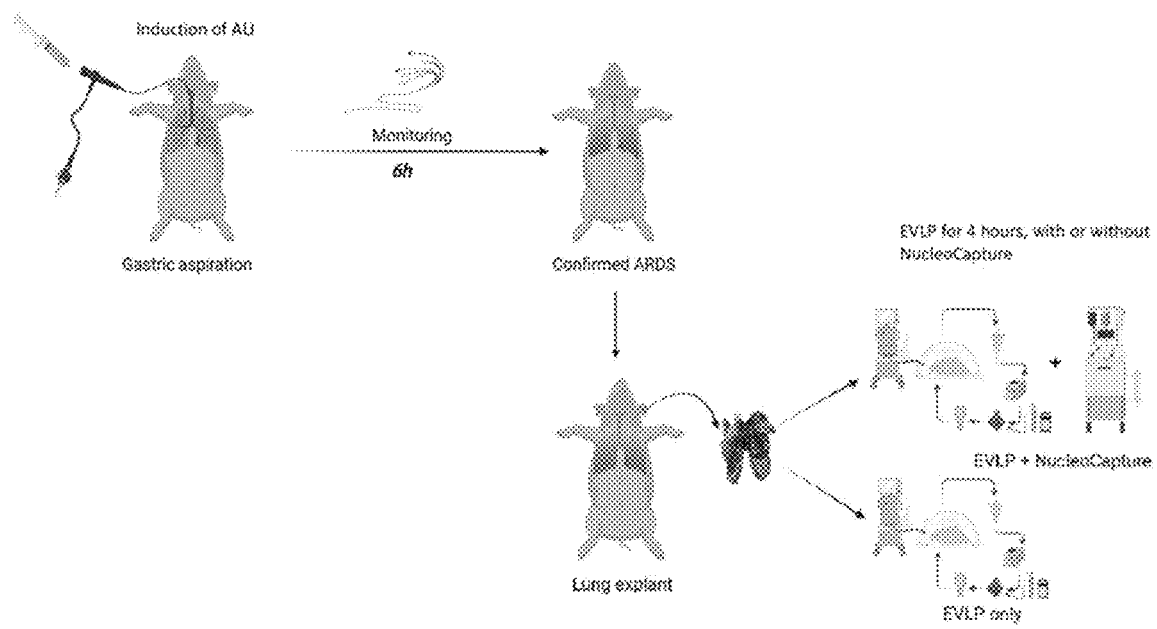

FIG. 20 shows experiment setup used in Example 30.

Figure 21:
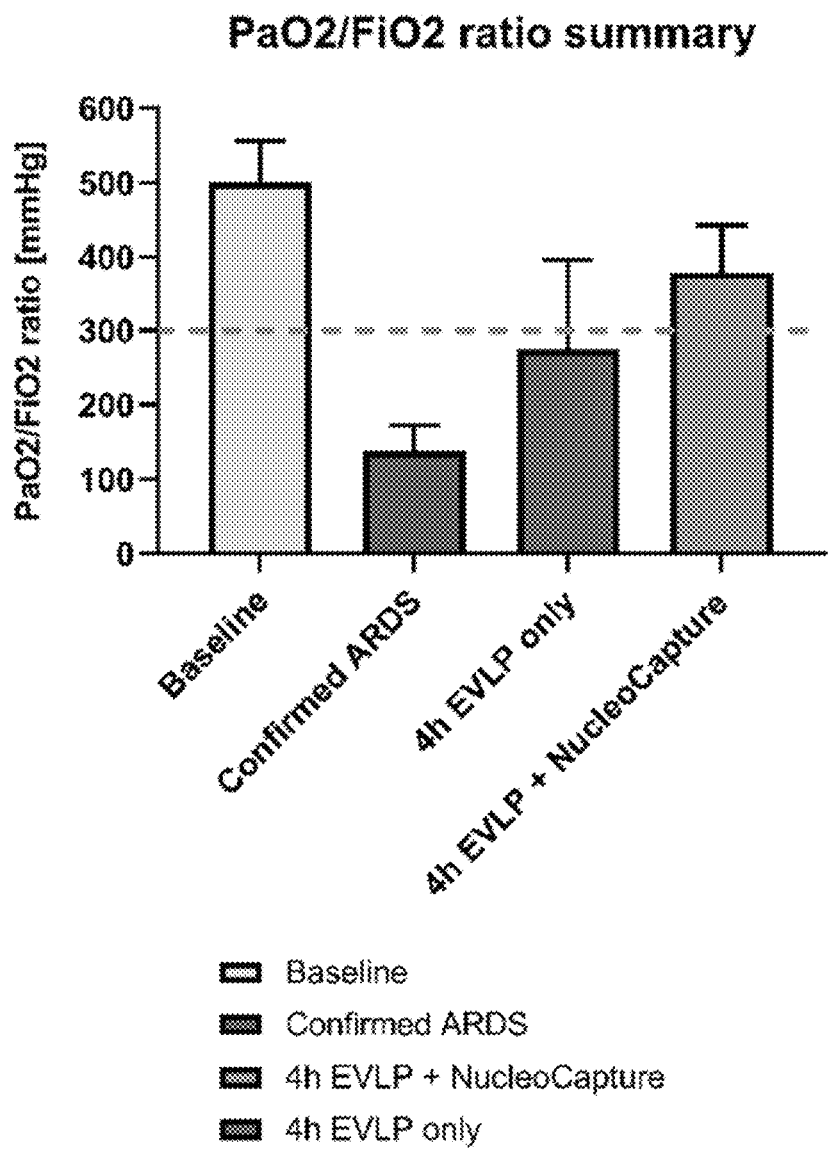

FIG. 21 is a graph showing the effect of NucleoCapture apheresis on the outcome of the EVLP procedure measured as final $PO_2/FiO_2$ ratio.

Figure 22:
Figure 22:
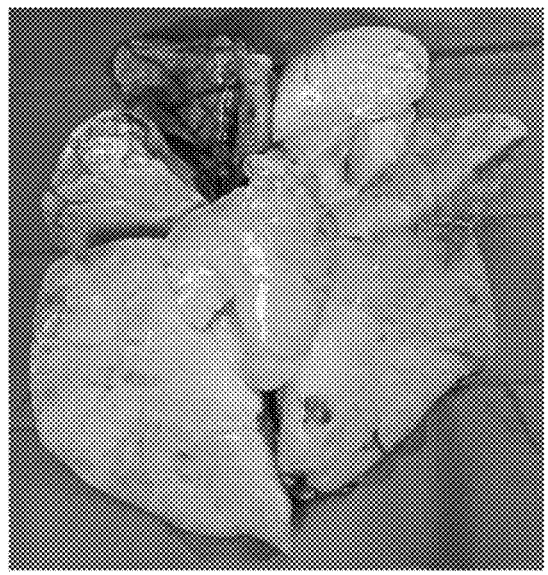

FIG. 22 shows macroscopic appearance of lungs treated with EVLP without NucleoCapture apheresis and lungs treated with EVLP and NucleoCapture apheresis.

FIGS. 23A-F. (A) Typical images of lung sections stained with haematoxylin and eosin (H&E). Arrows indicate alveolar neutrophils, interstitial neutrophils, hyaline membrane, proteinaceous debris, septal thickening and NETs. Mean±SE lung injury score is represented in (B) for the different groups. Independent T-test, *P<0.001 compared with baseline, #P<0.01 compared with EVLP alone. (C) Typical lung section images with anti-citrullinated histone H3 (Cit-H3) for NETs. Black arrows indicate NETs. Mean±SE NET formation score is represented in (D). Independent t-test, *P<0.001 compared with baseline, #P<0.001 compared with EVLP alone. (E) Typical lung section images with anti-fibrin immunohistochemistry stain. Black arrows indicate fibrin deposition. Mean±SE Fibrin deposition score is represented in (F). Independent t-test, *P<0.01 compared with baseline, #P<0.001 compared with ARDS.

DETAILED DESCRIPTION OF THE INVENTION

Definitions

Unless defined otherwise, all technical and scientific terms used herein have the same meaning as commonly understood by one of ordinary skill in the art to which this invention belongs.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The term "device" as used herein refers to any assembly known in the art to enable the purification of liquid solutions, such as, without limitation, e.g., any hollow-ware, a column, a column matrix, a filter, a membrane, a semipermeable material, a bead (e.g., a microbead or a nanobead, including magnetic beads), or a tubing. The terms "column" and "cartridge" are used interchangeably herein in the context of an apheresis device or an analytical device.

The term "affinity matrix" as used herein refers to (i) a solid support onto which a ligand (e.g., a cfDNA-binding molecule) is immobilized or to (ii) a solid support formed by the ligand itself (e.g., a water-insoluble oligomer, polymer or co-polymer comprising any of the cfDNA-binding molecules described herein).

In the context of the present invention, the term "liquid biopsy" refers to a broad category of minimally invasive tests performed to look for fragments of disease-associated DNA in a sample of a biofluid. See, for example, Merker at al., (2018) Circulating Tumor DNA Analysis in Patients with Cancer: American Society of Clinical Oncology and College of American Pathologists Joint Review, Journal of Clinical Oncology 36(16): JCO2017768671, DOI: 10.1200/JCO.2017.76.8671.

The term "DNA-binding protein" refers to proteins that bind to single-stranded DNA (ssDNA) or double-stranded DNA (dsDNA). DNA binding proteins can bind DNA in sequence-specific manner (e.g., transcription factors and nucleases) or non-sequence specifically (e.g., polymerases and histones).

As used herein, the term "histone" refers to the primary protein components of chromatin. Histones can be grouped into core histones and linker histones. Two of each of the four core histones, H2A, H2B, H3 and H4, form an octamer around which approximately 147 bp of DNA are wrapped—these are nucleosomal core particles which are the basic structural unit of DNA (see e.g., Luger et al., Nature, 1997, 389(6648):251-260). Nucleosomes are separated from each other by the linker stretches of nucleotides that are generally up to 80 base pairs long. The histone H1 binds to the nucleosomal core particles close to the DNA entry and exit sites and protects the linker DNA (~20 bp) between the individual nucleosomal core particles. These full nucleosomes (also referred to as chromatosomes) are necessary for the formation of higher order chromatin structures in vivo.

The term "linker histone" refers to histones which bind to the nucleosome core particle at the linker (internucleosomal) DNA entry and exit points, provide an interaction region between adjacent nucleosomes and generate second-order chromatin structure (i.e., nucleosomal filament) by drawing adjacent nucleosomes together. Linker histones typically (but not always) possess a tripartite structure conserved across all eukaryotes, including a short and flexible N-terminal tail, a structured globular domain (GH1) which interacts with a nucleosome dyad, and a structurally disordered, lysine-rich C-terminal tail. The C-terminal tails vary in length and composition among linker histone isotypes and organisms. The linker histones H1 and H5 are the most divergent group of the histone proteins. Histone H1 protein family comprises 12 subtypes. The individual subtypes can be grouped into 3 distinct groups: (i) the somatic replication-dependent subtypes (H1.1-H1.5) that are expressed mainly in the S-phase, (ii) the somatic replication-independent variants (H1.0 and H1.10) expressed during the complete cell cycle and (iii) the germ line-specific (testis or oocyte) subtypes (H1.6 (TS), H1.7 (TS), two splice variants of H1.8 (OO) and H1.9 (TS)). See, e.g., Brockers, K., Schneider, R., Epigenomics, 2019, 11(4):363-366; doi: 10.2217/epi-2019-0018; Hergeth, S. P., Schneider, R., EMBO Rep., 2015; 16(11): 1439-1453; doi:10.15252/embr.201540749. A specific subtype of linker histones, histone H5, has been found to accumulate in nucleated avian erythrocytes. Histone H5 is a counterpart of mammalian histone H1.0 and both of them are considered to be differentiation-specific histone subvariants (Gunjan, A, et al., J Biol Chem. 1999; 274(53):37950-6; Smith B J, et al., FEBS Lett., 1980; 112(1):42-44; Koorsen, G (2010) "The binding of linker histone H5 to DNA and chromatin" VDM publishing, ISBN3639222105. The terms "high mobility group proteins" and "HMG proteins" refer to a class of non-histone DNA binding proteins that bind DNA and regulate chromatin structural organization and various DNA-associated processes. See, e.g., Reeves R., DNA Repair, 2015, 36:122-136. The high mobility group box 1 (HMGB-1) protein belongs to the family of HMG proteins. Without wishing to be bound by theory, similar to histones, the HMGB-1 protein may interact with internucleosomal (linker) DNA. HMGB-1 protein may participate in such processes as, for example, the regulation of DNA repair, transcription, replication, and recombination. Another non-limiting example of HMG protein is cGAS (see, e.g., Mandke and Vasquez, DNA Repair, 2019, vol. 83, art. 102701).

As used herein, the terms "circulating DNA", "cell free DNA (cfDNA)", "circulating cell free DNA (circulating cfDNA)", "extracellular DNA (eDNA)", and "circulating extracellular DNA (circulating eDNA)" are used interchangeably to refer to (i) DNA present in a bodily fluid outside of circulating cells of hematopoietic and non-hematopoietic origin as well as (ii) DNA present in any of various perfusion solutions that may be used in accordance with the present invention (see, for example, www.xvivoperfusion.com/products/steen-solution/; www.transmedics.com/ocs-hcp-lung/). Such perfusion solutions may be useful, for example, in the practice of methods of in vivo or ex vivo perfusion of an organ and/or anatomical cavity. In certain aspects, the perfusion solution disclosed herein may comprise a bodily fluid.

Nucleosome-bound cfDNA is DNA that is bound to a nucleosome. A nucleosome is a subunit of nuclear chromatin. Nucleosome-bound cfDNA might circulate in a bodily fluid, or in a perfusion solution disclosed herein, as mono-nucleosomes or higher order structures such as oligonucleosomes or even fragments of chromatin containing over $50$-$100 \times 10^3$ base pairs of DNA. Circulating nucleosome-bound cfDNA may originate from cells undergoing necrosis, apoptosis, pyroptosis, necroptosis and from neutrophil NETosis.

Exosome-bound cfDNA is cfDNA that is bound to exosomes or is present in exosomes. Exosomes are small membrane vesicles (about 30-100 nm) of exocytotic origin secreted by most cell types that might contain single-stranded DNA (ssDNA), mitochondrial DNA (mtDNA) and double-stranded DNA (dsDNA) at the inner or outer space of exosome.

The terms "unbound cfDNA", "cfDNA free of particles" and "particle free cfDNA" are used interchangeably to refer to cfDNA which is not bound to exosomes or nucleosomes and encompass double-stranded DNA (dsDNA), single-stranded DNA (ssDNA), linear and circular polynucleotides and oligonucleotides, including ultra-short DNA molecules of subnucleosomal size (e.g., less than 147 base pairs).

As used herein, the terms "biological fluid", "biofluid" and "bodily fluid" are used interchangeably to refer to any kind of bodily fluid which can contain cfDNA, including, without limitation, blood, plasma, serum, cerebrospinal fluid (CSF), lymph, glymph, endometrial fluid, urine, saliva, synovial fluid, sputum, tears, mucus, bile, peritoneal fluid, pleural fluid, semen, sweat, gastric juice, breast milk, and vaginal secretions.

As used herein, the term "perfusion" encompasses creating a flow through an organ generated by a pump in a circuit to recirculate a preservative solution at various temperatures through the vasculature. Non-limiting examples of perfusion include extracorporeal machine perfusion, a perfusion of an isolated anatomical cavity (e.g., in situ regional peritoneal cavity perfusion), a perfusion in a donor (e.g., after cardiac death (DCD) or brainstem death (DBD)), including, without limitation, the use of hypothermic and normothermic techniques (e.g., normothermic machine perfusion (NMP), abdominal normothermic regional perfusion (A-NRP), thoracic NRP, combined thoracoabdominal NRP, hypothermic oxygenated machine perfusion (HOPE, e.g. cold perfusion with University of Wisconsin solution). Abdominal normothermic regional perfusion (A-NRP) is a technique used to restore the circulation to the abdominal organs following circulatory arrest for the purpose of transplantation. In some embodiments, A-NRP involves establishing a localized, abdominal perfusion extracorporeal membrane oxygenation (ECMO) circuit, perfusing the organs with oxygenated blood at about 37° C. for a period of about 2 hours. A-NRP has been shown to improve transplant quality and/or survival for all abdominal organs, especially liver and kidneys (see, e.g., van de Leemkolk et al., Transplantation, 2020, 104(9): 1776-1791).

As used herein, the term "sequence identity" means that the same amino acid residues are found within the target sequence and a reference sequence when a specified, contiguous segment of the amino acid sequence or the nucleotide sequence of the target sequence is aligned and compared to the amino acid sequence or nucleotide sequence of the reference sequence. Methods for sequence alignment and for determining sequence identity between sequences are well within the knowledge of one skilled in the art. See, e.g., Ausubel et al., eds. (1995) Current Protocols in Molecular Biology, Chapter 19 (Greene Publishing and Wiley-Interscience, New York); and the ALIGN program (Dayhoff (1978) in Atlas of Polypeptide Sequence and Structure 5: Suppl. 3 (National Biomedical Research Foundation, Washington, D.C.).

As used herein, the terms "subject" and "patient" are used interchangeably and refer to animals, including mammals such as humans, veterinary animals (e.g., cats, dogs, cows, horses, sheep, pigs, etc.), and experimental animal models. In certain embodiments, the subject refers to a human patient, including both genders in adult and child populations.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. The terms "treat", "treatment", and the like regarding a state, disorder or condition may also include (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The practice of the present invention employs, unless otherwise indicated, conventional techniques of statistical analysis, molecular biology (including recombinant techniques), microbiology, cell biology, conjugation chemistry and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ Hermanson (2013) Bioconjugate Techniques, 3rd ed., Academic Press; Niemeyer (2004) Bioconjugation Protocols: Strategies and Methods, Springer Science & Business Media and Hermanson et al. (1992) Immobilized Affinity Ligand Techniques, Academic Press. Additional techniques are explained, e.g., in U.S. Pat. No. 7,912,698 and U.S. Patent Appl. Pub. Nos. 2011/0202322 and 2011/0307437.

Devices and Methods of the Invention

As specified in the Background Section, there is a great need in the art to develop new methods and devices for substantially reducing the level of all types of circulating cfDNA in the blood. The present disclosure addresses this and other needs by providing apheresis devices and methods, wherein the apheresis device substantially reduces the level of all types of cfDNA, including nucleosome-bound cfDNA, exosome-bound cfDNA and unbound cfDNA (including dsDNA, ssDNA and oligonucleotides).

The use of extracorporeal removal technologies can provide an effective solution to eliminate cfDNA from circulation and, correspondingly, decrease the level and negative effects of circulating cfDNA. Therapeutic apheresis is an example of a type of extracorporeal treatment that removes blood components from patients; it is used for the treatment of conditions in which a pathogenic substance or component in the blood is causing development of diseases: see for example, Ward M. D., Conventional Apheresis Therapies: A Review Journal of Clinical Apheresis 26:230-238 (2011).

As demonstrated herein, the substantial extracorporeal removal of all types of circulating cfDNA has a positive impact on the treatment of diseases characterized by elevated circulating levels of cfDNA in one or more bodily fluids (e.g., blood, serum, plasma, CSF, etc.).

The present disclosure provides a method for treating diseases characterized by elevated circulating levels of cfDNA through the substantial removal of all types of cfDNA, including nucleosome-bound cfDNA, exosome-bound cfDNA and unbound cfDNA (including dsDNA, ssDNA and oligonucleotides) from one or more bodily fluids (e.g., blood, serum, plasma, cerebrospinal fluid (CSF), endometrial fluid, urine, saliva, lymph, glymph, tear fluid, sweat, synovial fluid, sputum) of a subject to reduce the negative effects of the circulating cfDNA.

Without wishing to be bound by theory, in certain diseases, wherein the level of circulating cfDNA is increased, different types of circulating cfDNA might act in concert by triggering different molecular pathways each leading to disease progression and patient mortality; different types of circulating cfDNA acting together might generate synergistic toxicity, i.e., toxic (negative) effect of two or more types of circulating cfDNA is greater than the sum of the negative effects of each type of cfDNA taken separately. The amount and state of cells in the body associated with a disease (e.g., cancer cells or immunopathological conditions, for example, systemic inflammatory response syndrome [SIRS] or sepsis) can influence the overall amount of cfDNA. In addition, the presence and state of such cells (e.g., in cancer, the tumor type, progression, burden, proliferation rates, and therapy or e.g., in sepsis, sepsis stage, degree of organ-failures, and therapy) can affect the quantity and quality (e.g., methylation pattern, size of DNA fragments, fragment size distribution pattern) of cfDNA. These factors can also affect the amount of specific cfDNAs, for example, nucleosome-bound DNA, exosome-bound cfDNA, unbound DNA (including double stranded DNA [dsDNA], single stranded DNA [ssDNA] and oligonucleotides), or any of various tumor-derived cfDNA (ctDNA), or NET-derived DNA.

The inventors have found that the substantial removal of all types of cfDNA, including nucleosome-bound cfDNA, exosome-bound cfDNA and unbound cfDNA (including double stranded DNA [dsDNA], single stranded DNA [ssDNA] and oligonucleotides) from one or more bodily fluids (e.g., blood, serum, plasma, cerebrospinal fluid (CSF), endometrial fluid, urine, saliva, lymph, glymph, tear fluid, sweat, synovial fluid, sputum) of patients with increased levels of circulating cfDNA can effectively reduce or even fully abolish the pathogenic effects mediated by said circulating cfDNA. The substantial removal of all types of cfDNA, including nucleosome-bound cfDNA, exosome-bound cfDNA and unbound cfDNA (dsDNA, ssDNA and oligonucleotides) appears critical for reducing pathogenic effects mediated by cfDNA.

The inventors have additionally found that removal of cfDNA, from a perfusion solution or body fluid used, for example, in the in vivo and/or ex vivo perfusion of an organ (e.g., liver, lung, kidney, or heart) effectively reduces or even fully abolishes organ reperfusion injury.

The inventors have additionally found that removal of cfDNA, from a perfusion solution used, for example, in the in vivo and/or ex vivo perfusion of an anatomical cavity (e.g., peritoneal or thoracic) with increased levels of circulating cfDNA can effectively reduce or even fully abolish the pathogenic effects mediated by said circulating cfDNA.

The inventors further observed that the substantial removal of all types of circulating cfDNA might lead to reactivation of endogenous deoxyribonucleases (DNases).

It is further described herein that several affinity matrices or combinations thereof are able to effectively substantially capture all types of cfDNA, including nucleosome-bound cfDNA, exosome-bound cfDNA and unbound cfDNA (including dsDNA, ssDNA and oligonucleotides) from one or more bodily fluids of patients in need thereof. It is even further described herein that several affinity matrices or combinations thereof are able to effectively substantially capture all cfDNA, including nucleosome-bound cfDNA, exosome-bound cfDNA and unbound cfDNA (including dsDNA, ssDNA and oligonucleotides) from any of a number of various perfusion solutions that may be useful in the practice of ex vivo and in vivo perfusion methods comprising perfusion of an organ and/or anatomical cavity. Examples of affinity matrices useful in apheresis devices and methods of the invention include (i) matrices comprising a DNA binding protein (e.g., a histone [e.g., a linker histone such as, e.g., an H1 histone] or a high mobility group protein [e.g., HMGB-1 or cGAS]), (ii) matrices comprising an anti-histone antibody (e.g., an anti-histone H2A antibody) and/or an anti-nucleosome antibody (e.g., AN-1, AN-44), (iii) matrices comprising a DNA intercalating agent (e.g., polymyxin B, a Hoechst dye such as, e.g., Hoechst 33342, or chloroquine), (iv) matrices comprising a DNA-binding polymer (e.g., a cationic/basic polymer [e.g., polyethylenimine, poly-L-lysine, poly-L-arginine, hexadimethrine bromide, amino terminated (—NH$_2$) polyamidoamine (PAMAM) dendrimer, polypropyleneimine (PPI) dendrimer], a non-ionic/neutral polymer [e.g., polyvinylpyrrolidone (PVP), polyvinylpolypyrrolidone (PVPP), poly (4-vinylpyridine-N-oxide)], an anionic/acidic polymer; a linear polymer [e.g., polyethylenimine, poly-L-lysine, poly-L-arginine], a branched polymer [e.g., hyper-branched poly-L-lysine, hyper-branched polyethylenimine], a dendrimeric polymer [e.g., polyamidoamine (PAMAM) dendrimer, polypropyleneimine (PPI) dendrimer; see, e.g., Kaur et al., J Nanopart Res., 2016, 18:146]; see, e.g., U.S. Pat. No. 7,713,701 and Morozov et al., General Reanimatology, 2016, 12:6 for additional examples), (v) matrices comprising an anti-DNA antibody, (vi) matrices comprising a lectin (e.g., *Galanthus nivalis* Lectin (GNA), *Narcissus Pseudonarcissus* Lectin (NPA), Conconavalin A, phytohemagluttanin, or cyanovirin), (vii) matrices comprising a polysaccharide (e.g., heparin) and any combination thereof. In some embodiments, two or more affinity matrices are sequentially arranged as two or more affinity columns. In some embodiments, the first affinity matrix in the sequence comprises a DNA binding polymer (e.g., amino terminated (—NH$_2$) polyamidoamine (PAMAM) dendrimer, polypropyleneimine (PPI) dendrimer, hyper-branched poly-L-lysine, or hyper-branched polyethylenimine) or a DNA intercalating agent (e.g., polymyxin B, Hoechst 33342 or chloroquine).

Described herein are affinity matrices and apheresis devices comprising such matrices. An apheresis device of the invention may be configured according to the knowledge of one of ordinary skill in the art, for example as described in U.S. Patent Appl. Pub. No. 2017/0035955. In one embodiment of the apheresis device, affinity matrices are placed into various affinity columns, or cartridges. The apheresis device can comprise a filtration cartridge and one or more affinity columns having an inlet and an outlet, in which the device is capable of capturing nucleosome-bound cfDNA, exosome-bound cfDNA and unbound cfDNA (including dsDNA, ssDNA and oligonucleotides), from a bodily fluid (e.g., blood, serum, plasma, cerebrospinal fluid (CSF), endometrial fluid, urine, saliva, lymph, glymph, tear fluid, sweat, synovial fluid, sputum) of a patient, or from perfusion solutions useful in the practice of methods of in vivo or ex vivo perfusion of an organ (e.g., liver, lung, kidney, heart) and/or anatomical cavity (e.g., peritoneal or thoracic) disclosed herein. In some embodiments, the device comprises two or more affinity columns arranged in sequence. The inlet and outlet can be positioned with respect to the affinity matrices such that the bodily fluid or the perfusion solution entering the inlet must contact the affinity matrices before exiting through the outlet. Preferably, the geometry of the device is designed to maximize contact of the bodily fluid or the perfusion solution with the affinity matrices during passage through the device. A variety of such designs are known in the art. For example, the device can be a hollow cylinder packed with an affinity ligand immobilized on beads, having the inlet at one end and the outlet at the opposite end (see FIG. 17). Other devices, such as microtubule arrays, can be also constructed. All such variations of container geometry and volume and of the affinity matrices contained therein can be designed according to known principles. In preparing an affinity matrix column, the affinity matrix may be loaded to at least 50%, 60%, 70%, 75%, 80%, 85%, or 90% column volume. A suitable buffer (e.g., PBS, particularly cold PBS) may be used to equilibrate the column.

In one embodiment, provided herein is a histone affinity matrix comprising cellulose beads and recombinant human histone H1.3, wherein the recombinant human histone H1.3 is immobilized on the cellulose beads and wherein the size of the beads is between 50 and 350 µm. In some embodiments, the size of the beads is between 100 and 250 µm.

In some embodiments, the histone affinity matrix is prepared by a process comprising
 a) oxidizing cellulose beads having a size between 100 and 250 µm to yield activated cellulose beads;
 b) washing the activated cellulose beads;
 c) preparing a concentrated solution of recombinant human histone H1.3;
 d) incubating the activated cellulose beads with the concentrated solution of recombinant human histone H1.3; and
 e) blocking any free CHO groups on the activated cellulose beads.

In some embodiments, the process further comprises f) washing the activated cellulose beads with buffer.

In some embodiments, in step a), the cellulose beads are in an aqueous suspension and oxidized with NaIO. In some embodiments, in step b), the activated cellulose beads are washed with sodium bicarbonate, hydrochloric acid and water. In some embodiments, step c) comprises dialyzing a solution of recombinant human histone H1.3 and concentrating the dialyzed solution in 0.1 M NaHCO$_3$ at pH 7-9. In some embodiments, the dialyzed solution is concentrated in 0.1 M NaHCO$_3$ at pH 8. In some embodiments, in step d) the incubation is performed for 3-5 hours at 15-30° C. In some embodiments, in step d) the incubation is performed for 4 hours at room temperature. In some embodiments, in step e) the blocking step comprises adding 1 M ethanolamine to the activated cellulose beads and reacting for 30 minutes to 2 hours at 15-30° C. In some embodiments, in step f) the activated cellulose beads are washed with TBS buffer.

Also provided herein is a column comprising the histone affinity matrix of any of the aspects and embodiments above.

In another embodiment, provided herein is a lectin affinity matrix prepared according to a process comprising
 a) reacting lectin with activated agarose beads to yield lectin-coupled agarose; and
 b) washing the lectin-coupled agarose with buffer.

In some embodiments, the lectin is from *Galanthus nivalis* (snowdrop). In some embodiments, the activated agarose beads are CNBr activated agarose beads. In some embodiments, the buffer is PBS, such as, e.g., sterile cold PBS at pH 7.2-7.4.

Also provided herein is a column comprising the lectin affinity matrix of any of the aspects and embodiments above.

In yet another embodiment, provided herein is a polyamidoamine dendrimer affinity matrix (PDAM) prepared by a process comprising
 a) washing cellulose beads with ethanol and water;
 b) incubating the washed cellulose beads with (±)-epichlorohydrin and NaOH to yield activated cellulose beads;
 c) reacting the activated cellulose beads with polyamidoamine (PAMAM) dendrimer to yield PDAM beads and removing PAMAM dendrimer that did not react with the activated cellulose beads; and
 d) blocking unconverted epoxy groups on the PDAM beads.

In some embodiments, the process further comprises e) washing the PDAM beads with 0.1 M phosphate buffer and water.

In some embodiments, in step a) the cellulose beads are washed with 98% ethanol and distilled water. In some embodiments, in step b) the washed cellulose beads are incubated with a mixture of (±)-epichlorohydrin and 2.5 M NaOH. In some embodiments, in step c), the activated cellulose beads are suspended with a 20% solution of PAMAM dendrimer with an ethylenediamine core. In some embodiments, in step c) the suspending is conducted at 20-30° C. for 3-6 hours. In some embodiments, in step c) the suspending is conducted at 24° C. for 5 hours.

Also provided herein is a column comprising a PAMAM dendrimer affinity matrix (PDAM) described above. In some embodiments, the column is a PTFE column, and the polyamidoamine dendrimer affinity matrix is sterilized.

In another embodiment, provided herein is an anti-DNA antibody affinity matrix prepared by a process comprising
 a) preparing activated agarose beads by crosslinking N-hydroxysuccinimide with agarose beads;
 b) washing the activated agarose beads with coupling buffer comprising NaHCO$_3$ and NaCl;
 c) adding an antibody against double stranded and single stranded DNA to the coupling buffer;
 d) incubating the coupling buffer comprising the antibody with the activated agarose beads to yield the anti-DNA antibody affinity matrix; and
 e) washing the anti-DNA antibody affinity matrix with coupling buffer and acetate buffer.

In some embodiments, the agarose beads have a mean size of 90 μm. In some embodiments, the coupling buffer comprises 0.2 M NaHCO$_3$ and 0.5 M NaCl and is at pH 8.3. In some embodiments, the antibody is a monoclonal antibody. In some embodiments, the antibody is a mouse antibody. In some embodiments, the washing step is performed at least three times. In some embodiments, the acetate buffer is 0.1 M acetate buffer at pH 4.0.

Also provided herein is a column comprising an anti-DNA antibody affinity matrix described above.

In some embodiments, the column is prepared by incubating the anti-DNA antibody affinity matrix with sterile Tris-HCl buffer. In some embodiments, the sterile Tris-HCl buffer is at pH 7.4.

In another embodiment, provided herein is an anti-nucleosome antibody affinity matrix (ANAM) prepared by a process comprising
 a) preparing activated agarose beads by crosslinking N-hydroxysuccinimide with agarose beads;
 b) washing the activated agarose beads with coupling buffer comprising NaHCO$_3$ and NaCl;
 c) adding to the coupling buffer an antibody that binds to nucleosomes, wherein the antibody is prepared in a MRL/Mp (−)+/+ mouse;
 d) incubating the coupling buffer comprising the antibody with the activated agarose beads to yield the anti-nucleosome antibody affinity matrix; and
 e) washing the anti-nucleosome antibody affinity matrix with coupling buffer and acetate buffer.

In some embodiments, the matrix binds to nucleosome bound circulating cfDNA, and the matrix does not bind to unbound cfDNA that includes dsDNA, ssDNA and oligonucleotides.

Also provided herein is a column comprising an anti-nucleosome antibody affinity matrix (ANAM) described above.

In yet another embodiment, provided herein is a DNA intercalating agent Hoechst 33342 affinity matrix prepared by a process comprising
 a) oxidizing cellulose beads;
 b) washing the oxidized cellulose beads;
 c) reacting the washed oxidized cellulose beads with a solution comprising Hoechst 33342 and N-(3-dimethylaminopropyl)-N'-ethyl carbodiimide (EDC) to yield Hoechst 33342 immobilized cellulose beads; and
 d) washing the Hoechst 33342 immobilized cellulose beads.

In some embodiments, in step a) the cellulose beads are oxidized with NaIO for 3-5 hours. In some embodiments, in step b) the oxidized cellulose beads are washed with 1 M sodium bicarbonate, 0.1 M hydrochloric acid and water. In some embodiments in step c), the solution is a pH buffered solution. In some embodiments in step d), the washing is conducted at least three times.

In another embodiment, provided herein is a hyper-branched poly-L-lysine affinity matrix (PLLAM) prepared by a process comprising
 a) dissolving L-lysine monohydrochloride in water and neutralizing with KOH to yield an L-lysine solution;
 b) heating the L-lysine solution to yield a solution comprising hyper-branched poly-L-lysine;
 c) removing the L-lysine and salt from the solution comprising hyper-branched poly-L-lysine;
 d) fractionating the solution comprising hyper-branched poly-L-lysine to obtain a fraction comprising hyperbranched poly-L-lysine with an average molecular weight of 21,000 to 32,000;

e) dialyzing and lyophilizing the fraction comprising hyper-branched poly-L-lysine with an average molecular weight of 21,000 to 32,000 to yield a lyophilizate;

f) dissolving the lyophilizate in distilled water and dialyzing against $NaHCO_3$ to yield a solution comprising HBPL; and g) incubating the solution comprising hyper-branched poly-L-lysine with cyanogen bromide-activated Sepharose 4B suspended in $NaHCO_3$ to prepare hyper-branched poly-L-lysine affinity matrix.

In some embodiments, in step b) the L-lysine solution is heated to 150° C. for 48 hours under a stream of nitrogen. In some embodiments, in step c), the solution comprising hyper-branched poly-L-lysine is dialyzed against water. In some embodiments, in step d) the fractionation is conducted with a size exclusion column. In some embodiments, in step d), the fractionation is conducted with a gel filtration column.

Also provided herein is a column comprising a hyper-branched poly-L-lysine affinity matrix (PLLAM) described above.

In yet another embodiment, provided a device configured to perform apheresis comprising one or more affinity columns comprising an affinity matrix and configured to substantially remove all types of cfDNA from a bodily fluid (e.g., blood, serum, plasma, cerebrospinal fluid (CSF), endometrial fluid, urine, saliva, lymph, glymph, tear fluid, sweat, synovial fluid, sputum) of a patient. In some embodiments, the device comprises two or more affinity columns in sequence. In some embodiments, the device further comprises a filtration cartridge. In some embodiments, the filtration cartridge has an inlet and an outlet. In some embodiments, one or more of the affinity columns has an inlet and an outlet.

In still yet another aspect is provided a device configured to perform apheresis comprising one or more affinity columns comprising an affinity matrix and configured to substantially remove all types of cfDNA from a perfusion solution that may be useful in the practice of various ex vivo and in vivo perfusion methods comprising perfusion of an organ (e.g., liver, lung, kidney or heart) and/or anatomical cavity (e.g., peritoneal or thoracic). In some embodiments, the device comprises two or more affinity columns in sequence. In some embodiments, the device further comprises a filtration cartridge. In some embodiments, the filtration cartridge has an inlet and an outlet. In some embodiments, one or more of the affinity columns has an inlet and an outlet.

In some embodiments, the device comprises two or more of the following affinity columns arranged in any sequence:

a) a column comprising a DNA binding protein (e.g., a histone or a high mobility group protein or DNABII [see, e.g., Buzzo et al., Cell, 2021, 184(23):P5740-5758.E17]) affinity matrix;

b) a column comprising a lectin (e.g., *Galanthus nivalis* Lectin (GNA), *Narcissus Pseudonarcissus* Lectin (NPA), Conconavalin A, phytohemagluttanin, or cyanovirin) affinity matrix;

c) a column comprising a DNA binding polymer (e.g., a cationic polymer such as, e.g., amino terminated ($—NH_2$) PAMAM dendrimer, hyper-branched poly-L-lysine or hyper-branched polyethylenimine) affinity matrix;

d) a column comprising an anti-DNA antibody affinity matrix;

e) a column comprising a DNA intercalating agent (e.g., polymyxin B, Hoechst 3342 or chloroquine) affinity matrix;

f) a column comprising an anti-nucleosome antibody affinity matrix (ANAM); and g) a column comprising an anti-histone antibody affinity matrix.

In some embodiments, the device comprises one of the following column combinations arranged in any order:

(a) (i) DNA intercalating agent Hoechst 33342 affinity column and (ii) anti-DNA antibody affinity column; or (b) (i) anti-nucleosome antibody affinity matrix (ANAM) column and (ii) anti-DNA antibody affinity column; or (c) (i) anti-nucleosome antibody affinity matrix (ANAM) column and (ii) polyamidoamine dendrimer affinity matrix (PDAM) column; or (d) (i) anti-nucleosome antibody affinity matrix (ANAM) column and (ii) hyper-branched poly-L-lysine affinity matrix (PLLAM) column; or (e) (i) anti-histone H2A antibody affinity column, (ii) lectin affinity column, and (iii) histone H1 affinity column or polyamidoamine dendrimer affinity matrix (PDAM) column or hyper-branched poly-L-lysine affinity matrix (PLLAM) column or DNA intercalating agent Hoechst 33342 affinity column.

In another aspect is provided an apheresis device comprising a filtration cartridge and one or more affinity columns having an inlet and an outlet, in which the device is capable of substantially capturing all types of cfDNA, including nucleosome bound cfDNA, exosome bound cfDNA and unbound cfDNA (including dsDNA, ssDNA and oligonucleotides), from a bodily fluid (e.g., blood, serum, plasma, cerebrospinal fluid (CSF), endometrial fluid, urine, saliva, lymph, glymph, tear fluid, sweat, synovial fluid, sputum) of a patient, or from a perfusion solution such as that which may be useful, for example, in the practice of various ex vivo and in vivo perfusion methods comprising perfusion of an organ and/or anatomical cavity.

In some embodiments, the device comprises two or more affinity columns in sequence. In some embodiments, the first affinity column in the sequence comprises a DNA binding polymer or a DNA intercalating agent.

As a variant of the affinity cartridge according to the present invention is "plasma-filter type" hollow-fiber affinity cartridge, one that does not allow blood cells to contact with affinity matrix capable of capturing cfDNA when plasma with non-cellular soluble and particulate cfDNA-components pass through the hollow fiber membrane pores to interact with the insoluble affinity matrix placed in the space behind such a membrane and returns freely through the same membrane to blood cell fraction.

This type of hollow fiber affinity cartridges is described, e.g., in U.S. Pat. Nos. 4,714,556, 4,787,974, 6,528,057 and US Pat. Appl. Pub. Nos. US 2014/0166578, US 2021/0030942, which are incorporated herein by reference in their entirety.

The particular variant of this type hollow-fiber cartridge was proposed and used for removing the undesired soluble (proteins, including oncoproteins) and particulate (microsomes) factors from cancer patient blood. (Marleau et al. Journal of Translational Medicine 2012, 10:13). As mentioned by authors, this device "consists of plasmapheresis cartridges that allows blood cells to pass through the hollow fibers while serum components <200 nm in size fit through the hollow fiber pores to interact with the affinity matrix. The matrices can be customized with one or more affinity substrates comprising monoclonal antibodies, lectins, aptamers or other affinity agents to specifically capture and remove tumor-derived exosomes and other soluble oncoproteins from the bloodstream using kidney dialysis or CRRT units".

To provide such hollow fiber affinity cartridges according to the present invention numerous types of hollow fiber plasma filter systems may be used. Hollow fiber plasma filter system is the most common type of membrane plasma-filter, consisting in a bundle of hollow fibers of 200-350 μm internal diameter, placed in a plastic and usually transparent housing. Their surface areas usually vary from 0.2 to 0.7 square meter. The walls of the hollow-fibers present porous membrane with pore size 0.2-0.7 μm. Blood circulates inside the fibers and plasma filtrate through walls (porous membrane) outside fiber lumen to extra-lumen space. The fibers are imbedded at each end in plastic mass that ensures separation between blood and plasma. During fabrication, the bundle ends must be carefully cut with a blade to reopen each fiber. Blood inlet and outlet are located in caps screwed on the housing, which are designed to distribute blood uniformly into all fibers, while plasma ports are located at each end of the housing, perpendicular to the fibers. See, for example, Michel Y. Jaffrin and Cecile Legallais, Biomedical Membrane Extracorporeal Devices, in Membrane Operations. Innovative Separations and Transformations. Edited by Enrico Drioli and Lidietta Giorno Copyright 2009 WILEY-VCH Verlag GmbH & Co. KGaA, Weinheim, ISBN: 978-3-527-32038-7.

To provide hollow fiber affinity cartridges, the extra-lumen space of conventional hollow fiber plasma-filter housing can be filled/packed with insoluble affinity matrix capable of capturing cfDNA, with the use of a syringe and an appropriate connector, then both plasma ports can be closed tightly with appropriate stopper. Alternatively, or additionally to packing hollow fiber plasma filter system with a matrix capable of capturing cfDNA, such matrix can be created directly on porous exterior portion (plasma compartment portion) of the membrane. This coupling of the peptide ligand on porous exterior portion of the plasma filter membrane is described, for example, in U.S. Pat. No. 4,787,974.

Thus, unlike a hollow fiber plasma filter, the plasma compartment of hollow fiber affinity cartridges is closed, filled with insoluble affinity matrix (and/or affinity ligand coupled with exterior i.e. plasma portions, the fiber walls), has no outlets and inlets for plasma flow and has communication only with the blood compartment through the membrane that separates them.

Regardless of hollow fiber system used, hollow fiber filters are required to allow passage of blood cells through the lumen of said hollow fiber, and allow cfDNA to diffuse to the extra-lumen space and to be captured by the affinity matrix.

Figure 13:
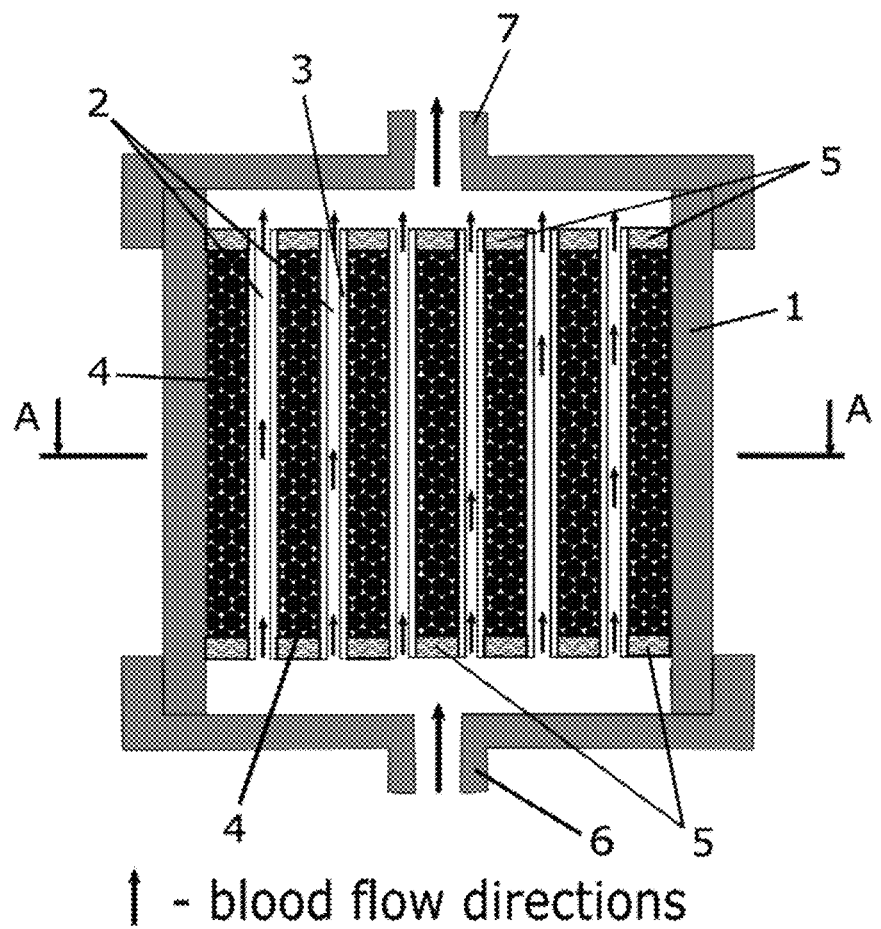
FIG. 13 shows the hollow fiber extracorporeal device according to the present invention, comprising a housing (1; 5; 6; 7); a hollow fiber filter disposed within said housing (2), said filter comprising a plurality of pores sized and dimensioned to not permit passage of cells (3), and insoluble affinity matrix capable of capturing cfDNA positioned inside the housing (4) and outside the hollow fiber in an extralumen space.
Figure 13:
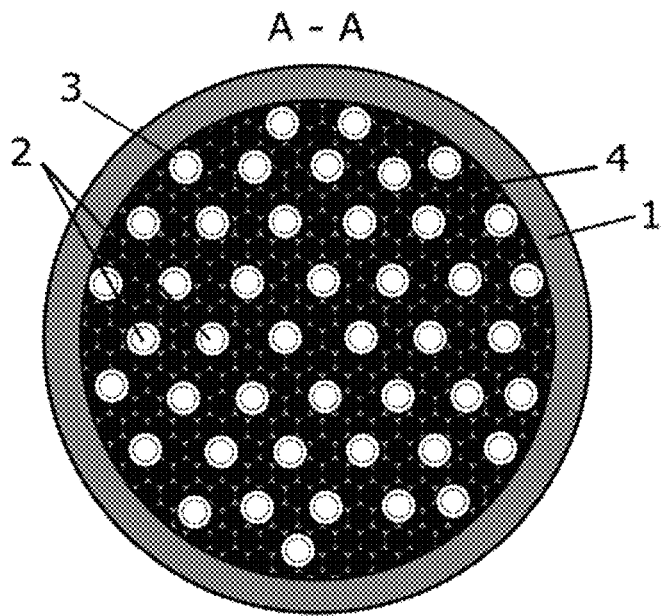

The scheme presented on FIG. 13, shows that the hollow fiber extracorporeal device, according to the present invention, comprises a cartridge housing 1. A bundle of hollow fibers 2 is disposed within the housing 1 and comprised of a plurality of hollow fibers having fiber walls (3) and the walls are the porous. The pores are sized 0.2-0.7 μm, preferably, 0.3-0.6 μm to not allow
    (1) blood cells to pass through the membrane and blood cells cannot enter the plasma compartments and blood cells cannot enter the plasma compartments that consists insoluble affinity matrix 4, capable of capturing cfDNA and
    (2) insoluble affinity matrix 4 to pass through the membrane into blood compartment.

The fibers are imbedded at each end in plastic mass 5 that ensures separation between blood and plasma compartment. Non-cellular portion of blood, i.e., plasma (containing the soluble and particulate cfDNA components less than cells) thus pass-through pores of said walls into an extra-lumen space and these soluble and particulate cfDNA components bind or removed by affinity matrix capable of capturing cfDNA into an extra-lumen space. The device has an inlet port 6 for entering the patient blood and an outlet port 7, wherein blood exits the device and then returns to the patient.

The "plasma-filter type" hollow-fiber affinity cartridge may be used for removing of cfDNA components from other cell-containing biofluids, for example, cerebrospinal fluids or lymph.

Thus, in some embodiments of the present invention, the device comprises a housing; a hollow fiber filter disposed within said housing; said filter comprising a plurality of pores sized and dimensioned to not permit passage of cells and insoluble affinity matrix capable of capturing cfDNA; and at least one insoluble affinity matrix capable of capturing cfDNA and positioned inside the housing and outside the hollow fiber in an extra-lumen space.

As a variant of the device, alternatively or additionally to insoluble affinity matrix placed to plasma compartment, DNA-binding ligand may be coupled with exterior (plasma) portion of hollow fiber membrane which is facing to extra-lumen space and thus ligand cannot contact blood cells. In this case the affinity matrix is presented by exterior part of the hollow fiber membrane (alternatively or additionally to insoluble particulate affinity matrix placed to plasma compartment).

In some embodiments, the device comprises a column comprising a histone affinity matrix upstream of, or before, a column comprising a lectin affinity matrix. In some embodiments, the device comprises a column comprising the histone affinity matrix upstream of, or before, a column comprising a lectin affinity matrix upstream of, or before, a column comprising a PAMAM affinity matrix. In some embodiments, the device comprises a column comprising an anti-DNA antibody affinity matrix upstream of, or before, a column comprising a Hoechst 3342 affinity matrix. In some embodiments, the device comprises a column comprising an anti-nucleosome antibody affinity matrix upstream of, or before, a column comprising a PAMAM affinity matrix.

In some embodiments, the apheresis device captures at least 30 mg of cfDNA per single apheresis procedure.

In some embodiments, the affinity column comprises an immobilized moiety effective to capture one or more of nucleosome-bound cfDNA, exosome-bound cfDNA and unbound cfDNA, including dsDNA, ssDNA and oligonucleotides. In some embodiments, the immobilized moiety is selected from the group consisting of DNA binding antibody, DNA intercalating agent, DNA binding protein, DNA binding polymer, lectin, anti-nucleosome antibody, and anti-histone antibody.

In some embodiments, the DNA binding protein is a histone. In some embodiments, the histone is a mammalian somatic histone.

In some embodiments, the histone is a linker histone such as, but not limited to, a histone H1 or H5.

In some embodiments, the linker histone is a histone H1 (e.g., H1.3).

In some embodiments, the linker histone is a histone H5.

In some embodiments, histone H1 may be selected from a histone H1.0, a histone H1.1, a histone H1.2, a histone H1.3, a histone H1.4, and a histone H1.5.

In some embodiments, the histone is a mammalian histone. In some embodiments, the mammalian histone is a human histone H1. In some embodiments, the histone H1 is a human histone H1.3.

In various embodiments, the histone may be selected from histone H1.0, H1.1, H1.2, H1.3, H1.4, H1.5 and, H1.7 (H1t Testis).

In some embodiments, the histone is a non-mammalian histone. In some embodiments, the non-mammalian histone is an avian histone. In some embodiments, the avian histone is chicken histone. In some embodiment, the avian histone is a goose histone H5.

In some embodiments, the non-mammalian histone is frog histone. In some embodiments, the frog histone is *Xenopus laevis* histone H5.

In some embodiments, the non-mammalian histone is a nematode histone. In some embodiments, the nematode histone is *Caenorhabditis elegans* histone H1.X.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone H1.3, (UniProt P16402 with additional M at the N-terminus)

(SEQ ID NO: 1)
MMSETAPLAPTIPAPAEKTPVKKKAKKAGATAGKRKASGPPVSELITKA

VAASKERSGVSLAALKKALAAAGYDVEKNNSRIKLGLKSLVSKGTLVQT

KGTGASGSFKLNKKAASGEGKPKAKKAGAAKPRKPAGAAKKPKKVAGAA

TPKKSIKKTPKKVKKPATAAGTKKVAKSAKKVKTPQPKKAAKSPAKAKA

PKPKAAKPKSGKPKVTKAKKAAPKKK.

In a specific embodiment, the histone comprises an amino acid sequence which is at least 70% identical (e.g., at least 80% identical, at least 85% identical, at least 90% identical, at least 95% identical, at least 98% identical, at least 99% identical) to the sequence of the human histone H1.0

(SEQ ID NO: 2)
TENSTSAPAAKPKRAKASKKSTDHPKYSDMIVAAIQAEKNRAGSSRQSI

QKYIKSHYKVGENADSQIKLSIKRLVTTGVLKQTKGVGASGSFRLAKSD

EPKKSVAFKKTKKEIKKVATPKKASKPKKAASKAPTKKPKATPVKKAKK

KLAATPKKAKKPKTVKAKPVKASKPKKAKPVKPKAKSSAKRAGKKK.

In a specific embodiment, the histone comprises an amino acid sequence which is at least 70% identical (e.g., at least 80% identical, at least 85% identical, at least 90% identical, at least 95% identical, at least 98% identical, at least 99% identical) to the sequence of histone H5 of *Anser anser* (Western greylag goose), UniProt P02258

(SEQ ID NO: 3)
TDSPIPAPAPAAKPKRARAPRKPASHPTYSEMIAAAIRADKSRGGSSRQ

SIQKYVKSHYKVGQHADLQIKLAIRRLLTTGVLKQTKGVGASGSFRLAK

GDKAKRSPAGRKKKKAARKSTSPKKAARPRKARSPAKKPKAAARKARK

KSRASPKKAKKPKTVKAKSLKTSKPKKARRSKPRAKSGARKSPKKK.

In another specific embodiment, the histone comprises an amino acid sequence which is at least 70% identical (e.g., at least 80% identical, at least 85% identical, at least 90% identical, at least 95% identical, at least 98% identical, at least 99% identical) to the sequence of histone H5 of *Gallus gallus* UniProt P02259

(SEQ ID NO: 4)
MTESLVLSPAPAKPKRVKASRRSASHPTYSEMIAAAIRAEKSRGGSSRQ

SIQKYIKSHYKVGHNADLQIKLSIRRLLAAGVLKQTKGVGASGSFRLAK

SDKAKRSPGKKKKAVRRSTSPKKAARPRKARSPAKKPKATARKARKKSR

ASPKKAKKPKTVKAKSRKASKAKKVKRSKPRAKSGARKSPKKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone H1.0, UniProt P07305

(SEQ ID NO: 5)
MTENSTSAPAAKPKRAKASKKSTDHPKYSDMIVAAIQAEKNRAGSSRQS

IQKYIKSHYKVGENADSQIKLSIKRLVTTGVLKQTKGVGASGSFRLAKS

DEPKKSVAFKKTKKEIKKVATPKKASKPKKAASKAPTKKPKATPVKKAK

KKLAATPKKAKKPKTVKAKPVKASKPKKAKPVKPKAKSSAKRAGKKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone H1.1, UniProt Q02539

(SEQ ID NO: 6)
MSETVPPAPAASAAPEKPLAGKKAKKPAKAAAASKKKPAGPSVSELTVQ

AASSSKERGGVSLAALKKALAAAGYDVEKNNSRIKLGIKSLVSKGTLVQ

TKGTGASGSFKLNKKASSVETKPGASKVATKTKATGASKKLKKATGASK

KSVKTPKKAKKPAATRKSSKNPKKPKTVKPKKVAKSPAKAKAVKPKAAK

ARVTKPKTAKPKKAAPKKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone H1.2, UniProt P16403

(SEQ ID NO: 7)
MSETAPAAPAAAPPAEKAPVKKKAAKKAGGTPRKASGPPVSELITKAVA

ASKERSGVSLAALKKALAAAGYDVEKNNSRIKLGLKSLVSKGTLVQTKG

TGASGSFKLNKKAASGEAKPKVKKAGGTKPKKPVGAAKKPKKAAGGATP

KKSAKKTPKKAKKPAAATVTKKVAKSPKKAKVAKPKKAAKSAAKAVKPK

AAKPKVVKPKKAAPKKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone H1.4, UniProt P10412

(SEQ ID NO: 8)
MSETAPAAPAAPAPAEKTPVKKKARKSAGAAKRKASGPPVSELITKAVA

ASKERSGVSLAALKKALAAAGYDVEKNNSRIKLGLKSLVSKGTLVQTKG

TGASGSFKLNKKAASGEAKPKAKKAGAAKAKKPAGAAKKPKKATGAATP

KKSAKKTPKKAKKPAAAAGAKKAKSPKKAKAAKPKKAPKSPAKAKAVKP

KAAKPKTAKPKAAKPKKAAAKKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone H1.5, UniProt Q14529

(SEQ ID NO: 9)
MSETAPAETATPAPVEKSPAKKKATKKAAGAGAAKRKATGPPVSELITK

AVAASKERNGLSLAALKKALAAGGYDVEKNNSRIKLGLKSLVSKGTLVQ

TKGTGASGSFKLNKKAASGEAKPKAKKAGAAKAKKPAGATPKKAKKAAG

AKKAVKKTPKKAKKPAAAGVKKVAKSPKKAKAAAKPKKATKSPAKPKAV

KPKAAKPKAAKPKAAKPKAAKAKKAAAKKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone H1.7, UniProt P22492

(SEQ ID NO: 10)
MSETVPAASASAGVAAMEKLPTKKRGRKPAGLISASRKVPNLSVSKLIT

EALSVSQERVGMSLVALKKALAAAGYDVEKNNSRIKLSLKSLVNKGILV

QTRGTGASGSFKLSKKVIPKSTRSKAKKSVSAKTKKLVLSRDSKSPKTA

KTNKRAKKPRATTPKTVRSGRKAKGAKGKQQQKSPVKARASKSKLTQHH

EVNVRKATSKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of human histone human recombinant H1.0 histone, for example, as may be commercially available, e.g., formulated in a storage buffer at a concentration of 1 mg/ml (Cat #M2501S; New England Bio Labs, Ipswich, MA)

(SEQ ID NO: 11)
TENSTSAPAAKPKRAKASKKSTDHPKYSDMIVAAIQAEKNRAGSSRQSI

QKYIKSHYKVGENADSQIKLSIKRLVTTGVLKQTKGVGASGSFRLAKSD

EPKKSVAFKKTKKEIKKVATPKKASKPKKAASKAPTKKPKATPVKKAKK

KLAATPKKAKKPKTVKAKPVKASKPKKAKPVKPKAKSSAKRAGKKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of recombinant histone H1.X of *Caenorhabditis elegans*, free-living transparent nematode (see, e.g., Jedrusik et al., J Cell Sci. 2002 Jul. 15; 115(Pt 14):2881-91, the contents of which is herein incorporated by reference in its entirety for all purposes)

(SEQ ID NO: 12)
MSETVPAASASAGVAAMEKLPTKKRGRKPAGLISASRKVPNLSVSKLIT

EALSVSQERVGMSLVALKKALAAAGYDVEKNNSRIKLSLKSLVNKGILV

QTRGTGASGSFKLSKKVIPKSTRSKAKKSVSAKTKKLVLSRDSKSPKTA

KTNKRAKKPRATTPKTVRSGRKAKGAKGKQQQKSPVKARASKSKLTQHH

EVNVRKATSKK.

In a specific embodiment, the histone comprises an amino acid sequence which is at least 70% identical (e.g., at least 80% identical, at least 85% identical, at least 90% identical, at least 95% identical, at least 98% identical, or at least 99% identical) to the sequence of recombinant human histone H1.4 (HIST1H1E), yeast produced, for example, as may be commercially available, e.g., lyophilized from Tris/PBS-based buffer, 6% Trehalose, pH 8.0 Tag-free <85%, and Yeast (Cat #CSB-YP010380HU; Cusabio, Wuhan, China)

(SEQ ID NO: 13)
SETAPAAPAAPAPAEKTPVKKKARKSAGAAKRKASGPPVSELITKAVAA

SKERSGVSLAALKKALAAAGYDVEKNNSRIKLGLKSLVSKGTLVQTKGT

GASGSFKLNKKAASGEAKPKAKKAGAAKAKKPAGAAKKPKKATGAATPK

KSAKKTPKKAKKPAAAAGAKKAKSPKKAKAAKPKKAPKSPAKAKAVKPK

AAKPKTAKPKAAKPKKAAAKKK.

In some embodiments, the histone may comprise a bis-met histone, for example, as described in Int. Pat. Appl. Pub. No. WO2008/122434 and U.S. Pat. Appl. Pub. No. 2011/034370, the disclosure of which is herein incorporated by reference in its entirety for all purposes. In some embodiments, a nucleic acid molecule which encodes a polypeptide comprising a bis-met histone useful in the practice of the present disclosure may comprise two methionine residues, e.g., as the first and second N-terminal amino acid residues, which may be linked such as via a peptide bond to a mature eukaryotic histone. While not wishing to be bound by theory, incorporation of a methionine residue(s) at the N-terminus of a nascent polypeptide may comprise a universal translation initiation signal useful for prokaryotes and eukaryotes. Processing of N-terminal methionine may contribute to protein stability and support various protein functions.

In some embodiments, the DNA binding protein is a high mobility group (HMG) protein such as, but not limited to, a high mobility group box protein 1 (hmgb1). High mobility group (HMG) members are a class of non-histone DNA binding proteins that bind DNA and regulate chromatin structural organization and various DNA-associated processes. The high mobility group box 1 (hmgb1) protein belongs to the family of HMG proteins. Without wishing to be bound by theory, similar to histones, the hmgb-1 protein may interact with internucleosomal (linker) DNA. Hmgb-1 may participate in such processes as, for example, the regulation of DNA repair, transcription, replication, and recombination. In certain aspects, hmgb1 may act as DNA-chaperone, and may recruit the chromatin remodeling complex to nucleosome, as well as may modulate the binding of transcription factors to DNA. As a non-limiting example, binding of hmgb1 to linker DNA may be associated with bending of the double helix at the binding site, the binding of the protein to DNA thereby resulting in changes of the double helix geometry that may, for example, be in the vicinity of the binding site. Without wishing to be bound by theory, proteins from the HMGB family may be characterized by pronounces affinity and selectivity to DNA regions with various structural abnormalities such as, but not limited to, bends and crossovers 4H DNA, as well as single- and double-stranded breaks. Together with histone H1, hmgb1 may modulate the integrity of chromatin as well as its packing density. The action of extra-nuclear protein hmgb1 is diverse and may include, without limitation, participation in the transmission of immune response signal, tissue inflammation, and various aspects of the tumor microenvironment.

On average, one hmgb1 molecule may be observed per 10-15 nucleosomes. Hmgb1 may possess a half-life that is more than two generations of cells, which may be in alignment with the half-life observed for histones. Further, hmgb1 may be localized to both nucleus and cytoplasm, its representation within each of these compartments dependent on tissue type, redox state of hmgb1, and the stage of cell differentiation. Hmgb1 may comprise two structurally conserved DNA-binding domains (HMGB-domains A and B), and may be susceptible to modifications (e.g., post-translational modifications), including, for example, phosphorylation, methylation, acetylation, glycosylation, and poly-ADP ribosylation, which are thought to play a role in its interactions with DNA and other proteins; nucleus-to-cytoplasm transport; and extracellular release. In various embodiments, it is contemplated that any of the hmgb1 proteins which may be used in accordance with the invention may comprise any number of such modifications, or combination thereof.

In some embodiments, the DNA binding protein may be presented as its conjugate with a polymer (e.g., with a polypeptide, polysaccharide or with a non-biodegradable polymer). The polymer may be a cationic polymer, e.g., poly(ethylenimine), poly(amidoamine) (PAMAM), poly(aspartamide), polypeptoids (e.g., for forming "spiderweb"-like branches for core condensation), a charge-functionalized polyester, a cationic polysaccharide, an acetylated amino sugar, chitosan, or a cationic polymer that comprises any combination thereof (e.g., in linear or branched forms). The cationic polymer may be covalently associated with a DNA binding protein. The nanoparticle may also comprise a cationic polymer composition that comprises a DNA binding protein and another cationic polymer (such as those described above).

In some embodiments, the DNA binding protein disclosed herein may be presented as its conjugate with a high-molecular weight organic carrier (e.g., a dendrimer) or with particle carrier (e.g., with nanoparticles such as, for example, magnetic nanoparticles [which, in some embodiments, may consist of two components, a magnetic material, often iron, nickel and cobalt, and a chemical or biochemical component that has functionality]).

In certain embodiments, the DNA binding protein is conjugated to a dendrimer. The dendrimer may be a polyamidoamine (PAMAM) dendrimer, such as that described in International Patent Publication No. WO2019/053243, incorporated by reference herein in its entirety. The DNA binding protein may be conjugated to a polyamidoamine (PAMAM) dendrimer affinity matrix (PDAM) or polypropyleneimine (PPI) dendrimer affinity matrix. See, e.g., Kaur et al., J Nanopart Res., 2016, 18: 146. Dendrimers are unique synthetic polymers of nanometer dimensions with a highly branched structure and globular shape. Among dendrimers, polyamidoamine (PAMAM) have received most attention as potential transfection agents for gene delivery, because these macro molecules bind DNA at physiological pH. PAMAM dendrimers consist of an alkyl-diamine core and tertiary amine branches. They are available in ten generations with 5 different core types and 10 functional surface groups. DNA and polyamidamine (PAMAM) dendrimers form complexes on the basis of the electrostatic interactions between negatively charged phosphate groups of the nucleic acid and protonated (positively charged) amino groups of the polymers. Formation of high molecular weight and high-density complexes depend mainly on the DNA concentration, with enhancement by increasing the dendrimer-DNA charge ratio. (Shcharbin, D. et al., Practical Guide to Studying Dendrimers. Book, iSmithers Rapra Publishing: Shawbury, Shrewsbury, Shropshire, U K, 2010. 120 p. ISBN: 978-1-84735-444-0.)

In certain embodiments, the DNA binding protein is conjugated to a nanoparticle. The nanoparticles may be a phosphoramidite nanoparticle. In some embodiments, the nanoparticle is magnetic. The magnetic nanoparticle may comprise a single magnetic core and an outer shell, wherein the outer shell covers the magnetic core. The magnetic particle may comprise a metal oxide, e.g., $Fe_3O_4$. In some embodiments, the magnetic particle has a maximum diameter of 100 nm to 1000 nm. In some embodiments, the magnetic particle has a maximum diameter of 300 nm to 700 nm. In some embodiments, the magnetic particle has a maximum diameter of 400 nm to 600 nm.

In some embodiments, the nanoparticle has a maximum diameter of less than 1 µm, such as less than 900 nm, less than 800 nm, less than 700 nm, less than 600 nm, less than 500 nm, less than 400 nm, less than 300 nm, or less than 200 nm. In various embodiments, the magnetic nanoparticle has a maximum diameter of 100 nm to 1000 nm, such as 100 nm to 900 nm, 100 nm to 800 nm, 100 nm to 700 nm, 100 nm to 600 nm, 100 nm to 500 nm, 100 nm to 400 nm, 100 nm to 300 nm, 100 nm to 200 nm, 200 nm to 1000 nm, 200 nm to 900 nm, 200 nm to 800 nm, 200 nm to 700 nm, 200 nm to 600 nm, 200 nm to 500 nm, 200 nm to 400 nm, 200 nm to 300 nm, 300 nm to 1000 nm, 300 nm to 900 nm, 300 nm to 800 nm, 300 nm to 700 nm, 300 nm to 600 nm, 300 nm to 500 nm, 300 nm to 400 nm, 400 nm to 1000 nm, 400 nm to 900 nm, 400 nm to 800 nm, 400 nm to 700 nm, 400 nm to 600 nm, 400 nm to 500 nm, 500 nm to 1000 nm, 500 nm to 900 nm, 500 nm to 800 nm, 500 nm to 700 nm, 500 nm to 600 nm, 600 nm to 1000 nm, 600 nm to 900 nm, 600 nm to 800 nm, 600 nm to 700 nm, 700 nm to 1000 nm, 700 nm to 900 nm, 700 nm to 800 nm, 800 nm to 1000 nm, 800 nm to 900 nm, or 900 nm to 1000 nm. In certain embodiments, the magnetic core has a maximum diameter of about 900 nm. In certain embodiments, the magnetic core has a maximum diameter of about 800 nm. In certain embodiments, the magnetic core has a maximum diameter of about 700 nm. In certain embodiments, the magnetic core has a maximum diameter of about 600 nm. In certain embodiments, the magnetic core has a maximum diameter of about 500 nm. In certain embodiments, the magnetic core has a maximum diameter of about 400 nm. In certain embodiments, the magnetic core has a maximum diameter of about 300 nm. In certain embodiments, the magnetic core has a maximum diameter of about 200 nm.

In some embodiments, the nanoparticle comprises a cationic polymer, e.g., poly(ethylenimine), poly(amidoamine) (PAMAM), poly(aspartamide), polypeptoids (e.g., for forming "spiderweb"-like branches for core condensation), a charge-functionalized polyester, a cationic polysaccharide, an acetylated amino sugar, chitosan, or a cationic polymer that comprises any combination thereof (e.g., in linear or branched forms). The cationic polymer may be covalently associated with a DNA binding protein. The nanoparticle may also comprise a cationic polymer composition that comprises a DNA binding protein and another cationic polymer (such as those described above).

In various embodiments of the above, the DNA binding protein may be conjugated to a matrix or to beads. The matrix or beads can be spun down or isolated so as to enrich for the DNA binding protein. In certain embodiments, the matrix is a cellulose matrix. In certain embodiments, the matrix is a magnetic bead. In some embodiments, the DNA binding protein is bound to an affinity matrix.

In some embodiments, the DNA binding polymer is a cationic polymer. In some embodiments, the cationic polymer is poly-L-lysine. In some embodiments, the poly-L-lysine is hyper-branched poly-L-lysine. In some embodiments, the cationic polymer is polyethylenimine. In some embodiments, the polyethylenimine is hyper-branched polyethylenimine. In some embodiments, the cationic polymer is amino terminated ($-NH_2$) polyamidoamine (PAMAM) dendrimer.

In some embodiments of the above, the apheresis device comprises two sequential affinity columns, in which one column captures nucleosome bound DNA and exosome-bound DNA and another column captures unbound cfDNA including dsDNA, ssDNA and oligonucleotides. In some embodiments, the immobilized moiety is selected from the group consisting of a combination of two or more of the following moieties: DNA binding antibody, DNA intercalating agent, DNA binding protein, DNA binding polymer, lectin, anti-nucleosome antibody, or anti-histone antibody.

In some non-limiting embodiments of the above aspects, the bodily fluid is selected from blood, serum, plasma, lymph, urine, cerebrospinal fluid (CSF), endometrial fluid, saliva, tear fluid, synovial fluid, and sputum.

In another aspect is provided a method of reducing the level of cfDNA in a bodily fluid of a patient. The method comprises (a) performing an apheresis procedure comprising diverting the bodily fluid from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides).

In some embodiments, the method may be useful to reduce the level of cfDNA in a bodily fluid of a patient who has received or is due to receive an organ transplant.

In some embodiments, the method may be useful to reduce the level of cfDNA in a bodily fluid of a patient who has been deemed an organ donor.

In some embodiments, the method may be useful to reduce the level of cfDNA in a bodily fluid of a patient who has received or is due to receive an adoptive cell therapy. In some embodiments, the patient is a cancer patient. As a non-limiting example, the adoptive cell therapy may be a chimeric antigen receptor T cell (CAR-T cell) therapy. As another non-limiting example, the adoptive cell therapy may be a chimeric antigen receptor natural killer cell (CAR-NK cell) therapy. Without wishing to be bound by theory, chimeric antigen receptors (CARs) are hybrid molecules comprising an antigen-targeting moiety, e.g., a single-chain variable fragment (scFv), followed by a linker, transmembrane (TM) domain, and any number of various endodomains that may participate in lymphocyte activation. First generation CARs may comprise the endodomain of CD3-ζ alone, requisite for a first signal of lymphocyte activation. Second and third generation CARs also have one or more co-stimulatory endodomains, respectively, for example, and without limitation, 4-1BB and CD28. Such endodomains provide a second signal for lymphocyte activation. 30% of patients receiving CAR-T cell treatment may require intensive care unit admission within 4 days of CAR-T cell infusion for the treatment of, e.g., cytokine release syndrome (CRS) and/or immune effector cell-associated neurotoxicity syndrome (ICANS). The mortality rate in such instances may be as high as 23%. Macrophage activation syndrome (MAS) has been recognized as another cause for patient mortality in clinical trials of CAR-T cell therapy of solid tumors. The best overall response rate varies somewhere between 50% to 80% for hematological malignancies and 8-15% for solid tumors In certain embodiments, the method to reduce the level of cfDNA in a bodily fluid of a patient who has received CAR-T therapy disclosed herein may improve the efficacy of the CAR-T cell therapy and/or ameliorate associated limiting toxicities such as, but not limited to, cytokine release syndrome (CRS), immune effector cell-associated neurotoxicity syndrome (ICANS), and/or macrophage activation syndrome (MAS).

In some embodiments, substantial removal of all types of cfDNA, including nucleosome-bound cfDNA, exosome-bound cfDNA and unbound cfDNA (including double stranded DNA [dsDNA], single stranded DNA [ssDNA] and oligonucleotides from a bodily fluid of a patient who has received CAR-T cell therapy may comprise continuous removal of cfDNA, e.g., cfDNA in the form of neutrophil NETs, over a period of time, e.g., 1 to 20 days. In some embodiments, the substantial removal of all types of cfDNA from a bodily fluid of a patient who has received CAR-T cell therapy may comprise continuous removal of the cfDNA over a period of up to 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, or 20 or more days. In some embodiments, the substantial removal of all types of cfDNA from a bodily fluid of a patient who has received CAR-T cell therapy may comprise continuous removal of the cfDNA over a period of 7 days.

In some embodiments, substantial removal of all types of cfDNA, including nucleosome-bound cfDNA, exosome-bound cfDNA and unbound cfDNA (including double stranded DNA [dsDNA], single stranded DNA [ssDNA] and oligonucleotides from a bodily fluid of a patient who has received CAR-T cell therapy may ameliorate systemic immunosuppression.

In some embodiments, substantial removal of all types of cfDNA, including nucleosome-bound cfDNA, exosome-bound cfDNA and unbound cfDNA (including double stranded DNA [dsDNA], single stranded DNA [ssDNA] and oligonucleotides from a bodily fluid of a patient who has received CAR-T cell therapy may reduce recruitment of tumor-associated macrophages (TAMs).

In some embodiments, substantial removal of all types of cfDNA, including nucleosome-bound cfDNA, exosome-bound cfDNA and unbound cfDNA (including double stranded DNA [dsDNA], single stranded DNA [ssDNA] and oligonucleotides from a bodily fluid of a patient who has received CAR-T cell therapy may reduce recruitment of tumor-infiltrating neutrophils (TINs).

In some embodiments, substantial removal of all types of cfDNA, including nucleosome-bound cfDNA, exosome-bound cfDNA and unbound cfDNA (including double stranded DNA [dsDNA], single stranded DNA [ssDNA] and oligonucleotides from a bodily fluid of a patient who has received CAR-T cell therapy may enhance cytotoxicity and/or recruitment of immune effector cells.

In some embodiments, the method is effective to treat one or more diseases selected from multiorgan failure, a neurodegenerative disease (e.g., Alzheimer's disease, Parkinson's disease, Huntington's disease, Amyotrophic Lateral Sclerosis (ALS), Friedreich ataxia, Lewy body disease), cancer, sepsis, COVID-19, septic kidney injury, irradiation induced toxicity (e.g., acute radiation syndrome), and chemotherapy-related toxicity.

In any of the embodiments or aspects described herein, the cancer may be, for example, but without limitation a cancer of the breast, colon, lung, prostate, kidney, pancreas, brain, bones, ovary, testes, or a lymphatic organ.

In some embodiments, the patient has a disease selected from the group consisting of cancer, metastatic cancer, acute organ failure, organ infarct, hemorrhagic stroke, graft-versus-host-disease (GVHD), graft rejection, delayed graft function, sepsis, COVID-19, systemic inflammatory response syndrome (SIRS), multiple organ dysfunction syndrome (MODS), irradiation induced toxicity (e.g., acute radiation syndrome), chemotherapy-related toxicity, traumatic injury, pro-inflammatory status in aged individuals, diabetes, atherosclerosis, neurodegenerative disease, autoimmune disease, eclampsia, infertility, coagulation disorder, and infection.

In some embodiments, the method is effective to treat a disorder in a patient, wherein the disorder is selected from cancer, metastatic cancer, acute organ failure, organ infarct (including myocardial infarction and ischemic stroke, hemorrhagic stroke, autoimmune disorders, graft-versus-host-disease (GVHD), graft rejection, delayed graft function, sepsis, COVID-19, systemic inflammatory response syndrome (SIRS), multiple organ dysfunction syndrome (MODS), graft-versus-host-disease (GVHD), traumatic injury, proinflammatory status in aged individuals, diabetes, atherosclerosis, neurodegenerative disease, autoimmune disease, eclampsia, infertility, coagulation disorder, pregnancy-associated complications and infection. In some embodiments, the patient is in need of treatment of the disorder.

In various embodiments, the patient is a human. In various embodiments, the subject is a human. The subject can be a mammal, e.g., a farm animal (e.g., a horse, a pig, a goat), or a pet. The mammal can be an adult or a child.

In yet another embodiment provided herein is a method for treating multiple organ dysfunction syndrome (MODS) in a patient. The method comprises (a) performing an apheresis procedure comprising diverting a bodily fluid (e.g., blood or plasma, or CSF) from the patient into an apheresis device to produce purified bodily fluid; and (b) returning the purified bodily fluid with reduced levels of the cfDNA to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of MODS.

In another embodiment, provided herein is a method for treating a neurodegenerative disease in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of the neurodegenerative disease.

In another embodiment, provided herein is a method for treating Alzheimer's disease in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of Alzheimer's disease.

In another embodiment, provided herein is a method for treating cancer in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of cancer.

In another embodiment, provided herein is a method for treating sepsis in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure reduces the level of substantially all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of sepsis.

In another embodiment, provided herein is a method for treating a kidney injury in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of the kidney injury.

In another embodiment, provided herein is a method for treating chemotherapy-related toxicity in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of chemotherapy-related toxicity.

In another embodiment, provided herein is a method for treating irradiation induced toxicity (e.g., acute radiation syndrome) in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of irradiation induced toxicity.

In another embodiment, provided herein is a method for treating COVID-19 in a patient. The method comprises (a) performing an apheresis procedure comprising diverting a bodily fluid (e.g., blood or plasma, or CSF) from the patient into an apheresis device to produce purified bodily fluid with reduced levels of cfDNA; and (b) returning the purified bodily fluid to the patient. The apheresis procedure substantially reduces the level of all types of cfDNA in the patient's bodily fluid, including nucleosome-bound cfDNA, exosome-bound cfDNA and unbound cfDNA (including dsDNA, ssDNA and oligonucleotides). In some embodiments, the patient is in need of treatment of irradiation induced toxicity.

In various embodiments of any of the treatment methods disclosed herein, the method may comprise administering a therapeutic compound or a treatment to the patient to treat the disease or the disorder. In some embodiments, the therapeutic compound or treatment reduces the level of the cfDNA in the patient. In some embodiments, the reduction of the level of cfDNA is performed by administering an enzyme having deoxyribonuclease (DNase) activity. Non-limiting examples of such enzymes having DNase activity include, e.g., DNase I, DNase X, DNase γ, DNase1L1, DNase1L2, DNase 1L3, DNase II, DNase IIα, DNase IIβ, Caspase-activated DNase (CAD), Endonuclease G (EN-DOG), Granzyme B (GZMB), phosphodiesterase I, lactoferrin, acetylcholinesterase, or mutants or derivatives thereof. In one embodiment, wherein the cfDNA is present in the blood, the reduction of the level of the cfDNA is performed by an apheresis procedure. In another embodiment, wherein the cfDNA is present in the cerebrospinal fluid, the reduction of the level of the cfDNA is performed by an apheresis procedure. Non-limiting examples of the diseases treatable by the method of the invention include, e.g., neurodegenerative diseases, cancers, chemotherapy-related toxicities, irradiation induced toxicities, organ failures, organ injuries, organ infarcts, ischemia, acute vascular events, a stroke, graft-versus-host-disease (GVHD), graft rejections, sepsis, COVID-19, systemic inflammatory response syndrome (SIRS), cytokine releasing syndrome (CRS), multiple organ dysfunction syndrome (MODS), traumatic injuries, aging, diabetes, atherosclerosis, autoimmune disorders, eclampsia, preeclampsia, infertility, pregnancy-associated complications, coagulation disorders, asphyxia, drug intoxication, poisoning, and infections. In some embodiments, the disease is a cancer.

In some embodiments of any of the above methods, the blood is diverted from the portal vein of the patient.

In some embodiments of any of the above methods, the CSF is diverted from the subarachnoid space of the patient, e.g., the cranial subarachnoid space and/or the spinal sub arachnoid space. In some embodiments of any of the above methods, the CSF is diverted from the ventricles of the brain of the patient, e.g., the lateral ventricles, third ventricle, and/or fourth ventricle. In some embodiments, the CSF is diverted from the central canal of the spinal cord of the patient.

In some embodiments, the purified bodily fluid or the perfusion solution disclosed herein has reduced levels of cfDNA as compared to the levels of cfDNA prior to the apheresis procedure.

In some embodiments, the purified bodily fluid or perfusion solution disclosed herein has reduced levels of all of nucleosome-bound cfDNA, exosome-bound cfDNA and unbound cfDNA, including dsDNA, ssDNA and oligonucleotides. In some embodiments, the method further comprises periodically monitoring the level of the circulating cfDNA in the patient's bodily fluid or the perfusion solution, and continuing the apheresis procedure to reduce the circulating level of cfDNA by at least 25% before concluding the apheresis procedure. In some embodiments, the method further comprises periodically monitoring the level of the circulating cfDNA in the patient's bodily fluid or the perfusion solution, and continuing the apheresis procedure on the patient to reduce the circulating levels of cfDNA by at least 50% before concluding the apheresis procedure. In some embodiments, the method further comprises periodically monitoring the level of the circulating cfDNA in the patient's bodily fluid or the perfusion solution, and continuing the apheresis procedure on the patient to reduce the levels of circulating cfDNA by at least 75% before concluding the apheresis procedure.

In some embodiments of any of the above, at least 30 mg of cfDNA is removed from the bodily fluid of the patient or the perfusion solution during one or several sequential apheresis procedures.

In some embodiments of the above, the method steps are repeated, or undertaken on a schedule. The method steps may be conducted twice a day, every day, every two days, every three days, every four days, every five days, every six days, every week, every eight days, every nine days, every 10 days, every 11 days, every 12 days, etc. Samples of bodily fluid, for example, may be taken from the patient and tested for levels of cfDNA to assess the frequency of conducting the methods of treatment.

In another aspect is provided a method of reducing the level of cfDNA in an ex vivo perfused organ, e.g., an organ from a human subject. The method comprises (a) performing an apheresis procedure comprising diverting a perfusion solution from an ex vivo perfused organ into an apheresis device to produce a purified perfusion solution with reduced levels of cfDNA; and (b) returning the purified perfusion solution to the ex vivo perfused organ. The apheresis procedure substantially reduces the level of all types of cfDNA in the perfusion solution, including nucleosome-bound cfDNA, exosome-bound cfDNA and unbound cfDNA (including dsDNA, ssDNA and oligonucleotides).

In various embodiments, the ex vivo perfused organ may be selected from, for example, liver, lung, kidney or heart. In some embodiments, the ex vivo perfused organ is liver. In some embodiments, the ex vivo perfused organ is lung. In some embodiments, the ex vivo perfused organ is kidney. In some embodiments, the ex vivo perfused organ is heart.

Other non-limiting examples of ex vivo organs that may be used in accordance with the invention include pancreas and intestine.

In some embodiments, the ex vivo perfused organ may be from a subject that is human. In some embodiments, the ex vivo perfused organ may be from a subject that is a veterinary animal such as, but not limited to, a pig or a cow.

In various embodiments, the substantial removal of all types of cfDNA, including nucleosome-bound cfDNA, exosome-bound cfDNA and unbound cfDNA (including double stranded DNA [dsDNA], single stranded DNA [ssDNA] and oligonucleotides) from a perfusion solution useful in the practice of ex vivo perfusion of an organ disclosed herein may be useful for improving the quality and/or survival of organs (e.g., donated organs), and reduce unfavorable transplantation outcomes.

In various embodiments of any of the perfusion methods disclosed herein, the perfusion solution may comprise blood, e.g., whole blood or leukodepleted blood. In various embodiments of the any of the perfusion methods disclosed herein, the perfusion solution may consist essentially of whole blood or leukodepleted blood. In various embodiments of any of the perfusion methods disclosed herein, the perfusion solution may consist of whole blood or leukodepleted blood. The composition of perfusion solution might be customized depending on specific organ requirements. For example, a perfusion solution may comprise leukocyte reduced red blood cells in combination with volume expanders (e.g., dextran, gelatine or albumin), salts (e.g., magnesium sulfate, potassium chloride, sodium chloride, monopotassium phosphate, sodium hydrocarbonate, calcium gluconate), energetic and structural substrates (e.g., glucose, aminoacids, vitamins), hormones (e.g., methylprednisolone, insulin), organ-specific additives (sodium taurocholate, epinephrine), heparin and anti-infectives (e.g., cefazoline, ciprofloxacin, voriconazole).

In yet another embodiment, provided herein is a method of reducing the level of cfDNA in an in vivo perfused anatomical cavity (e.g., peritoneal or thoracic). The method comprises (a) performing an apheresis procedure comprising diverting a perfusion solution from an in vivo perfused anatomical cavity into an apheresis device to produce a purified perfusion solution with reduced levels of cfDNA; and (b) returning the purified perfusion solution to the in vivo perfused anatomical cavity. The apheresis procedure substantially reduces the level of all types of cfDNA in the perfusion solution, including nucleosome-bound cfDNA, exosome-bound cfDNA and unbound cfDNA (including dsDNA, ssDNA and oligonucleotides).

In various embodiments, the in vivo perfused anatomical cavity may be peritoneal. In various embodiments, the in vivo perfused anatomical cavity may be thoracic. Other non-limiting examples of in vivo anatomical cavities that may be used in accordance with the invention include cranial, vertebral, abdominal, pelvic, and abdominopelvic cavities.

In some embodiments, the in vivo anatomical cavity may be that of a subject who is a human subject.

In certain embodiments, any of various perfusion solution(s) and/or method(s) comprising such perfusion solutions of the disclosure may comprise chemotherapy, for example, without limitation, hyperthermic chemotherapy. By way of a non-limiting example, the hyperthermic chemotherapy may comprise hyperthermic intraperitoneal chemotherapy. By way of another non-limiting example, the hyperthermic chemotherapy may comprise hyperthermic intraperitoneal chemotherapy or hyperthermic intrathoracic chemotherapy.

Arrangement of affinity columns in sequence can allow capturing of substantially all types of cfDNA, including nucleosome-bound cfDNA, exosome-bound cfDNA and unbound cfDNA (including dsDNA, ssDNA and oligonucleotides), from bodily fluid (e.g., blood or plasma, or CSF) of a patient or from perfusion solution useful in the practice of methods of in vivo or ex vivo perfusion disclosed herein.

Various sequences are described herein, and any sequence can be used. In some embodiments, the device comprises a column comprising a histone affinity matrix upstream of, or before, a column comprising a lectin affinity matrix. In some embodiments, the device comprises a column comprising the histone affinity matrix upstream of, or before, a column comprising a lectin affinity matrix upstream of, or before, a column comprising a polyamidoamine dendrimer affinity matrix (PDAM). In some embodiments, the device comprises a column comprising an anti-DNA antibody affinity matrix upstream of, or before, a column comprising a Hoechst 3342 affinity matrix. In some embodiments, the device comprises a column comprising an anti-nucleosome antibody affinity matrix (ANAM) upstream of, or before, a column comprising a polyamidoamine dendrimer affinity matrix (PDAM).

As part of the various embodiments described herein, is (a) performing an apheresis procedure comprising diverting bodily fluid (e.g., blood or plasma, or CSF) from the patient into an apheresis device to produce purified bodily fluid; and (b) returning the purified bodily fluid with reduced levels of the cfDNA to the patient.

As part of other embodiments described herein, is (a) performing an apheresis procedure comprising diverting a perfusion solution e.g., a perfusion solution useful in the practice of methods of in vivo or ex vivo perfusion of an organ and/or anatomical cavity into an apheresis device to produce purified perfusion solution; and (b) returning the purified perfusion solution with reduced levels of the cfDNA to organ and/or anatomical cavity.

The apheresis device may comprise a histone affinity matrix. The histone affinity matrix may comprise recombinant human histone H1.3. The histone affinity matrix may be part of an affinity column. The beads used as support in a histone affinity matrix column may be cellulose beads that are oxidized with an oxidant before coupling with histone. The beads can be sepharose beads, for example. Alternatively, support of forms besides beads can be used (hollow fiber, membrane, tubing, etc.). Support of affinity matrix may be made from other organic and inorganic compounds known to one of skill in the art, for example, polyvinylpyrrolidone (PVP), polysulfone (PS), polyethersulfone (PES), polyarylethersulfone (PAES), polyacrylate, poly(methyl methacrylate) (PMMA), poly(glycidyl methacrylate) (PGMA), poly(hydroxy metacrylate), polystyrene (PS), polytetrafluoroethylene (PTFE), polyacrylamide, polyacrolein, acrylonitrile butadiene styrene (ABS), polyacrylonitrile (PAN), polyurethane (PU), Eupergit®, polyethylene glycol (PEG), hyperfluorocarbon, agarose (i.e., cross-linked agarose), alginate, carrageenan, chitin, starch, cellulose, nitrocellulose, Sepharose®, glass, silica, kieselguhr, zirconia, alumina, iron oxide, porous carbon and mixtures and/or derivatives of said solid supports; and protonated and deprotonated forms of this separation material.

The beads may be coated with DNA-binding proteins. DNA-binding proteins such as histones or anti-DNA antibodies may be immobilized by chemically coupling it to a solid insoluble support matrix such as polysaccharide beads. For example, agarose beads are activated using cyanogen bromide and the cfDNA-capturing protein is incubated with the activated agarose to allow coupling to occur. The unconjugated material is removed by washing with buffer and the protein bound agarose is packed into the targeted apheresis device/affinity cartridge. There are many different methods of chemically coupling proteins to a variety of insoluble support matrixes. These and other matrix materials and methods of protein coupling known to those skilled in the art may be used in any of the methods and devices described herein.

For example, the attachment of a cfDNA-capturing molecule to a solid support can be through an amine, thiol, imide (i.e., water-soluble carbodiimide) or other chemical attachment method known to one of skill in the art to attach a polypeptide or oligonucleotide to a solid support.

The size of the beads can range from 30 to 200 microns, 40 to 180 microns, 45 to 165 microns, 60 to 150 microns, for example. Any number of oxidants may be used, such as sodium metaperiodate (NaIO). Alternatively, the primary hydroxyl group of cellulose can be selectively converted to yield 6-deoxy-6-carboxy-cellulose via oxidation mediated by piperidine oxoammonium salts (TEMPO) or oxidized with chlorite. See, for example, Eyle, S. and Thielemans, W., Surface modification of cellulose nanocrystals, Nanoscale, 2014, 6, 7764, DOI: 10.1039/c4nr01756k) Also, cellulose (or agarose) support can be oxidized by other compounds known to one of skill in the art, for example, chromic acid, chromium trioxide-pyridine, dimethylsulfoxide. (See, for example, Peng, L. et al. Evaluation of activation methods with cellulose beads for immunosorbent purification of immunoglobulins, J. Biotechnology, 5 (1987) 255-265). The oxidized beads are then incubated with a sufficiently purified and concentrated solution of histone protein, such as recombinant human histone H1.3. The reaction may be stopped and then washed with buffer to remove soluble protein contaminants. Alternatively, the primary hydroxyl group of cellulose can be selectively converted to yield 6-deoxy-6-carboxy-cellulose via oxidation mediated by piperidine oxoammonium salts (TEMPO) or oxidized with chlorite. See, for example, Eyle, S. and Thielemans, W., Surface modification of cellulose nanocrystals, Nanoscale, 2014, 6, 7764, DOI: 10.1039/c4nr01756k. Also, cellulose (or agarose) support can be oxidized by other compounds known to one of skill in the art, for example, chromic acid, chromium trioxide-pyridine, dimethylsulfoxide. See, for example, Peng, L. et al. Evaluation of activation methods with cellulose beads for immunosorbent purification of immunoglobulins, J. Biotechnology, 5 (1987) 255-265).

The apheresis device may comprise a histone affinity matrix. The histone affinity matrix may comprise recombinant human histone H1.3. The histone affinity matrix may be part of an affinity column. The beads used in a histone affinity matrix column may be cellulose beads that are oxidized with an oxidant. The beads can be sepharose beads, for example. The beads may be coated with streptavidin. The size of the beads can range from 30 to 200 microns, 40 to 180 microns, 45 to 165 microns, 60 to 150 microns, for example. Any number of oxidants may be used, such as sodium metaperiodate (NaIO). Alternatively, the primary hydroxyl group of cellulose can be selectively converted to yield 6-deoxy-6-carboxy-cellulose via oxidation mediated by piperidine oxoammonium salts (TEMPO). See, for example, Eyle, S. and Thielemans, W., Surface modification of cellulose nanocrystals, Nanoscale, 2014, 6, 7764, DOI: 10.1039/c4nr01756k) Also, cellulose (or agarose) support can be oxidized by other compounds known to one of skill in the art, for example: chromic acid, chromium trioxide-pyridine, dimethylsulfoxide. (See, e.g., Peng, L. et al. Evaluation of activation methods with cellulose beads for immunosorbent purification of immunoglobulins, J. Biotechnology, 1987, 5:255-265). The oxidized beads are then incubated with a sufficiently purified and concentrated solution of histone protein, such as recombinant human histone H1.3. The reaction may be stopped and then washed with buffer to remove soluble protein contaminants.

The histone affinity matrix can be prepared by a process comprising
a) oxidizing cellulose beads having a size between 100 and 250 micrometers to yield activated cellulose beads;
b) washing the activated cellulose beads;
c) preparing a concentrated solution of recombinant human histone H1.3;
d) incubating the activated cellulose beads with the concentrated solution of recombinant human histone H1.3; and
e) blocking any free CHO groups on the activated cellulose beads.

The above process may further comprise f) washing the activated cellulose beads with buffer.

Any oxidant may be used in step a). One exemplary oxidant is NaIO. Any manner of washing can be undertaken in step b). For example, the activated cellulose beads are washed with sodium bicarbonate, hydrochloric acid and water. Dialysis or other methods may be used in step c). For example, a solution of recombinant human histone H1.3 is dialyzed and the dialyzed solution is concentrated in 0.1 M $NaHCO_3$ at pH 7-9, or at pH 8. In step d), the incubation may be performed for 3-5 hours at 15-30° C., or for 4 hours at room temperature. In step e) the blocking step comprises adding 1 M ethanolamine to the activated cellulose beads and reacting for 30 minutes to 2 hours at 15-30° C. In step f) the activated cellulose beads, may be washed with TBS buffer.

The beads may be loaded onto a column, such as, e.g., a polytetrafluoroethylene (PTFE) column. Other exemplary columns may have a wall made of polycarbonate, polyethylene, polyvinylchloride, polypropylene, polyethersulfone, polyester, or other polymer material approved by FDA or EMEA for manufacturing of devices for extracorporeal treating of blood or blood component.

The beads may be loaded into a system which includes a housing and a hollow fiber filter positioned within the housing. The filter may include a plurality of pores sized and dimensioned to permit passage of inflammatory agents having a diameter between about 0.5 nanometers and 7000 nanometers. Therefore, such a system includes beads positioned inside the housing but outside the hollow fiber in an extra-luminal space.

The column, or cartridge device, can be also made of material that is nontoxic and which provides rigid support to the affinity matrix within. Typically, the material will be a plastic composition such as polycarbonate, polyethylene, polyvinylchloride, polypropylene, polyethersulfone, polyester, polystyrene, or other similar material approved by the regulators such as FDA or EMEA for manufacturing of devices for extracorporeal treating of blood or blood component. In some embodiments, there is an inside filter at the bottom of the column (cartridge) to prevent the affinity matrix from leaving the device. In some embodiments, there is also an inside filter at the top of the device to contain the affinity matrix within the device. In some embodiments, these filters are composed of plastic and/or cellulosic material and have pores that will allow flow-through of fluid such as plasma, but not particulate material such as affinity matrix.

In preparing a histone affinity matrix column, the histone affinity matrix may be loaded to at least 50%, 60%, 70%, 75%, 80%, 85%, or 90% column volume. PBS, particularly cold PBS may be used to equilibrate the column. Other suitable buffers may also be used to equilibrate the column.

The apheresis device may comprise a lectin affinity matrix. Non-limiting examples of useful lectins include, e.g., *Galanthus nivalis* (snowdrop) Lectin (GNA), *Narcissus Pseudonarcissus* (Daffodil) Lectin (NPA), Conconavalin A, phytohemagluttanin, and cyanovirin. In one embodiment, a lectin can be coupled to an agarose affinity matrix by incubating overnight at a neutral to slightly alkaline pH. After such incubation, extensive washing with buffer at a pH of near 7.0 to 7.5 may be undertaken to remove the unbound lectin.

A lectin affinity matrix may be prepared according to a process comprising
  a) reacting lectin with activated agarose beads to yield lectin-coupled agarose; and
  b) washing the lectin-coupled agarose with buffer.

The apheresis device may comprise a polyamidoamine (PAMAM) dendrimer affinity matrix (PDAM) or polypropyleneimine (PPI) dendrimer affinity matrix. See, e.g., Kaur et al., J Nanopart Res., 2016, 18:146. Dendrimers are unique synthetic polymers of nanometer dimensions with a highly branched structure and globular shape. Among dendrimers, polyamidoamine (PAMAM) have received most attention as potential transfection agents for gene delivery, because these macromolecules bind DNA at physiological pH. PAMAM dendrimers consist of an alkyl-diamine core and tertiary amine branches. They are available in ten generations (G0-10) with 5 different core types and 10 functional surface groups. DNA and polyamidamine (PAMAM) dendrimers form complexes on the basis of the electrostatic interactions between negatively charged phosphate groups of the nucleic acid and protonated (positively charged) amino groups of the polymers. Formation of high molecular weight and high-density complexes depend mainly on the DNA concentration, with enhancement by increasing the dendrimer-DNA charge ratio. (Shcharbin, D. et al., Practical Guide to Studying Dendrimers. Book, iSmithers Rapra Publishing: Shawbury, Shrewsbury, Shropshire, U K, 2010. 120 p. ISBN: 978-1-84735-444-0.)

The PAMAM dendrimer affinity matrix can be prepared by a process comprising
  a) washing cellulose beads with ethanol and water;
  b) incubating the washed cellulose beads with (±)-epichlorohydrin and NaOH to yield activated cellulose beads;
  c) reacting the activated cellulose beads with PAMAM dendrimer to yield PAMAM beads and removing PAMAM dendrimer that did not react with the activated cellulose beads; and
  d) blocking unconverted epoxy groups on the PAMAM beads.

The beads may be loaded onto a column, such as a polytetrafluoroethylene (PTFE) column. Other exemplary columns may have a wall made of polycarbonate, polyethylene, polyvinylchloride, polypropylene, polyethersulfone, polyester, or other polymer material approved by FDA or EMEA for manufacturing of devices for extracorporeal treating of blood or blood component.

An apheresis device comprising a PAMAM dendrimer affinity matrix may be more effective at removing cfDNA, or alternatively may more completely remove cfDNA, or alternatively may remove a greater overall amount of cfDNA in a particular bodily fluid sample, than using an apheresis device comprising a histone affinity matrix and a lectin affinity matrix.

An apheresis device comprising a PAMAM dendrimer affinity matrix may be more effective at removing cfDNA, or alternatively may more completely remove cfDNA, or alternatively may remove a greater overall amount of cfDNA in a particular perfusion solution, than using an apheresis device comprising a histone affinity matrix and a lectin affinity matrix.

In certain embodiments, the apheresis device may comprise all of a PAMAM dendrimer affinity matrix, a histone affinity matrix and a lectin affinity matrix.

The apheresis device may comprise an anti-DNA antibody affinity matrix. Antibodies to DNA constitute a subgroup of antinuclear antibodies that bind single-stranded DNA, double-stranded DNA, or both (anti-ds+ss DNA antibody). They may be, e.g., IgM antibodies or any of the subclasses of IgG antibodies. Antibodies that bind exclusively to single-stranded DNA can bind its component bases, nucleosides, nucleotides, oligonucleotides, and ribose-phosphate backbone, all of which are exposed in single strands of DNA. Antibodies that bind double-stranded DNA can bind to the ribose-phosphate backbone, base pairs (deoxyguanosine-deoxycytidine and deoxyadenosine-deoxythymidine), or particular conformations of the double helix (Bevra Hannahs Hahn, Antibodies to DNA. N Engl J Med 1998; 338:1359-1368). Antibodies to DNA might also bind DNA containing supramolecular structures like nucleosomes and chromatin.

The anti-DNA antibody affinity matrix can be prepared by activating agarose beads, such as with N-hydroxysuccinimide (NETS). The activated beads can then be incubated with an antibody or other reagent that has affinity to DNA. The excess antibodies/reagents are then removed by washing.

An anti-nucleosome antibody affinity matrix (ANAM) can be prepared by a process comprising
  a) preparing activated agarose beads by crosslinking N-hydroxysuccinimide with agarose beads;
  b) washing the activated agarose beads with coupling buffer comprising $NaHCO_3$ and NaCl;
  c) adding to the coupling buffer an antibody that binds to nucleosomes, wherein the antibody is prepared in a MRL/Mp (−)+/+ mouse;
  d) incubating the coupling buffer comprising the antibody with the activated agarose beads to yield the anti-nucleosome antibody affinity matrix; and
  e) washing the anti-nucleosome antibody affinity matrix with coupling buffer and acetate buffer.

The apheresis device may comprise a DNA intercalator affinity matrix. There are several ways molecules can interact with DNA. Ligands may interact with DNA by covalently binding, electrostatically binding, or intercalating. Intercalation occurs when ligands of an appropriate size and chemical nature fit themselves in between base pairs of DNA. DNA-binding agents tend to interact noncovalently with the host DNA molecule through two general modes: (i) Threading Intercalation in a groove-bound fashion stabilized by a mixture of hydrophobic, electrostatic, and hydrogen-bonding interactions and (ii) Classical intercalation through an intercalative association in which a planar, heteroaromatic moiety slides between the DNA base pairs. Intercalative binding, the most commonly studied, is the noncovalent stacking interaction resulting from the insertion of a planar heterocyclic aromatic ring between the base pairs of the DNA double helix. See http://nptel.ac.in/courses/104103018/35. Hoechst 33342 is a bis-benzimide derivative that binds to AT-rich sequences in the minor grove of double-stranded DNA. The heterocyclic moiety in this dye is important for efficiently interacting with the DNA double helix, thus making the Hoechst-DNA complex more stable. For DNA intercalating properties of chloroquine see, e.g., Kwakye-Berko and Meshnick, Mol. Biochem. Parasitol., 1990, 39(2):275-278.

The DNA intercalator affinity matrix may be prepared by oxidizing (activating) beads, such as cellulose beads (support) reacting with a compound (linker), such as N-(3-dimethylaminopropyl)-N'-ethyl carbodiimide (EDC) that link the DNA-intercalator (DNA-binding moiety, i.e., Hoechst 33342) with support surface. The beads are then washed.

A Hoechst 3342 affinity matrix can be prepared by a process comprising
a) oxidizing cellulose beads;
b) washing the oxidized cellulose beads;
c) reacting the washed oxidized cellulose beads with a solution comprising Hoechst 33342 and N-(3-dimethylaminopropyl)-N'-ethyl carbodiimide (EDC) to yield Hoechst 33342 immobilized cellulose beads; and
d) washing the Hoechst 33342 immobilized cellulose beads.

The apheresis device may comprise a hyperbranched poly-L-lysine affinity matrix. A hyperbranched poly-L-lysine affinity matrix may be prepared by a process comprising
a) dissolving L-lysine monohydrochloride in water and neutralizing with KOH to yield an L-lysine solution;
b) heating the L-lysine solution to yield a solution comprising poly-L-lysine;
c) removing the L-lysine and salt from the solution comprising poly-L-lysine;
d) fractionating the solution comprising poly-L-lysine to obtain a fraction comprising poly-L-lysine with an average molecular weight of 21,000 to 32,000;
e) dialyzing and lyophilizing the fraction comprising poly-L-lysine with an average molecular weight of 21,000 to 32,000 to yield a lyophilizate;
f) dissolving the lyophilizate in distilled water and dialyzing against $NaHCO_3$ to yield a solution comprising HBPL; and
g) incubating the solution comprising HBPL with cyanogen bromide-activated Sepharose 4B suspended in $NaHCO_3$.

In certain embodiments, the apheresis device may comprise all of, or any number of the following: a DNA intercalator affinity matrix, a Hoechst 33342 affinity matrix, an anti-DNA affinity matrix, a PAMAM affinity matrix, a histone affinity matrix, a lectin affinity matrix, and a poly-L-lysine affinity matrix.

Various apheresis procedures and methods of treatment are described throughout the application. Various methods and procedures comprise (a) performing an apheresis procedure comprising diverting bodily fluid (e.g., blood or plasma, or CSF) from the patient into an apheresis device to produce purified bodily fluid; and (b) returning the purified bodily fluid with reduced levels of the cfDNA to the patient. In some embodiments, when the bodily fluid is blood, any vein may be selected for optimal diversion of the blood. For example, the blood may be diverted from the portal vein of the patient. Alternatively, the blood may be diverted from the femoral vein or the jugular vein of the patient. Alternatively, the blood may be diverted from a peripheral vein such as the cubital, cephalic, brachial or basilic vein. In other embodiments, when the bodily fluid is cerebrospinal fluid (CSF), the CSF may be diverted from a subarachnoid space. For example, the CSF may be diverted from a cranial subarachnoid space or a spinal subarachnoid space of the patient. In some embodiments, the CSF may be diverted from the ventricles of the brain of the patient, e.g., the lateral ventricles of the brain of the patient.

In various embodiments of treatment, an apheresis procedure may be carried out more than once, or even twice, for example on day 1 and on day 3. If treating kidney injury, the level of kidney injury may be assessed by measuring serum creatinine and blood urea nitrogen (BUN) levels with Roche Reflotron Plus (Roche Diagnostics) before each apheresis procedure.

Circulating cfDNA may be extracted from plasma samples with conventional THP (Triton-Heat-Phenol) method (Breitbach et al., PLoS ONE, 2014, 9(3):e87838). Extracted cfDNA may be quantified with various assays, such as, e.g., the PicoGreen assay (Molecular Probes, Netherlands) following the manufacturer's instructions. For visualization of cfDNA in agarose gel as described in the examples, below, well known DNA dyes may be used, including, e.g., ethidium bromide (Sigma-Aldrich), Diamond™ Nucleic Acid Dye (Promega), SYBR® Gold Nucleic Acid Gel Stain (Molecular Probes). The dyes may be used as either a gel stain, a precasting agent or may be preloaded directly into sample loading buffer.

In various embodiments, performing an apheresis procedure further comprises separating the blood into plasma. The plasma portion may then be diverted to one or more affinity matrices so as to remove cfDNA.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Preparation of Histone H1 Affinity Matrix and Affinity Column

The histone H1 affinity matrix and affinity column were prepared as follows: cellulose beads (bead size of 100-250 micrometers, Sigma-Aldrich) were oxidized with sodium metaperiodate. To accomplish this, an aqueous suspension of the beads (3 g, 5 mL) and $NaIO_4$ (0.1 g, 0.5 mmol) in 10 mL of water was shaken at room temperature for 4 h. The activated beads were collected and washed with 1 M sodium bicarbonate, 0.1 M hydrochloric acid and 200 mL of water. A solution of recombinant human histone H1.3 (≥98% purity, Institute of Bioorganic Chemistry, Moscow) was dialyzed and concentrated (10 mL; 5 mg/mL) in 0.1 M $NaHCO_3$(pH 8). Then the solution was incubated with oxidized beads (5 ml) at room temperature for 4 h with stirring. After the incubation, 1 M ethanolamine (1.5 mL) was added to the activated beads suspension (15 ml) to block the free CHO groups; the reaction continued for 1 h at room temperature. The resulting cellulose beads with immobilized histone H1 were washed three times with TBS buffer to remove soluble protein contaminants and to provide histone H1 affinity matrix. Polycarbonate columns of 4 mL-30 mL volume were loaded (to 70-90% of the volume) with the cellulose matrix with immobilized histone H1.

Example 2: Purification of the Blood of Cancer Patient from Different Types of Circulating cfDNA Separation of particle bound type of cfDNA (i.e., nucleosome-bound cfDNA and exosome-bound cfDNA) from unbound circulating cfDNA was performed as follows: plasma from a cancer patient with advanced gastric adenocarcinoma and multiple metastases in lungs and liver (T4N2M1) was prepared by collecting blood into citrate-treated tubes and centrifuging for 10 minutes at 2,000 g using a refrigerated centrifuge and collection of supernatant.

The nucleosome-bound cfDNA and exosome-bound cfDNA were removed using two sequential affinity columns containing anti-histone antibody-based affinity matrix and lectin-based affinity matrix.

An anti-histone antibody affinity matrix and a column were prepared as follows: 0.5 mL (1 volume) of streptavidin coated sepharose beads (average bead size: 45 to 165 microns, Pierce Biotechnology, USA) were packed on to a 1.3 volume (1.3 mL) polystyrene column above glass wool. The column was equilibrated with 2 mL (4 volumes) of PBS. 1 mL (volume) of 100 µg/mL solution of biotinylated anti-histone antibodies (H2A.X; Santa Cruz Biotechnologies) were added to the column and allowed to enter the gel bed. The bottom and top caps were sequentially replaced and incubated for 2 hours at room temperature. Following incubation, the column was washed with 2 mL (4 volumes) of cold phosphate buffered saline (PBS). See also WO2007/049286.

Lectin affinity matrix was prepared as follows: 2 mL (1 volume) of Lectin from *Galanthus nivalis* (snowdrop), i.e., GNA (Sigma-Aldrich) solution at a concentration of 10 mg/mL in 0.1M $NaHCO_3$, pH 9.5 was added to 2 mL (1 volume) of CNBr activated agarose beads (Cyanogen bromide-activated-Sepharose 6 MB, 6% agarose, 200-300 µm diameter macrobeads, Sigma-Aldrich) and allowed to react overnight in the cold at pH 7.4-8.0. When the reaction was complete, the lectin coupled agarose was washed extensively with sterile cold phosphate buffered saline (PBS) at pH 7.2-7.4. The prepared lectin affinity matrix was transferred to a 0.6×6 cm polystyrene column. See also U.S. Pat. No. 9,364,601.

For the purification from nucleosome bound cfDNA 1.0 mL of plasma was applied to the first affinity column (comprising anti-histone H2A antibody affinity matrix) and allowed to flow through. Then the plasma was applied to the second affinity (exosome binding) column (comprising lectin [GNA] affinity matrix) and allowed to flow through.

Alternatively, the same amount of the patient plasma was allowed to flow through a single histone H1 affinity column prepared as described in Example 1 (cellulose beads coupled with immobilized histone H1.3).

All plasma samples were analyzed by gel electrophoresis with fluorescent DNA dye staining prior to apheresis and following the completion of apheresis.

Figure 1:
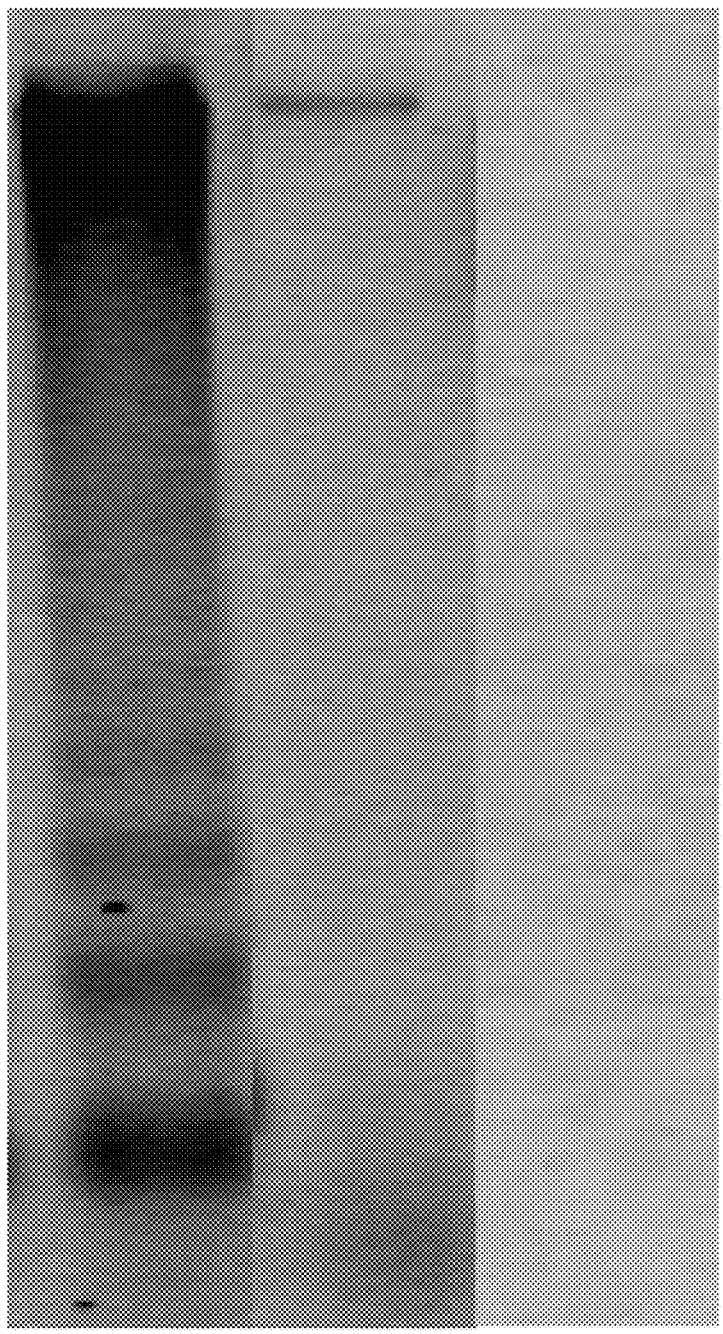
FIG. 1 shows an electrophoretic profile of circulating cfDNA from plasma of a metastatic cancer patient.

The electrophoretic profile of circulating cfDNA from plasma of the cancer patient prior removal of nucleosome bound DNA and exosomes (Lane A), following sequential affinity purification with anti-histone H2A antibody and lectin affinity columns (Lane B) and following affinity purification with histone H1.3 affinity column (Lane C) is presented in FIG. 1.

Even though nucleosome bound circulating cfDNA and exosomes were removed from plasma, the sample shown in the middle lane still contained significant amounts of circulating cfDNA visualized within a molecular range of 100-1000 base pairs. As shown in the right lane, no DNA was visualized in the sample following passage through histone H1.3 affinity column. Thus apheresis/purification of patient plasma through affinity matrix containing DNA binding protein (histone H1.3) can remove essentially all of nucleosome-bound cfDNA, exosome-bound cfDNA and unbound cfDNA, including dsDNA, ssDNA and oligonucleotides, from patient blood.

Example 3: Circulating cfDNA Purified from Nucleosome Bound DNA and Exosomes Promotes Tumor Growth 60 mL of plasma was collected from a metastatic non-small-cell lung carcinoma patient (NSCLC T3N2M+) over a few consecutive days and purified from circulating nucleosome bound cfDNA and from exosomes using anti-histone H2.A antibody and lectin affinity columns, consequently, as described in Example 2 (affinity matrix with anti-histone antibodies and affinity matrix with lectin from *Galanthus nivalis* (snowdrop)). For affinity column preparation, polycarbonate 2.0×7.0 cm columns were used. Each was loaded to 70-80% of the column volume with the corresponding matrix. The remaining circulating cfDNA was extracted from purified plasma using classic phenol chloroform extraction and ethanol precipitation (Stirling, D. et al, DNA extraction from plasma and serum, In: Methods in Molecular Biology, vol. 226: PCR Protocols, Second Edition, Ed. by J. M. C. Bartlett and D. Stirling, Humana Press Inc., Totowa, NJ, 2003, 556 pages). Dry extracted cfDNA was stored at −70° C. The total amount of residual DNA recovered from patient plasma following purification from nucleosome and exosome bound circulating cfDNA was 9.7 µg. The cfDNA was redissolved in PBS and used for animal experiments as described below.

The effect on tumor growth of cfDNA which was not bound to nucleosome and exosome was tested using Panc02/C57/BL6 orthotopic model (Jiang Y-J, Lee C-L, Wang Q, et al. Establishment of an orthotopic pancreatic cancer mouse model. World Journal of Gastroenterology: WJG. 2014; 20(28):9476-9485). $1×10^6$ Panc02 cells suspended in ice-cold Matrigel were injected to pancreas tail of each animal (Day 0). 24 tumor bearing mice were divided into 3 groups of 8 mice each. Control group mice were given single daily injections of PBS (100 µL; retro-orbital venous sinus) for 10 days: from Day 10 to Day 20. Group 1 mice were given daily injections of 100 ng cancer patient cfDNA purified as described above and mice of group 2 were given with 100 ng UltraPure™ Salmon Sperm DNA (Life Technologies) with an average size of ≤2,000 base pairs (as non-specific control) using same schedule and technique.

Table 1 below summarizes the effects of DNA injections on tumor weight in treated animals versus the control group. Tumor weight was measured at the study termination on Day 23.

TABLE 1

| Group | N | Test Material | Tumor Weight (g) Day 23, Median ± SD |
|---|---|---|---|
| Control | 8 | Vehicle (PBS) | 1.37 ± 0.64 |
| Group I | 8 | cfDNA from NSCLC T3N2M+ patient plasma purified from nucleosome and exosome bound cfDNA | 2.53 ± 0.35 |
| Group II | 8 | UltraPure™ Salmon Sperm DNA | 1.11 ± 0.10 |

Figure 2A:
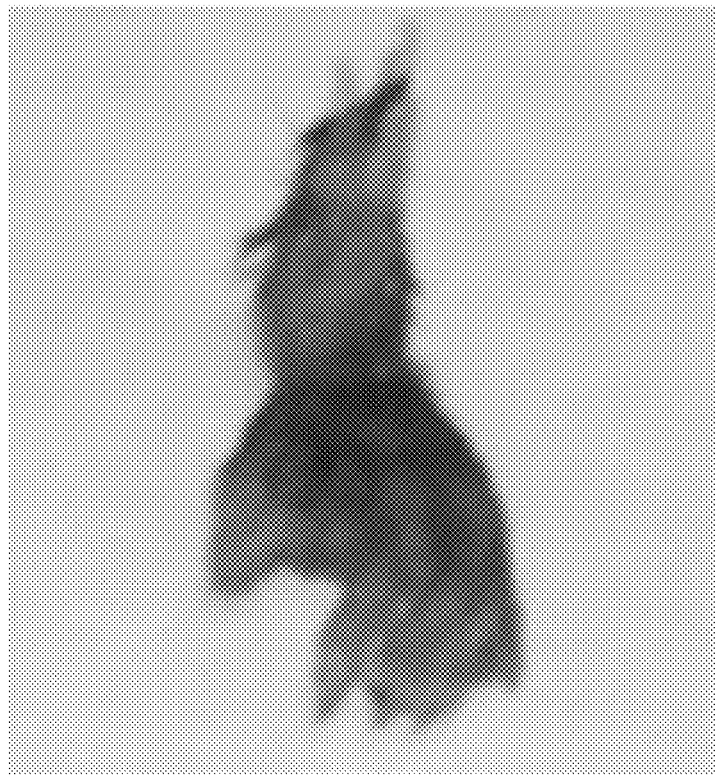
FIGS. 2A and 2B show tumors excised from mice treated with DNA according to Example 3, where blood was purified with an affinity matrix with anti-histone antibodies and an affinity matrix with lectin from *Galanthus nivalis* (snowdrop).
Figure 2B:
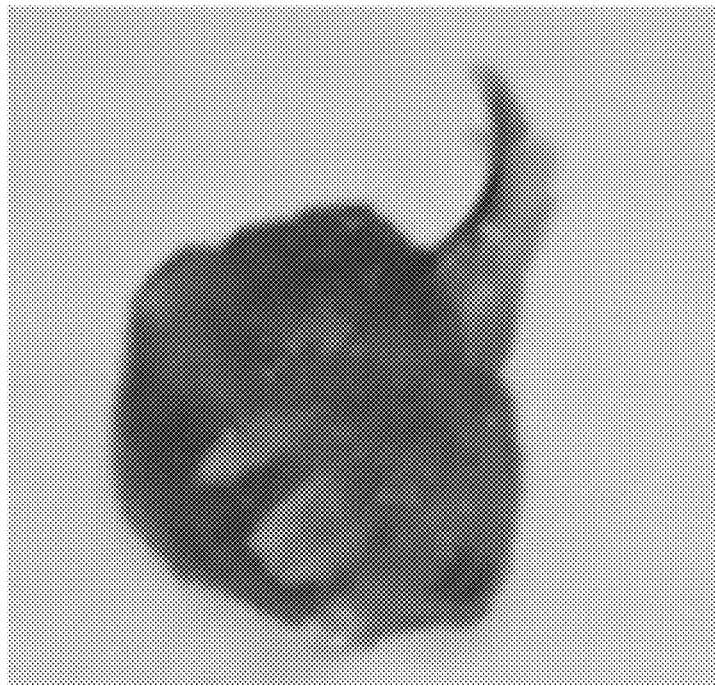

FIG. 2A shows tumors excised from control group mice. FIG. 2B shows tumors excised from mice treated with cfDNA from an NSCLC T3N2M+ patient purified from nucleosome and exosome bound circulating cfDNA. Tumors from the control group were much smaller, dense, well separated from adjacent organs and did not have necrosis and hemorrhages.

These data demonstrate that circulating cfDNA from cancer patient plasma purified from nucleosome and exosome bound circulating cfDNA retained significant tumorigenic properties. Thus, it may be beneficial to reduce levels all of nucleosome-bound cfDNA, exosome-bound cfDNA and unbound cfDNA, including dsDNA, ssDNA and oligonucleotides.

Example 4: Preparation of Polyamidoamine Dendrimer Affinity Matrix and Affinity Column PAMAM dendrimer affinity matrix (PDAM) and columns which contain PDAM were prepared according to Wang (Wang, Y., et al., New method for the preparation of adsorbent with high adsorption capacity, Chinese Science Bulletin 2005, Vol. 50, No. 21, pp. 2432-2435) as follows. Cellulose beads (Macroporous Bead Cellulose MT 500, particle size 100-250 µm, Iontosorb, Czech Republic) were washed twice with 98% ethanol and distilled water. 1 gram of the beads was incubated with a mixture of 1.0 ml (±)-Epichlorohydrin (Sigma-Aldrich) and 3.0 ml of 2.5 M NaOH. The activating reaction was performed at 40° C. for 2.5 h in a shaker. Activated beads were washed thoroughly with distilled water. The epoxy content of the resins was determined as about 0.31 mmol/g of dry beads by titration of sodium thiosulfate with hydrogen chloride. 4.0 ml of prepared wet activated cellulose beads was suspended with 9.0 ml of 20% solution of amino terminated (—$NH_2$) PAMAM dendrimer (ethylenediamine core, generation 3.0, Sigma-Aldrich) solution and shaken at 24° C. for 5 h. After the modification, unreacted PAMAM was removed by washing with distilled water and the remaining unconverted epoxy groups on the beads were blocked by reacting with ethylamine. The functionalized affinity matrix was then washed with 0.1 M phosphate buffer and MilliQ water. 2.0-20.0 mL of prepared affinity matrix were placed in pyrogen free polytetrafluoroethylene (PTFE) (0.5-3.0) cm×(1.0-10.0) cm column (to load of 70-90% of column volume). The prepared affinity column was sterilized by autoclaving at 121° C. for 30 min.

Example 5: Purification of Blood Plasma of Cancer Patient and Stroke Patient from Different Types of Circulating cfDNA 1.0 ml aliquots of plasma samples from both an ischemic stroke patient (24 hours since stroke onset) and a cancer patient with advanced gastric adenocarcinoma with multiple metastases in lungs and liver (T4N2M1) were subsequently purified through both anti-histone H2A antibody and lectin affinity columns, as described in Example 2 (affinity matrix with anti-histone H2A antibodies and affinity matrix with lectin from *Galanthus nivalis* (snowdrop)), or through a polyamidoamine dendrimer affinity 0.6×10.0 cm column alone prepared as described in Example 4 (affinity matrix of cellulose beads coupled with PAMAM dendrimer).

All plasma samples were analyzed by gel electrophoresis with fluorescent DNA dye staining prior to purification and following purification completion.

Figure 3:
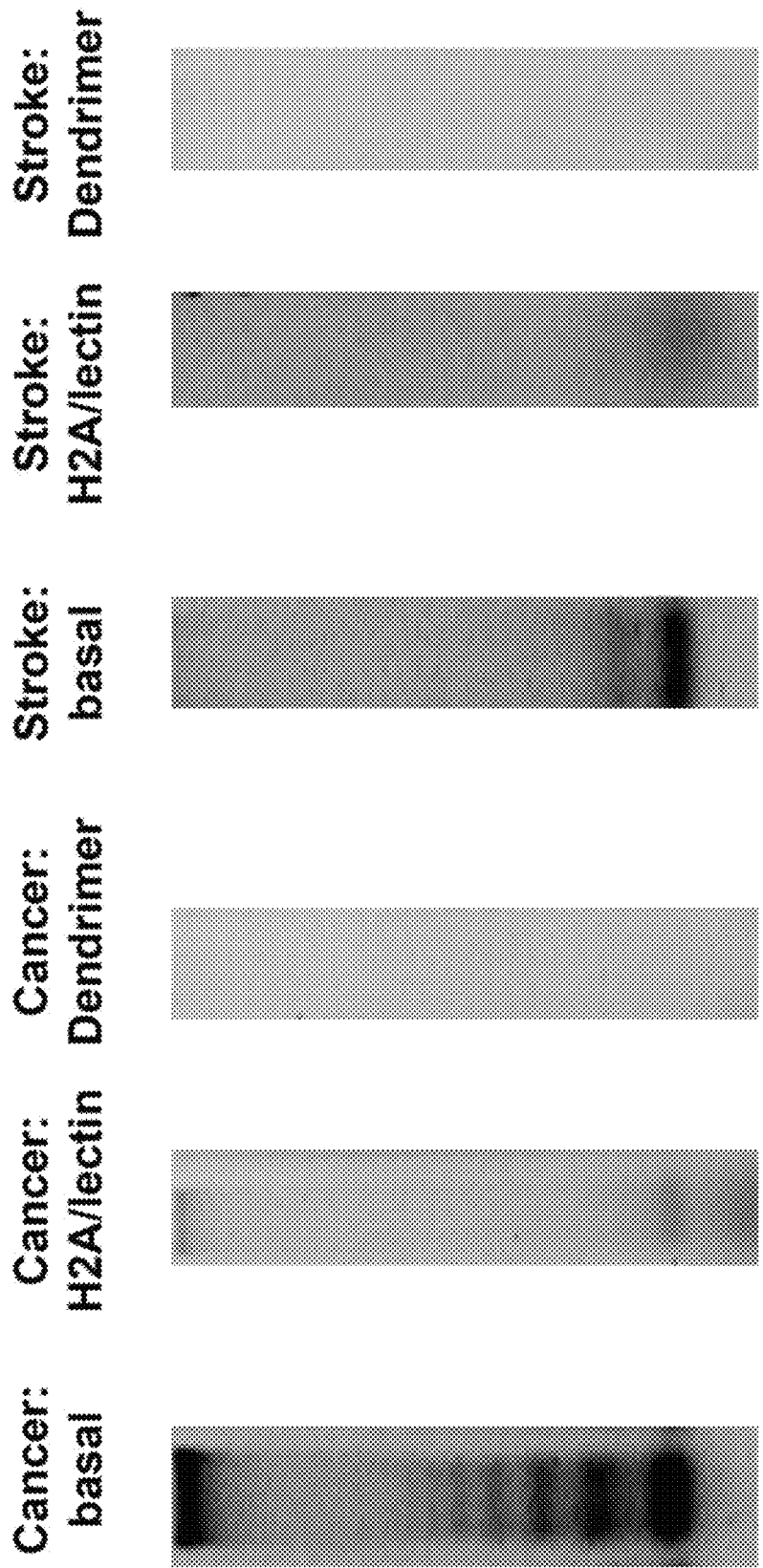
FIG. 3 shows an electrophoretic profile of circulating cfDNA from plasma of a metastatic cancer patient and a stroke patient.

The electrophoretic profile of circulating cfDNA from plasma of these patients prior to removal of nucleosome bound cfDNA and exosomes, following affinity apheresis with anti-histone antibody and lectin affinity columns, and following affinity purification with polyamidoamine dendrimer affinity column are presented in FIG. 3.

Consequent purification of plasma of the cancer patient with anti-histone antibody- and lectin affinity columns removed the majority of particle-bound circulating cfDNA; however, a visible amount of nucleosome bound circulating cfDNA and circulating cfDNA of mononucleosomal size and subnucleosomal size (~below 147 base pairs in length) remained in plasma. Plasma purification with a polyamidoamine (PAMAM) dendrimer affinity column leads to complete elimination of circulating cfDNA from plasma of the cancer patient. In a stroke patient, affinity purification with polyamidoamine dendrimer affinity column (used as a single step) lead to sufficient elimination of substantially all types of circulating cfDNA from the plasma such that they were undetectable.

Thus, the patient blood plasma can be purified from substantially all types of cfDNA, including nucleosome-bound cfDNA, exosome-bound cfDNA and unbound cfDNA (including dsDNA, ssDNA and oligonucleotide) with an affinity matrix containing a DNA binding polymer.

Example 6: cfDNA of Blood Plasma Purified from Nucleosome Bound DNA and Exosomes has Procoagulant Activity U.S. Pat. No. 9,642,822 discloses that high molecular weight circulating nucleosome bound cfDNA in the form of neutrophil NETs has procoagulant activity in patients with advanced cancer and acute vascular events. The blood plasma of patient with stroke (24 hours since onset) and cancer patient with advanced gastric adenocarcinoma with multiple metastasis in lungs and liver (T4N2M1) was sampled and purified consequently through both lectin- and anti-histone antibody affinity columns (prepared as described in Example 2—affinity matrix with anti-histone H2A antibodies and affinity matrix with lectin from *Galanthus nivalis* [snowdrop]) or through polyamidoamine dendrimer (PDAM) affinity 1.0×5.0 cm column (prepared as described in Example 4). Purified and untreated plasma samples were further defibrinated by spinning at 3,000 g for 20 min and filtering through a 0.22 µm filter. Samples were aliquoted into 1.0 mL plastic tubes, shaken in a water bath at 50° C. for 25 min and centrifuged at 10,000 g (10 min). The supernatants were stored at −80° C. and then tested in a thrombin generation assay as follows: a mixture of 25 µL of diluted (1:9) thromboplastin (Sigma), 25 µL of 0.9% NaCl, and 50 µL of 1:1 dilution of defibrinated plasma (all reagents were diluted in 0.9% NaCl).

All reagents in the thrombin generation assay were diluted in 0.9% NaCl. A mixture of 25 µl of thromboplastin, 25 µL of 0.9% NaCl, and 50 µL of 1:1 dilution of defibrinated plasma to be tested were added to wells of a microtiter plate and prewarmed to 37° C. for 10 min. Then 50 of 1 mM spectrozyme, a chromogenic substrate for thrombin, and 50 μL of 30 mM calcium chloride were added sequentially. The plates were read out in an automated enzyme-linked immunosorbent assay plate reader (Victor, Perkin Elmer) at 1000 s and 405 nm at room temperature. All measurements were done in triplicate. In this test OD value is proportional of procoagulant activity of plasma (thrombin generation). The results are shown in Table 2, below.

TABLE 2

| Plasma sample | OD (405 nm) measured at 1000 sec Mean ± SD |
|---|---|
| Cancer patient, untreated | 0.87 ± 0.12 |
| Cancer patient, purified with lectin- and anti-histone antibody affinity matrices/columns | 0.56 ± 0.08 |
| Cancer patient, purified with polyamidoamine dendrimer affinity matrix/column | 0.23 ± 0.07 |
| Stroke patient, untreated | 1.17 ± 0.4 |
| Stroke patient, purified with lectin- and anti-histone antibody affinity matrices/columns | 0.81 ± 0.4 |
| Stroke patient, purified with polyamidoamine dendrimer affinity matrix/column | 0.31 ± 0.3 |
| Healthy donor | 0.13 ± 0.2 |

The data in Table 2 demonstrate that not only nucleosome- and exosome-bound circulating cfDNA but also unbound cfDNA has procoagulant activity in cancer and acute vascular events. Thus, reducing the levels of all types of cfDNA, including nucleosome-bound cfDNA, exosome-bound cfDNA and unbound cfDNA (including dsDNA, ssDNA and oligonucleotides) is beneficial.

Example 7: Preparation of Anti-DNA Antibody Affinity Matrix and Column

Anti-DNA antibody affinity matrix and affinity column were prepared as follows: 5 mL of spherical beads from highly cross-linked N-hydroxysuccinimide (NETS) activated 4% agarose, mean beads size of 90 micrometers (NETS-activated Sepharose 4 Fast Flow, GE Healthcare Life Sciences) were used. The activated matrix was washed twice with cold (2-4° C.) coupling buffer (0.2 M NaHCO$_3$, 0.5 M NaCl, pH 8.3). 1000 μg of high affinity mouse monoclonal IgM Anti-ds+ss DNA antibody ([49/4A1], ab35576, Abcam) were dialyzed against coupling buffer and then coupled according to the manufacturer's procedure to NETS activated Sepharose. Three cycles of washing with coupling buffer followed by 0.1 M acetate buffer (pH 4.0) were used to remove the excess of unbound anti-DNA antibodies. 4 mL of washed affinity matrix was poured to 5 mL column and affinity column was equilibrated in sterile Tris-HCl buffer (pH 7.4).

Example 8: Preparation of DNA Intercalator Affinity Matrix and Column

Hoechst 33342 affinity matrix and affinity column were prepared as follows: cellulose beads (bead size of 100-250 micrometers, Sigma-Aldrich) were oxidized with sodium metaperiodate. For this aqueous suspension of the beads (3 g, 5 mL) and NaIO, (0.1 g, 0.5 mM) in 10 mL of water were shaken at room temperature for 4 h. The activated beads were collected and washed with 1 M sodium bicarbonate, 0.1 M hydrochloric acid and 200 ml of water. 450 mg of activated cellulose beads were mixed with 1000 mL of a pH buffered solution containing 0.047 mg/mL of Hoechst 33342 (Sigma-Aldrich), and 0.4 mg/mL of N-(3-dimethylaminopropyl)-N'-ethyl carbodiimide (EDC) and reacted at a constant vortex rate for 1 h at 32° C. The beads with immobilized Hoechst 33342 were washed three times with deionized water to remove the unreacted dye. The prepared DNA-intercalator affinity matrix was placed into a 4 mL volume plastic (polycarbonate) column. The column was stored at 4° C.

Example 9: Separation of Different Types of Circulating cfDNA from the Blood of Patient with Systemic Inflammatory Response Syndrome (SIRS) and Multiple Organ Dysfunction Syndrome (MODS)

Plasma was sampled from the patient admitted to the intensive care unit (ICU) diagnosed with systemic inflammatory response syndrome (SIRS) with multiorgan failure (multiple organ dysfunction syndrome, MODS) secondary to acute pancreatitis. Therapeutic plasma exchange was performed as a rescue therapy. Aliquots of 1 mL of discharged patient plasma was purified through both lectin and anti-histone antibody affinity columns as described in Example 2 (affinity matrix with anti-histone antibodies and affinity matrix with lectin from *Galanthus nivalis* (snowdrop)) or through a DNA-intercalator affinity column as described in Example 8 (cellulose beads coupled with Hoechst 33342, a DNA intercalator affinity matrix). All plasma samples were analyzed by gel electrophoresis with fluorescent DNA dye staining prior to the purification and following the purification.

Figure 4:
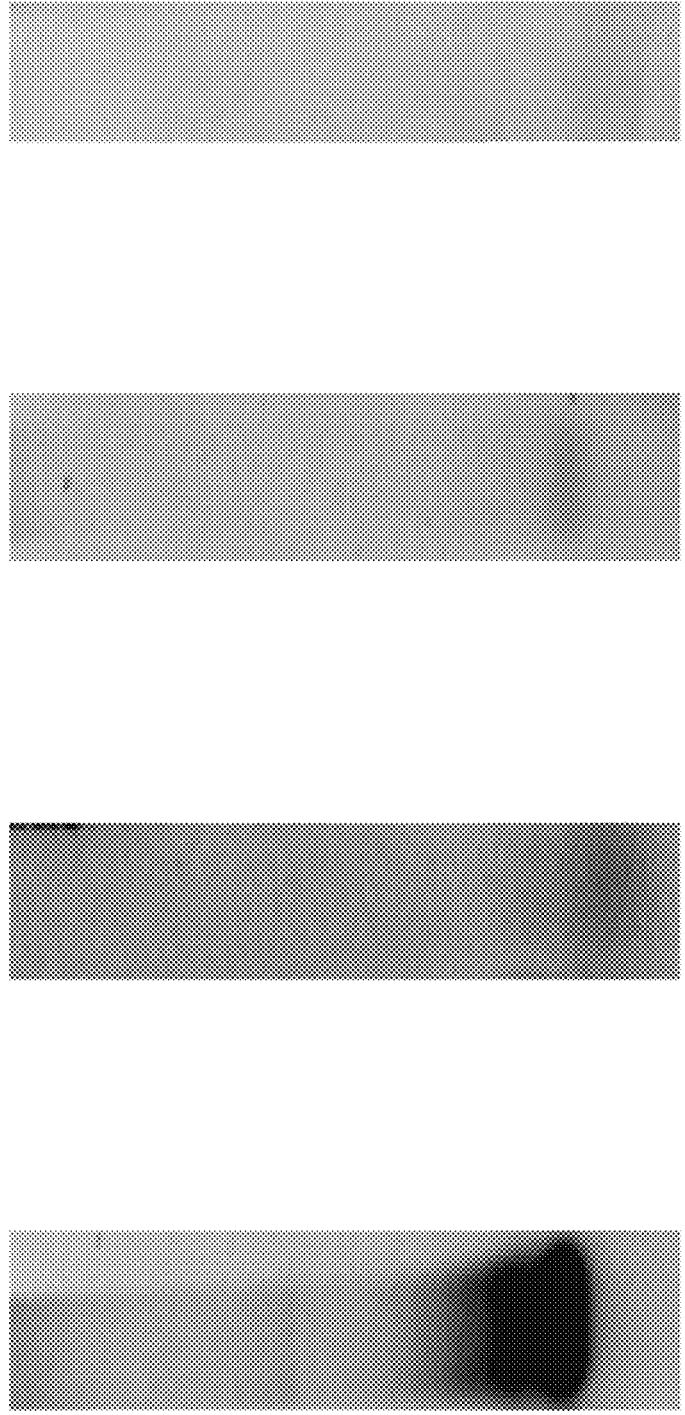
FIG. 4 shows an electrophoretic profile of circulating cfDNA from plasma of patient with systemic inflammatory response syndrome (SIRS) and multiple dysfunction syndrome (MODS).

As shown in FIG. 4, plasma of the SIRS patient contained significant amounts of circulating cfDNA, which gave a strong fluorescent signal following staining with fluorescent DNA dye. Affinity purification with anti-histone antibody and lectin affinity columns removed nucleosome bound circulating cfDNA; however, a certain amount of nucleosome-bound circulating cfDNA and circulating subnucleosomal cfDNA (~below 147 base pairs in length) remained in plasma. Affinity purification with Hoechst 33342 affinity column led to elimination of circulating subnucleosomal cfDNA but a certain amount of nucleosome-bound circulating cfDNA was still present. The inventors therefore tested sequential purification with different columns: 1 ml aliquot of the patient plasma was purified sequentially through Hoechst 33342 affinity column followed by anti-dsDNA antibody affinity column in a manner described in Example 2 for sequential use of anti-histone antibody affinity and lectin affinity columns. Plasma was further checked with by gel electrophoresis with fluorescent DNA dye staining and no circulating cfDNA was detected.

As demonstrated in FIG. 4, purification through DNA intercalator Hoechst 33342 affinity column followed by anti-dsDNA antibody affinity column can remove substantially all types of cfDNA in the patient's blood or plasma, including nucleosome-bound cfDNA, exosome-bound cfDNA and unbound cfDNA (including dsDNA, ssDNA and oligonucleotides).

Example 10: Circulating cfDNA of Plasma Purified from Nucleosome Bound DNA and Exosomes has Proinflammatory Activity and Contributes to Organ Dysfunction in Sepsis Plasma was sampled from the patient admitted to the intensive care unit (ICU) diagnosed with systemic inflammatory response syndrome with multiple organ dysfunction syndrome (MODS) secondary to acute pancreatitis. Therapeutic plasma exchange was performed as a rescue therapy. 100 mL of discarded patient plasma was purified through both lectin and anti-hi stone antibody affinity columns (as described in Example 2, i.e., affinity matrix with anti-histone antibodies and affinity matrix with lectin from *Galanthus nivalis* [snowdrop]) twice to procure complete purification from nucleosome and exosome bound circulating cfDNA. The remaining circulating cfDNA was extracted from the plasma purified from nucleosome and exosome as was described in Example 3. The total amount of residual DNA (recovered from patient plasma purified before from nucleosome- and exosome-bound circulating cfDNA) was about 50 μg. DNA was than resuspended in phosphate buffered saline (PBS) at pH 7.2 and used for an animal experiment as described below.

Eight 10 weeks old C57/BL6 male mice were intravenously injected with 1 μg of extracted cfDNA three times with 1 h interval. Animals were euthanized 4 hours following the last DNA injection for collecting blood.

Plasma creatinine levels were measured by an enzymatic assay. Plasma TNF-α, IFN-γ, and IL-12 levels fluorescent magnetic bead-based immunoassay (Bio-Rad Laboratories, USA). Results are summarized in Table 3, below.

TABLE 3

| Parameter | Value prior first DNA injection | 4 h following last DNA injection. Mean ± SD |
|---|---|---|
| Creatinine | 0.063 ± 0.016 mg/dL | 0.167 ± 0.020 mg/dL |
| IFN gamma | 18.9 ± 5.4 pg/ml | 46.1 ± 6.2 mg/ml |
| TNF alpha | 6.13 ± 2.5 pg/ml | 31.4 ± 5.4 pg/ml |
| IL12 | 17.1 ± 6.2 pg/ml | 278.4 ± 17.4 pg/ml |

As follows from the data in Table 3, cfDNA of plasma purified from nucleosome bound DNA and exosomes still has strong proinflammatory activity and compromises organ function.

Example 11: Circulating cfDNA of Patient Plasma Purified from Nucleosome- and Exosome-Bound DNA but not Purified from Particle-Free DNA is Responsible for TLR9 Activation Activation of TLR9 receptors has been recently recognized as an important component in the development of systemic host-inflammatory response, organ failures, cancer invasion and metastasis, neuronal injury in stroke, autoimmunity, eclampsia and age dependent deregulation of immunity leading to age related proinflammatory status.

The patient was a 33 year-old man with acute myeloid leukemia and an HLA-matched bone marrow transplant (BMT), followed by standard immunosuppression and antibiotic prophylaxis. About 1 month following BMT, the patient developed erythematous rash consistent with GVHD grade III and severe diarrhea. Plasma samples were taken at the patient's admission and purified subsequently with anti-histone H2A antibody and lectin affinity columns as described in the Example 2 (affinity matrix with anti-histone antibodies and affinity matrix with lectin from *Galanthus nivalis* (snowdrop)) or purified with histone H1.3 affinity column prepared as described in Example 1 (affinity matrix of cellulose beads coupled with histone H1.3).

HEK-Blue™ hTLR9 reporter cells (Invivogen) were rinsed with medium to detach them from the culture flask and cells were resuspended to the cell density specified by the manufacturer's protocol. 180 μl of cell suspension per well was stimulated for 24 h (37° C., 5% CO) with 60 μl of untreated patient plasma. Patient plasma was purified through both lectin and anti-histone antibody affinity columns or purified through an H1.3 affinity column (as a single step). After incubation, analysis of secreted embryonic alkaline phosphatase (SEAP) was performed using Quanti-Blue detection medium as described in the manufacturer's instructions.

Detection of absorbance at 650 nm was measured using a microplate reader.

TABLE 4

| Plasma sample | OD (650 nm). Mean ± SD |
|---|---|
| Untreated sample | 0.82 + 0.11 |
| Sample, purified with lectin and anti-histone antibody affinity matrices/columns | 0.73 + 0.07 |
| Sample purified with, histone H1.3 affinity matrix/column | 0.21 + 0.05 |

Quantification of TLR9 activation was performed by reading the optical density (OD) at 620 nm. (N=3.) The results are shown in Table 4. While the elimination of exosomes and nucleosome-bound circulating cfDNA via lectin and anti-histone antibody affinity columns prevented TLR9 activation by patient plasma to a limited extent, the substantial removal of all types of particle-bound and unbound cfDNA, including dsDNA, ssDNA and oligonucleotides, via H1.3 affinity column prevented TLR9 activation by patient plasma almost completely.

Example 12: Preparation of Hyper-Branched Poly-L-Lysine Affinity Matrix (PLLAM) and Affinity Column Cationic poly-aminoacids like poly-L-lysine (PLL) are known to be efficient in condensing plasmid DNA into compact nanostructures and have been used for in vitro and in vivo binding of DNA.

Cationic DNA-binding polymer, namely hyper-branched poly-L-lysine (HBPL) was prepared as described in Kadlecova, Z. et al, A comparative study on the in vitro cytotoxicity of linear, dendritic and hyperbranched polylysine analogs, Biomacromolecules, (2012) v. 13, pp. 3127-3137): 27.45 g of L-lysine monohydrochloride (reagent grade, ≥98%, Sigma-Aldrich, USA) was dissolved in 55 mL Milli-Q water and neutralized by 8.4 g KOH. Then, the solution was heated to 150° C. for 48 h under a stream of nitrogen. Then, to remove excess salt and remaining L-lysine, the polymerization product was dialyzed with dialysis membrane tubing against Milli-Q water (Snakeskin Dialysis Tubing, Thermo Fisher Scientific, Switzerland, molecular weight cut off: 3000 g/mol) The product of dialysis was freeze-dried and then fractionated with Sephadex G75 gel filtration column (GE Healthcare Life Science, Switzerland): the column was loaded with 50 mL of a 2 mg/mL HBPL solution in 0.01 M HCl and subsequently eluted with 0.01 M HCl. Fractions of 20 mL were collected and lyophilized. The fraction with 21000-32000 Daltons average molecular weight (as determined by size exclusion chromatography) was collected and lyophilized. Lyophilized fraction was dissolved in bi-distilled water, dialyzed against 0.1 M NaHCO$_3$ and used for further affinity matrix preparation. Agarose matrix which comprises immobilized HBPL was prepared by a conventional method as follows: cyanogen bromide-activated Sepharose 4B (wet weight 10 g, Sigma)

was suspended in 10 ml of 0.1M NaHCO$_3$, mixed with 10 ml of 21000-32000 HBPL fraction (5 mg/ml in 0.1 M NaHCO$_3$), and stirred for 24 h at 4° C. The prepared HBPL Sepharose (4 mg of HBPL per ml bead suspension) was then poured in a polycarbonate column (1.0×12 cm) and washed with 750 ml of 0.1 M NaHCO$_3$, 750 ml of 0.5 M NaCl and adjusted to pH 9.2. The column was equilibrated with 0.05 M Tris-HCl buffer, pH 7.5. The prepared affinity column with hyper-branched poly-L-lysine affinity matrix (PLLAM) was stored at 4° C.

Example 13: Separation of Different Subtypes of Circulating cfDNA from the Blood of Patient with Neurodegenerative Disease Circulating cfDNA from patients with neurodegenerative disorders can pass through the blood brain barrier (BBB) and induce neuronal cell death. The use of deoxyribonuclease enzyme could abolish this effect. See Int. Pat. Appl. Pub. WO2016190780. To investigate the effect of different subtypes of circulating cfDNA on neuronal cell death and to see if purification of blood from all of nucleosome bound cfDNA, exosome bound cfDNA and unbound cfDNA including dsDNA, ssDNA and oligonucleotides might prevent neuronal cell death, the following experiments were performed.

For neuronal cultures, cerebral cortices were removed from embryonic day (E) 15-17 Sprague Dawley rat embryos. Cortical explants were dissected into pieces of about 200-400 µm$^2$ using fine needles and dissociated with the Papain Dissociation System (Worthington Biochemicals) according to the manufacturer's instructions and further kept on ice-cold minimum essential medium (Gibco). Neurons were plated on 13 mm diameter glass coverslips coated first with poly-D-lysine (10 µg/mL in PBS) followed by laminin (10 µg/mL in PBS) (Gibco) and cultured for 24 hrs. at 37° C. in a humidified 8% CO$_2$ (v/v) atmosphere for 24-48 hrs. in neurobasal medium with 1% (v/v) Antibiotic-Antimycotic (Gibco).

After an initial period of culturing the cell culture media was diluted twice (v/v) with one of the following plasma samples with further culturing for another 24 hrs: (a) plasma of a healthy 20 year old donor, (b) plasma of the patient with rapidly progressed Alzheimer's disease (AD), (c) plasma of the same AD patient treated for 6 hours with 5 µg/mL of DNase I (Pulmozyme, Genentech), (d) plasma of the same AD patient following passage through both of lectin and anti-histone H2A antibody affinity columns (prepared as described in Example 2, i.e. affinity matrix with anti-histone H2A antibodies and affinity matrix with lectin from *Galanthus nivalis* [snowdrop]), and (e) plasma of the same AD patient following passage through histone H1.3 affinity column (the matrix was prepared as described in Example 1, i.e. affinity matrix of cellulose beads coupled with histone H1.3) and placed to 0.8×9 cm polycarbonate column (up to 80% of column volume), with the volume of plasma samples passed through the corresponding columns being about 2.0 mL.

Figure 5:
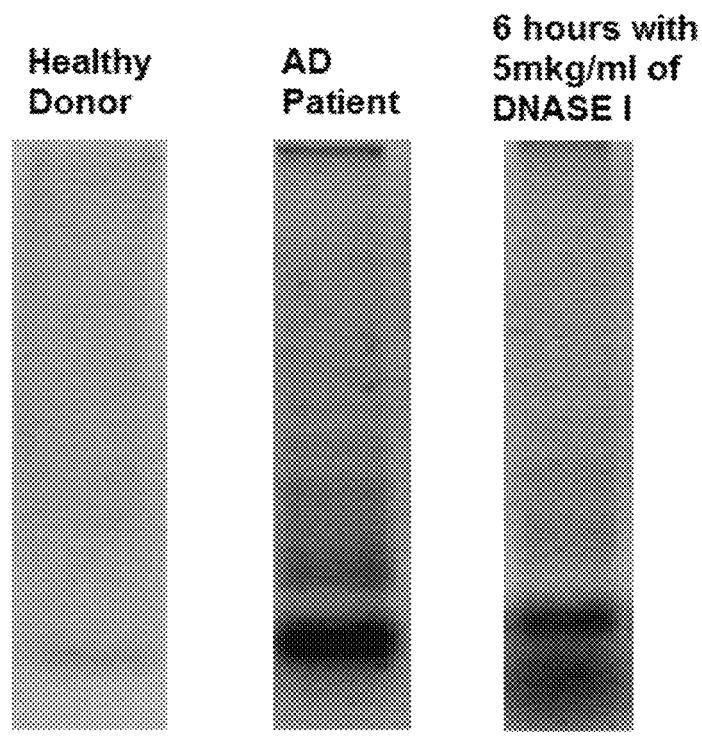
FIG. 5 shows an electrophoretic profile of circulating cfDNA used in cell culture experiments.
Figure 5:
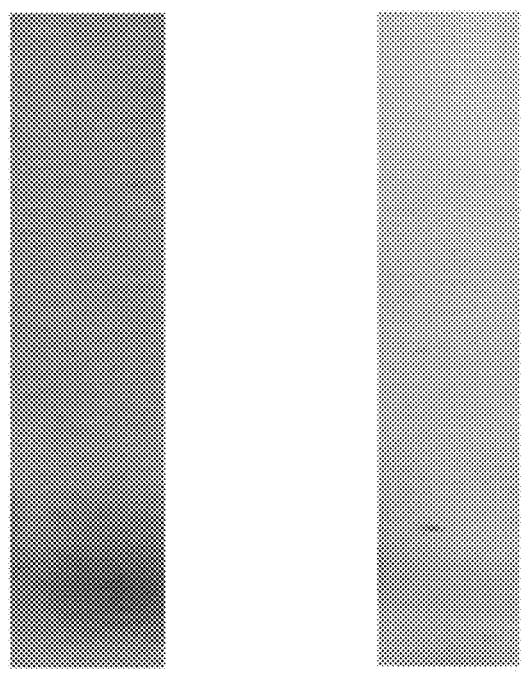

The electrophoretic profile of circulating cfDNA from plasma samples used in cell culture experiments are presented in FIG. 5.

Only a limited amount of nucleosome-bound circulating cfDNA in the form of mononucleosomes was detected in the plasma of a healthy donor. High levels of nucleosome bound circulating cfDNA in the form of mono and oligonucleosmes were detected in the plasma of an AD patient. Treatment of AD patient plasma with DNase I enzyme resulted in a decrease of DNA content in oligonucleosomal and mononucleosomal fractions, but with a significant increase of DNA in subnucleosomal fraction (~below 147 base pairs in length). Plasma of an AD patient purified with lectin and anti-histone H2A antibody affinity columns did not contain nucleosome-bound circulating cfDNA but only subnucleosomal (i.e., unbound) cfDNA. Plasma of an AD patient treated with histone H1.3 affinity column (as a single step) did not contain detectable circulating cfDNA.

Induction of apoptotic cell death marker Caspase 3 was determined in dissociated cortical neurons cultured following 24 hours of exposure to plasma samples. Cells were fixed in 4% (w/v) paraformaldehyde (PFA) and incubated for 1 hour with cleaved Caspase 3 antibody (Abcam) diluted 1:500 in PBS. Cells were washed and incubated for 1 hour with goat anti-rabbit polyclonal Alexa Fluor 488 antibodies (Invitrogen) in PBS prior to washing and counting. The results are shown in Table 5, below.

TABLE 5

| Plasma sample | % of cells positive for Caspase 3; median of three repetitive cell cultures |
| --- | --- |
| Healthy 20 Y donor sample, untreated | 5.3% |
| AD patient sample, untreated | 30.0% |
| AD patient sample treated with DNase I | 15.7% |
| AD patient sample purified with lectin and anti-histone antibody affinity matrices/columns | 17.7% |
| AD patient sample purified with H1 affinity matrix/column | 7.7% |

The data in Table 5 demonstrate that substantial purification of blood from all types of cfDNA, including nucleosome-bound cfDNA, exosome-bound cfDNA and unbound cfDNA (including dsDNA, ssDNA and oligonucleotides), using histone H1.3 affinity matrix prevents neuronal cell death much more efficiently than purification from only nucleosome-bound cfDNA and exosome-bound cfDNA using lectin and anti-histone H2A antibody affinity columns. The ability of histone H1.3 affinity matrix to prevent neuronal cell death is also much more substantial than cleavage of circulating cfDNA in plasma with DNase I enzyme, probably due to release of byproducts of DNA enzymatic degradation or low sensitivity of circulating cfDNA to DNase I.

Example 14: Reactivation of Endogenous Deoxyribonuclease

Deoxyribonuclease enzyme (DNase) is the principal enzyme responsible for degradation of high molecular weight DNA in circulation. Multiple studies show that DNase activity is suppressed in certain conditions involving raised levels of circulating cfDNA in blood, such as cancer, metastatic cancer, autoimmune disease, sepsis, infertility, (Tamkovich S N, Circulating DNA and DNase activity in human blood. Ann N Y Acad Sci. 2006 September; 1075: 191-6; Martinez-Valle, DNase 1 activity in patients with systemic lupus erythematosus: relationship with epidemiological, clinical, immunological and therapeutical features. Lupus. 2009 April; 18(5): 418-23; EP20070827224; Travis J Gould, Cellular and Biochemical Properties of Cell-Free DNA: A Prognostic Marker In Severe Sepsis Patients, Blood 2011, 118:2169).

To assess how reduction of nucleosome-bound cfDNA, exosome-bound cfDNA and unbound cfDNA, including dsDNA, ssDNA and oligonucleotides, affects DNase I activity in plasma the following experiment was performed. cfDNA was measured in plasma using method described by Goldstein (Goldshtein, H. et al., A rapid direct fluorescent assay for cell-free DNA quantification in biological fluids, Annals of Clinical Biochemistry, Vol 46, Issue 6, pp. 488-494). SYBR® Gold Nucleic Acid Gel Stain, (Invitrogen) was diluted first at 1:1000 in dimethyl sulfoxide and then at 1:8 in phosphate-buffered saline. 10 μL of plasma samples were applied 96-well plates. 40 μl of diluted SYBR Gold was added to each well (final dilution 1:10,000) and fluorescence was measured with a 96 well fluorometer at an emission wavelength of 535 nm and an excitation wavelength of 485 nm.

DNase I western blotting was performed in plasma samples separated using 10% SDS-PAGE gels, transferred onto polyvinylidene difluoride (PVDF) blotting membranes, and incubated with goat anti-human DNase I antibodies (Santa Cruz Biotechnology). Binding was visualized using SuperSignal Chemiluminescent Substrate (Pierce) after incubation with HRP-conjugated anti-goat IgG.

Serum deoxyribonuclease activity was measured using ORG590 (Orgentec) according to the manufacturer's protocol. Detection was performed using microplate photometer (Multiscan FC) at 450 nm with a correction wavelength of 620 nm.

Figure 6:
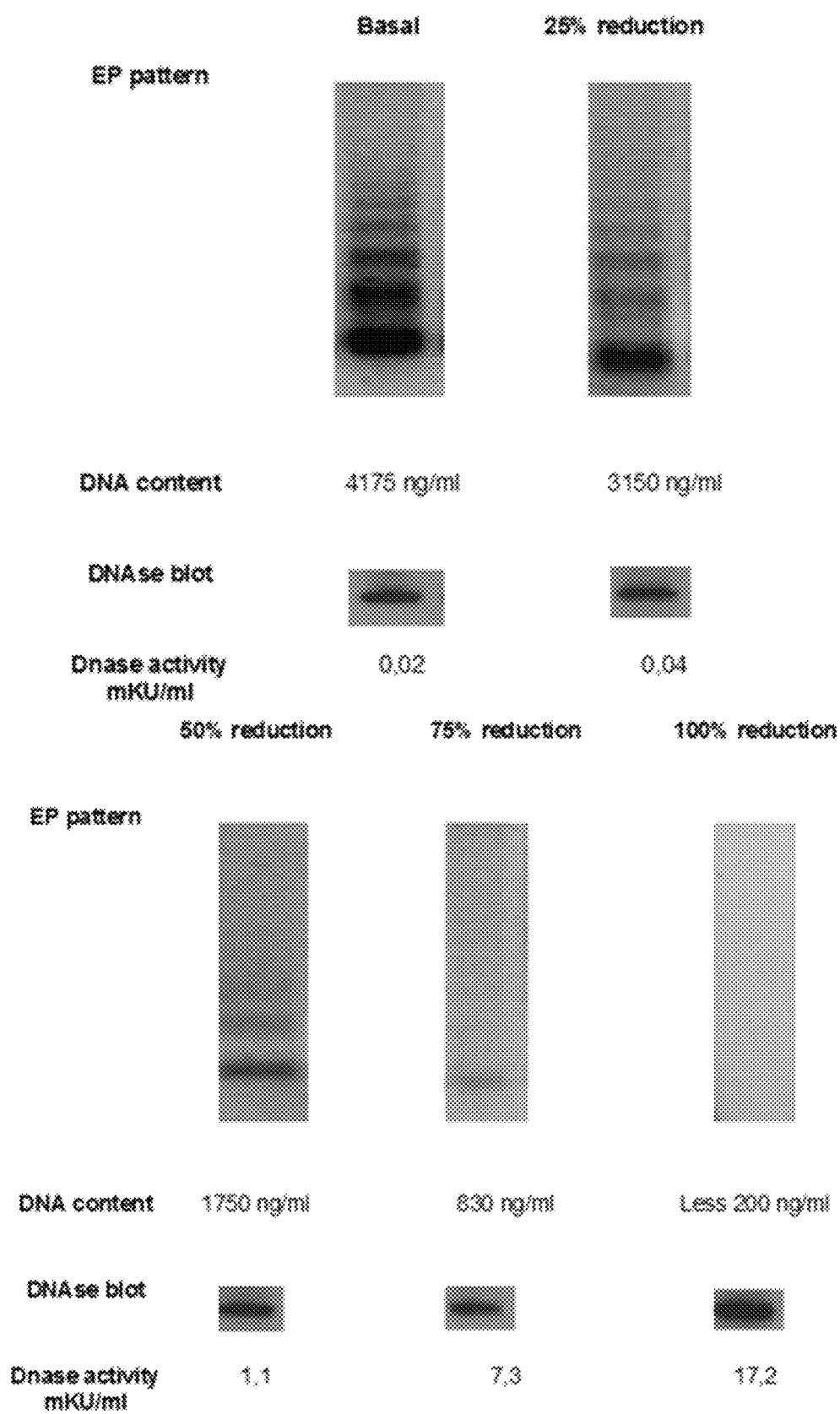
FIG. 6 shows an electrophoretic profile of circulating cfDNA, DNase I western blot and quantification of DNase I activity and circulating cfDNA.

Blood was sampled from 56-year-old female patient with breast cancer, multiple metastasis in lungs, liver and mediastinum (T4N3M1). A 5 mL plasma aliquot was subjected to multiple runs through 1 mL polycarbonate column (0.5×5 cm) containing 0.5 mL of histone H1.3 affinity matrix: assessment of electrophoretic profile of circulating cfDNA, DNAse Western blot and quantification of deoxyribonuclease activity and circulating extracellular content were measured after each column run. The results are summarized in FIG. 6.

The electrophoretic assessment of circulating cfDNA profile showed a continuous decrease of all fractions content alongside with an increasing number of column runs. That observation was confirmed by direct quantification of circulating cfDNA in plasma. A comparable amount of DNase I enzyme as detected by Western blot was present in patient plasma initially. However, enzymatic activity of DNase I was heavily suppressed and became meaningful only after 4 column runs when the amount of circulating cfDNA was decreased approximately twice.

Thus, the apheresis treatment according to the current invention wherein the overall circulating levels of cfDNA are reduced by at least 50% might reactivate the activity of endogenous DNase I enzyme, which is beneficial for patients who require lowering of circulating cfDNA levels.

Based on the highest reported levels of circulating cfDNA of approximately 5000 ng/mL (which are reported for some advanced cancer, septic patients and patient with trauma, see, e.g., Hou et al., Journal of Critical Care, 2016, 31(1): 90-95), the affinity column or combination of affinity columns with binding capacity of 30 mg would be able to provide almost complete purification of patient plasma from all of nucleosome bound cfDNA, exosome bound cfDNA and unbound cfDNA, including dsDNA, ssDNA and oligonucleotides.

Example 15: Preparation of an Affinity Column that Contains Anti-Nucleosome Antibody Affinity Matrix (ANAM)

A mouse monoclonal nucleosome-specific antibody was prepared using MRL/Mp (−)+/+ mouse according to the method described in M. J. Losman (M. J. Losman, Monoclonal autoantibodies to subnucleosomes from a MRL/Mp (−)+/+ mouse. Oligoclonality of the antibody response and recognition of a determinant composed of histones H2A, H2B, and DNA. J Immunol, 1992, 148 (5): 1561-1569). Prepared monoclonal (IgG) antibodies (mAbs), named here as AN-1 and AN-44, were selected on the basis of their ability for selective binding of nucleosomes but not components of nucleosomes like core histones or DNA. (see Kees Kramers, Specificity of monoclonal anti-nucleosome auto-antibodies derived from lupus mice, Journal of Autoimmunity, 1996, V. 9, Issue 6, pp. 723-729). The relative affinities of AN-1 and AN-44 to nucleosomes and histone and non-histone components of nucleosome are summarized in Table 6, below.

TABLE 6

| MAbs | AN-1 | AN-44 |
|---|---|---|
| Nucleosome | 17,400 | 12,000 |
| DNA | 200 | 300 |
| Histones H2A/H2B | <10 | <10 |
| Histones H3/H4 | <10 | <10 |

1 mL HiTrap NHS activated HP column prepacked with NHS activated Sepharose High Performance (GE Healthcare) was used for affinity matrix/cartridge preparation. 200 μg of AN-1 were coupled according to the manufacturer's procedure to NHS activated Sepharose.

The affinity data presented in Table 6, demonstrate that ANAM binds only nucleosome-bound circulating cfDNA but not unbound cfDNA, including dsDNA, ssDNA and oligonucleotides.

Thus, in order to secure binding of unbound cfDNA, including dsDNA, ssDNA and oligonucleotides, two sequential columns were used. One column with anti-nucleosome antibody affinity matrix (ANAM) was prepared as described above. A second column with polyamidoamine dendrimer affinity (PDAM) matrix was prepared as described in Example 4.

Example 16: Apheresis Procedure

Chronic venous catheters were inserted into the femoral vein and the jugular veins of experimental rats under general anesthesia (i.p. injection of 0.8 mg xylazine and 4 mg ketamine). Catheters were flushed three times per week with heparinized saline during the study. Before each apheresis procedure, a heparin bolus was given (90 IU/100 g body weight (b.w.)). The extracorporeal system was fully filled with heparinized saline and thereafter, the catheter endings were connected with the extracorporeal system.

For animal apheresis experiments, the affinity columns were fitted with inlets and outlets for further embedding these prepared affinity columns to the second (plasma) circuit of the extracorporeal/apheresis system.

In the first circuit of the system, blood was pumped (rotary peristaltic mini-pump, Fisher Scientific) from the animal (femoral vein) via a plasma separator (Saxonia Medical, Radeberg, Germany) and returned to the animal by a venous catheter inserted into the jugular vein. The separated plasma entered the second circuit (supported by second rotary peristaltic mini-pump) and passed through one or more affinity cartridges (according to the specific examples of the apheresis procedures described herein), and returned to the animal body via polymer tube also connected to the catheter inserted into jugular vein.

Example 17: Apheresis Treatment of Sepsis and Septic Kidney Injury

Classic sepsis-induced models by the method of cecal ligation and puncture (CLP) were established. Female Sprague-Dawley (SD) rats of 350-400 g body weight were used. Animals were anesthetized with sodium pentobarbital (50 mg/kg intraperitoneally).

A midline abdominal incision about 1.5 cm was performed. The cecum mesentery was dissected to expose the cecum. Then, the cecum was ligated between the terminal and ileocecal valve so that intestinal continuity was maintained. Then, the cecum was perforated by single through-and-through puncture with a 21-gauge needle in the central segment of ligation. The tied segment was gently pressed to ensure that a small amount of feces was extruded on to the surface of the bowel. The cecum was returned to the abdominal cavity. The surgical wound was sutured layer by layer with absorbable suture for the muscle layer and with surgical staples for the skin. After operation, the rats were injected with 10 ml/kg warm 0.9% sodium chloride for injection and after recovery the animals were randomly divided into three groups (Groups 1-3; 6 animals in each group) according to the treatment.

The apheresis treatment was performed as described in Example 16. The apheresis procedure was carried out twice: on day 1 (24 hrs after CLP), and day 3 (72 hrs after CLP). 6 rats underwent apheresis procedure using column/cartridge with anti-nucleosome antibody affinity matrix (ANAM) prepared as specified in Example 15, and 6 rats underwent the apheresis procedure using column/cartridge containing PAMAM dendrimer affinity matrix (PDAM) prepared as specified in Example 4. Six rats (negative control group) received the apheresis procedure with a cartridge that was loaded with a corresponding volume of unmodified support (Sepharose 4B). Level of acute kidney injury (renal function) was assessed by measurement of serum creatinine and blood urea nitrogen (BUN) levels with Roche Reflotron Plus (Roche Diagnostics) before each apheresis procedure. Circulating cfDNA was extracted from 100 plasma samples with conventional THP (Triton-Heat-Phenol) method (Breitbach et al., PLoS ONE, 2014, 9(3):e87838). DNA was quantified with the PicoGreen assay (Molecular Probes, Netherlands) following the manufacturer's instructions and cfDNA changes were expressed as percentage of DNA level relative to baseline, i.e., to the level before the first apheresis procedure. For the negative control group, the columns/cartridges containing corresponding amount of unmodified support (Macroporous Bead Cellulose MT 500, particle size 100-250 Iontosorb, Czech Republic, washed twice with 98% ethanol and bi-distilled water) were prepared. The survival rate (120 hours after CLP) was assumed to be the main parameter of sepsis treatment efficacy. The allocation of the animals and the results are shown in Table 7, below.

TABLE 7

| Hours post CLP | 24 | 48 | 72 | 96 | 120 |
|---|---|---|---|---|---|
| CLP + apheresis with unmodified support cartridge (Negative Control); n = 6 | | | | | |
| Circulating levels of cfDNA (before/after apheresis) | 100%/100% | | 137%/137% | | |
| Serum creatinine, μmol/L | 140 ± 20 | 160 ± 12 | 194 ± 31 | 215 ± 16 | |
| Blood urea nitrogen (BUN), mmol/L | 11.2 ± 2.1 | 14.9 ± 2.8 | 16.8 ± 3.5 | 18.2 ± 3.0 | |
| Survival | | | | | 1 of 6 |
| CLP + apheresis with ANAM cartridge; n = 6 | | | | | |
| Circulating levels of cfDNA (before/after apheresis) | 100%/58% | | 66%/32% | | |
| Serum creatinine, μmol/L | 136 ± 12 | 139 ± 13 | 145 ± 14 | 140 ± 13 | |
| Blood urea nitrogen (BUN), mmol/L | 12.3 ± 2.2 | 12.8 ± 2.2 | 13.5 ± 2.5 | 14.7 ± 2.1 | |
| Survival | | | | | 3 of 6 |
| CLP + apheresis with PDAM cartridge, n = 6 | | | | | |
| Circulating levels of cfDNA (before/after apheresis) | 100%/21% | | 33%/12% | | |
| Serum creatinine, μmol/L | 138 ± 12 | 100 ± 13 | 105 ± 14 | 111 ± 16 | |
| Blood urea nitrogen (BUN), mmol/L | 12.4 ± 1.7 | 8.4 ± 1.0 | 10.4 ± 2.2 | 12.6 ± 3.7 | |
| Survival | | | | | 5 of 6 |

The results show that the PDAM apheresis device was able to capture substantially all types of cfDNA, including nucleosome-bound cfDNA, exosome-bound cfDNA and unbound cfDNA (including dsDNA, ssDNA and oligonucleotides) and provided a better therapeutic efficacy and more efficiently reduced the level of circulating cfDNA in sepsis and septic kidney injury.

Example 18: Apheresis Treatment of Chemotherapy Related Toxicity Signs 18 female Sprague-Dawley (SD) rats of 300-350 g body weight were prepared for the apheresis procedure as described in Example 16 and received a single intravenous bolus injection of paclitaxel (Taxol, Bristol-Myers Squibb S.r.L.) at 10 mg/kg dose. The apheresis procedure was started 4 hours following paclitaxel injection and continued for 12 hours; 6 rats received the apheresis procedure using column/cartridge with anti-nucleosome antibody affinity matrix (ANAM), and 6 rats received the apheresis procedure using column/cartridge containing hyper-branched poly-L-lysine affinity matrix (PLLAM). 6 rats (negative control) received the apheresis procedure with a cartridge that was loaded with a corresponding volume of unmodified support (Sepharose 4B).

Circulating cfDNA levels were quantified and presented as described in Example 17 (with cfDNA expressed as percentage of DNA level to baseline). The survival rate (24 hours after bolus) was assumed to be the main parameter of treatment efficacy. The allocation of the animals and the results are shown in Table 8, below.

TABLE 8

| Hours post Paclitaxel bolus | 4 h | 16 h | 24 h |
| --- | --- | --- | --- |
| Paclitaxel + apheresis with unmodified support cartridge (Negative Control) n = 6 | | | |
| Circulating levels of cfDNA (before/after apheresis) | 100% | 230% | |
| Survival | | | zero from 6 |
| Paclitaxel + apheresis with ANAM cartridge; n = 6 | | | |
| Circulating levels of cfDNA (before/after apheresis) | 100% | 165% | |
| Survival | | | 2 from 6 |
| Paclitaxel + apheresis with sequential PLLAM cartridge, n = 6 | | | |
| Circulating levels of cfDNA (before/after apheresis) | 100% | 65% | |
| Survival | | | 5 from 6 |

The results show that the PLLAM apheresis device was able to substantially capture all types of cfDNA, including nucleosome-bound cfDNA, exosome-bound cfDNA and unbound cfDNA (including dsDNA, ssDNA and oligonucleotides) in order to provide better protection/therapeutic efficacy and more efficiently reduced the level of circulating cfDNA in animals poisoned by a chemotherapeutic drug.

Example 19: Purification/Apheresis of Plasma cfDNA with One Cartridge that Captures Nucleosome- and Exosome-Bound DNA and Another Cartridge that Captures Unbound cfDNA, Including dsDNA, ssDNA and Oligonucleotides For the measurements of plasma cfDNA level, cfDNA was extracted from 500 μL plasma samples using the modified HTP method (Xue, X., et al. Optimizing the yield and utility of circulating cell-free DNA from plasma and serum, Clinica Chimica Acta, 2009, v. 404, pp. 100-104) and quantified using the PicoGreen assay (Molecular Probes, Netherlands) according to the manufacturer's instructions.

When cfDNA was undetectable in a sample by PicoGreen assay, the absence of cfDNA in the samples was further confirmed by DNA electrophoresis in agarose gel in a manner described above.

For apheresis/purification procedures plasma samples were gradually applied to the corresponding affinity columns and allowed to flow through.

A 2.0 mL plasma sample obtained from 67-year-old septic shock patient was purified consequently through an ANAM affinity column. The ANAM affinity column (which captures nucleosome-bound cfDNA) was prepared on the basis of 1 mL HiTrap NHS activated HP column (as described in Example 15). The lectin affinity column (which captures exosome-bound cfDNA) was prepared as described in the Example 2 (affinity matrix with lectin from *Galanthus nivalis* [snowdrop]).

Figure 7:
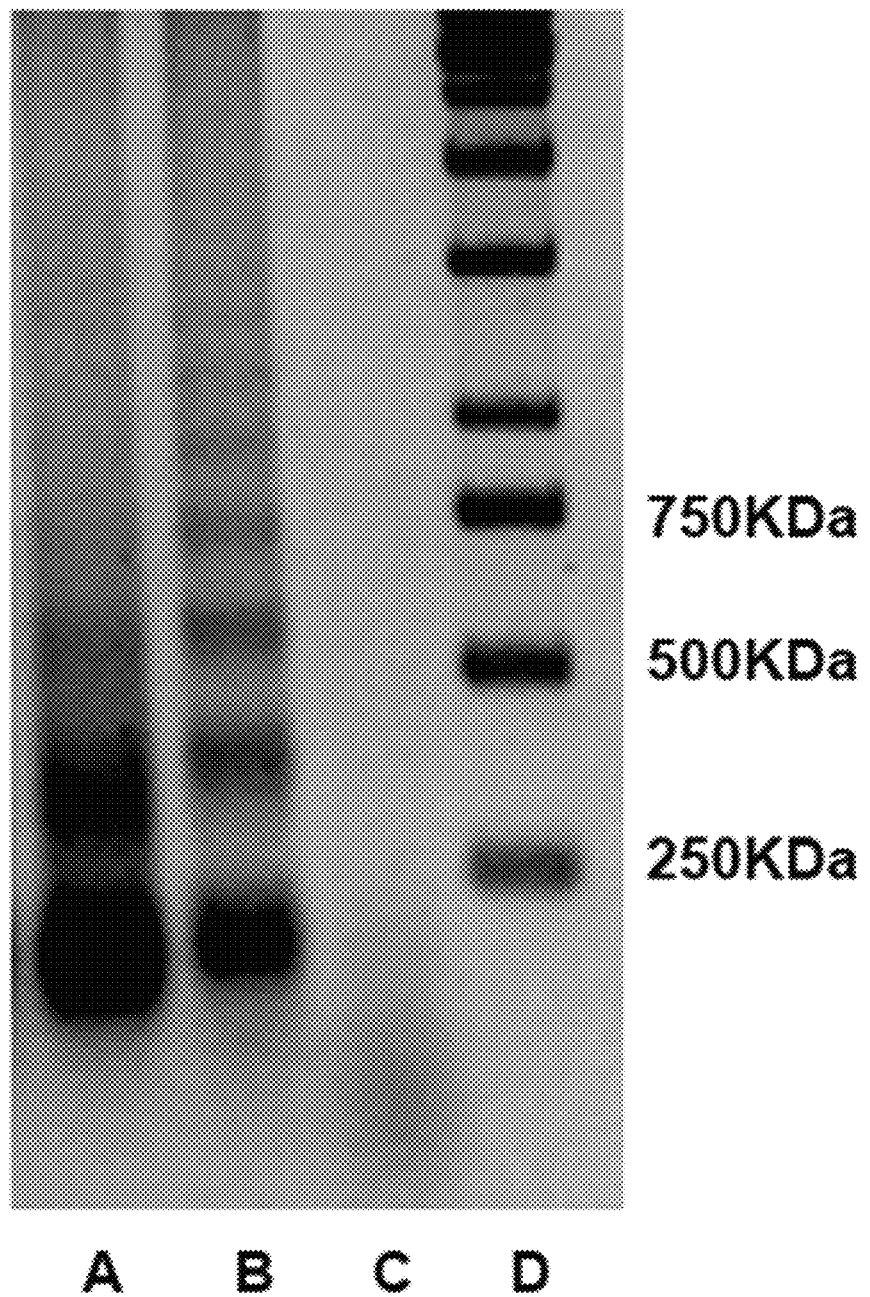
FIG. 7 shows an electrophoretic profile of circulating cfDNA from plasma of a patient with sepsis.

Initial cfDNA level in patient plasma was 1150 ng/mL with significant presence of all types of cfDNA visualized by DNA electrophoresis in agarose gel (See FIG. 7, lane A). The level of cfDNA in plasma following a first run through a combination of ANAM and lectin affinity columns decreased to 350 ng/mL. Partially purified patient plasma was further subjected to a second run through same combination of fresh ANAM and lectin affinity columns. The level of cfDNA in plasma following second run remained unchanged with visible amounts of cfDNA of non-nucleosomal origin with molecular weight of up to 750 kDa visualized by DNA electrophoresis in agarose gel with fluorescent DNA dye staining (See FIG. 7, lane C).

The experiment made clear that the inability of ANAM and lectin affinity columns to completely purify patient plasma from cfDNA did not relate to the overall binding capacity of the AMAM and lectin affinity columns' combination but rather to its inability to capture cfDNA of non-nucleosomal or non-exosomal origin from patient plasma. In order to confirm this, we further purified the sample through an anti-DNA antibody affinity column prepared as described in Example 7 (matrix of agarose coupled with high affinity mouse monoclonal IgM Anti-ds+ss DNA). Following one purification run, the level of cfDNA in patient plasma became undetectable as measured by PicoGreen assay. This observation was further confirmed by the absence of visible DNA material following DNA electrophoresis in agarose gel.

Thus, the use of two sequential affinity columns/cartridges, wherein one column/cartridge captures nucleosome-bound DNA and exosome-bound DNA and the other column/cartridge captures unbound cfDNA including dsDNA, ssDNA and oligonucleotides, is very effective for purification/apheresis of patient blood from all type of circulating cfDNA.

Another 2 mL plasma sample from the same patient were purified consequently through a DNA-intercalator affinity column (prepared as described in Example 8, i.e., cellulose beads coupled with Hoechst 33342) and an anti-DNA antibody affinity column (prepared as described in Example 7, i.e., matrix of agarose coupled with high affinity mouse monoclonal IgM anti-DNA). The level of cfDNA in plasma following a first run through a combination of DNA-intercalator and anti-DNA antibody affinity columns decreased to 475 ng/mL with cfDNA of different origin visualized by DNA electrophoresis in agarose gel (FIG. 7, Lane B). This partially purified patient plasma was further subjected to a second run through the same combination of fresh DNA-intercalator and anti-DNA antibody affinity columns. The level of cfDNA in plasma following the second run of the patient plasma became undetectable as measured by PicoGreen assay. This observation was further confirmed by the absence of visible DNA material following DNA electrophoresis in agarose gel with fluorescent DNA dye staining.

Thus, the use of a combination of columns/cartridges containing matrices which substantially bind all types of cfDNA (including nucleosome-bound cfDNA, exosome-bound cfDNA and unbound cfDNA [including dsDNA, ssDNA and oligonucleotides]) permits capture of an unusually high amount of cfDNA.

Example 20: Purification/Apheresis of Plasma from the Portal Vein to Purify cfDNA from Blood of Rats with Acute Pancreatitis Six male Sprague-Dawley rats, 250-350 grams, were used in the experiment. All surgical procedures were performed on a heated operating table under general anesthesia with i.p. injection of 0.8 mg xylazine and 4 mg ketamine.

Acute pancreatitis was induced as follows. During laparotomy the papilla of Vater was cannulated transduodenally using a 24G Abbocath®-T i.v. infusion cannula. Before a pressure monitored infusion of 0.5 mL sterilized glycodeoxycholic acid in glycylglycine-NaOH-buffered solution (10 mmol/L, pH 8.0, 37° C.) was administered, the common bile duct was clamped and bile and pancreatic fluid were allowed to drain through the cannula. Directly after infusion, hepato-duodenal bile flow was restored by removal of the clamp. The puncture hole in the duodenum was carefully closed using an 8.0 polyprolene serosal suture.

After closure of the abdomen in Rats 1, 2 and 3, chronic venous catheters were inserted into the femoral vein and the jugular vein as described in Example 16.

Rats 4, 5 and 6 had a portal vein catheter implanted into the hepatic portal vein 8 mm caudal of the liver as described by Strubbe (Strubbe J. H. et al, Hepatic-portal and cardiac infusion of CCK-8 and glucagon induce different effects on feeding. Physiol Behav 46: 643-646, 1989).

The apheresis treatment was performed as described in Example 16 using PDAM affinity cartridge, prepared as was described in Example 4 and fitted with polypropylene inlet and outlet. The apheresis procedure was carried out daily during days 1-3 with 12 hours duration of each apheresis procedure.

The survival rate (at 96 hours following induction of pancreatitis) was assumed as a main parameter of treatment efficacy. For quantification of cfDNA of rat and cfDNA of bacteria origin (i.e., bacterial load), total cfDNA was isolated from 200 µL rat plasma samples using a QIAamp DNA Mini Kit according to the manufacturer's instructions. For quantification of cfDNA of rat and cfDNA of bacteria origin (i.e., bacterial load), total cfDNA was isolated from 200 µL rat plasma samples using a QIAamp DNA Mini Kit according to the manufacturer's instructions. cfDNA concentration on the plasma samples were measured by quantitative polymerase chain reaction (PCR) using the ABI PRISM 7700 Sequence Detector (Applied Biosystems) and TaqMan Universal PCR Master Mix (Applied Biosystems) according to the manufacturer's protocol. For quantification of cfDNA of bacterial origin, specific primers and a probe were designed for the conserved regions of bacterial 16S rDNA: the forward primer, 5'-TCCTACGGGAGGCAGCAGT-3' (SEQ ID NO: 14), the reverse primer 5'-GGAC-TACCAGGGTATCTAATCCTGTT-3' (SEQ ID NO: 15) and the probe (6-FAM)-5'-CGTATTACCGCGGCTGC-TGGCAC-3'-(TAMRA) (SEQ ID NO: 16) (see: Mangala, A.; Nadkarni, A. Determination of bacterial load by real-time PCR using a broad-range (universal) probe and primers set. Microbiology, 2002, vol. 148, pp. 257-266). TaqMan Gene Expression Assay rat β-actin Rn00667869_m1 (Applied Biosystems) was used for amplification of rat genomic cfDNA Survival/outcome and the results of each PCR (Ct, i.e., threshold cycle value) for rat β actin gene and bacterial 16S rDNA in blood plasma sampled from jugular vein are presented in Table 9, below.

TABLE 9

| | Vein from which the blood was diverted | β actin gene Ct* | 16S rDNA Ct* | Survival/Outcome |
|---|---|---|---|---|
| Rat 1 | Femoral vein | 29.49 ± 0.161 | 24.22 ± 0.096 | Alive at 96 h |
| Rat 2 | Femoral vein | 29.2 ± 0.379 | 23.85 ± 0.218 | Dead at 82 h |
| Rat 3 | Femoral vein | 28.62 ± 0.278 | 23.59 ± 0.109 | Alive at 96 h |
| Rat 4 | Portal vein | 30.26 ± 0.176 | 27.89 ± 0.112 | Alive at 96 h |
| Rat 5 | Portal vein | 30.26 ± 0.21 | 25.78 ± 0.155 | Alive at 96 h |
| Rat 6 | Portal vein | 30.44 ± 0.151 | 29.42 ± 0.341 | Alive at 96 h |

*Mean ± SD of three independent runs. Ct values are natural logarithmic and inverse to the amount of nucleic acid or gene of interest in the sample. The Ct is the cycle number at which the fluorescence generated within a reaction crosses the threshold line.

The results show that diverting/removing the blood for apheresis from the portal vein into an apheresis device resulted in a better (as compared to diverting the blood from the femoral, i.e., non-regional vein) survival and more effective purification of blood from cfDNA (including cfDNA of bacterial origin) in rats with acute pancreatitis.

Thus, in clinical circumstances where a pathological process responsible for the release of cfDNA (e.g., in tumor growth, septic or aseptic inflammation, bacterial DNA release, etc.) originates from areas/regions drained primarily by the portal vein (e.g., esophagus, gastric, intestinal, splenic, pancreatic, gallbladder, peritoneal cavity) diverting the blood for the apheresis procedure from the portal vein might be beneficial.

Example 21: Comparison of cfDNA Removal from Patient Plasma by Histone H1 Affinity Matrix, PAMAM Dendrimer Affinity Matrix and Poly-L-Lysine Affinity Matrix (PLLAM)

Poly-L-lysine affinity matrix (PLLAM) was produced as specified in Example 12. PAMAM dendrimer affinity matrix (PDAM) was produced as specified in Example 4. Histone H1 affinity matrix was produced as specified in Example 1.

Model plasma enriched with cfDNA was produced by mixing plasma of a healthy volunteer with marker DNA (1 kbp plus DNA Ladder, Invitrogen) to the final cfDNA concentration of 10 µg/ml. Adsorption capacity of poly-L-lysine affinity matrix (PLLAM), PAMAM dendrimer affinity matrix (PDAM) and histone H1 affinity matrix with respect to model plasma enriched with artificial 1 kbp plus DNA Ladder was tested by the volume adsorption method with affinity matrix: plasma ratio 1:5 (100 µl of affinity matrix was mixed with 500 µl of model plasma) for 1 hour at 37° C. under slow rotation. Ethanolamine Sepharose FF was used as a control. Plasma samples were analyzed by 1% agarose gel electrophoresis using the E-Gel Invitrogen system prior to incubation and upon sedimentation of affinity matrix. cfDNA was extracted from patient plasma using QIAamp DNA Blood Mini Kit, Qiagen and quantified with Qubit 3.0 fluorimeter. The same affinity matrixes were incubated with plasma of the patient diagnosed with odontogenic-related sepsis with affinity matrix: plasma ratio 1:10 (100 µl of affinity matrix was mixed with 1 ml of patient plasma) using the same incubation conditions. In one hour, affinity matrix was removed by centrifugation. Plasma samples were analyzed by 1% agarose gel electrophoresis using the E-Gel Invitrogen system prior to incubation and upon sedimentation of affinity matrix. Ethanolamine Sepharose FF was used as a control. cfDNA was extracted from patient plasma using QIAamp DNA Blood Mini Kit, Qiagen and quantified with Qubit 3.0 fluorimeter. cfDNA quantification data are presented in Table 10, below.

TABLE 10

| | cfDNA content in model plasma; ng/ml, median ± SD | | | | |
|---|---|---|---|---|---|
| | Prior to incubation | After incubation | | | |
| | | Control | H1.3 | PDAM | PLLAM |
| Model plasma enriched with cfDNA | 992 ± 24 | 942 ± 17 | 44 ± 19 | 92 ± 23 | 83 ± 24 |
| Plasma from patient with odontogenic-related sepsis | 1832 ± 43 | 1648 ± 17 | 57 ± 17 | 488 ± 24 | 392 ± 43 |

Figure 8:
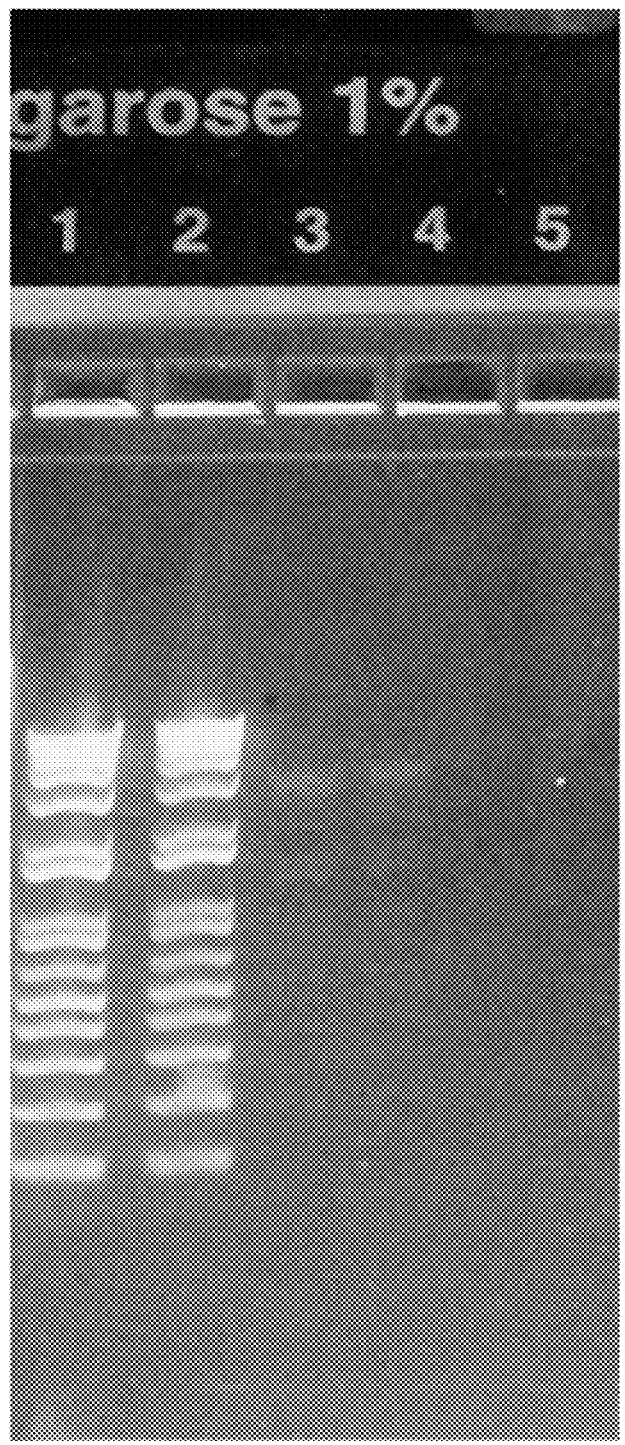
FIG. 8 shows the results of 1% agarose gel electrophoresis of model plasma enriched with cfDNA prior and following the volume adsorption test. Lane 1 is model plasma enriched with cfDNA prior to incubation; lane 2 is model plasma enriched with cfDNA following incubation with ethanolamine Sepharose FF control; lane 3 is model plasma enriched with cfDNA following incubation with PDAM; lane 4 is model plasma enriched with cfDNA following incubation with PLLAM; lane 5 is model plasma enriched with cfDNA following incubation with H1.3 affinity matrix.
Figure 9:
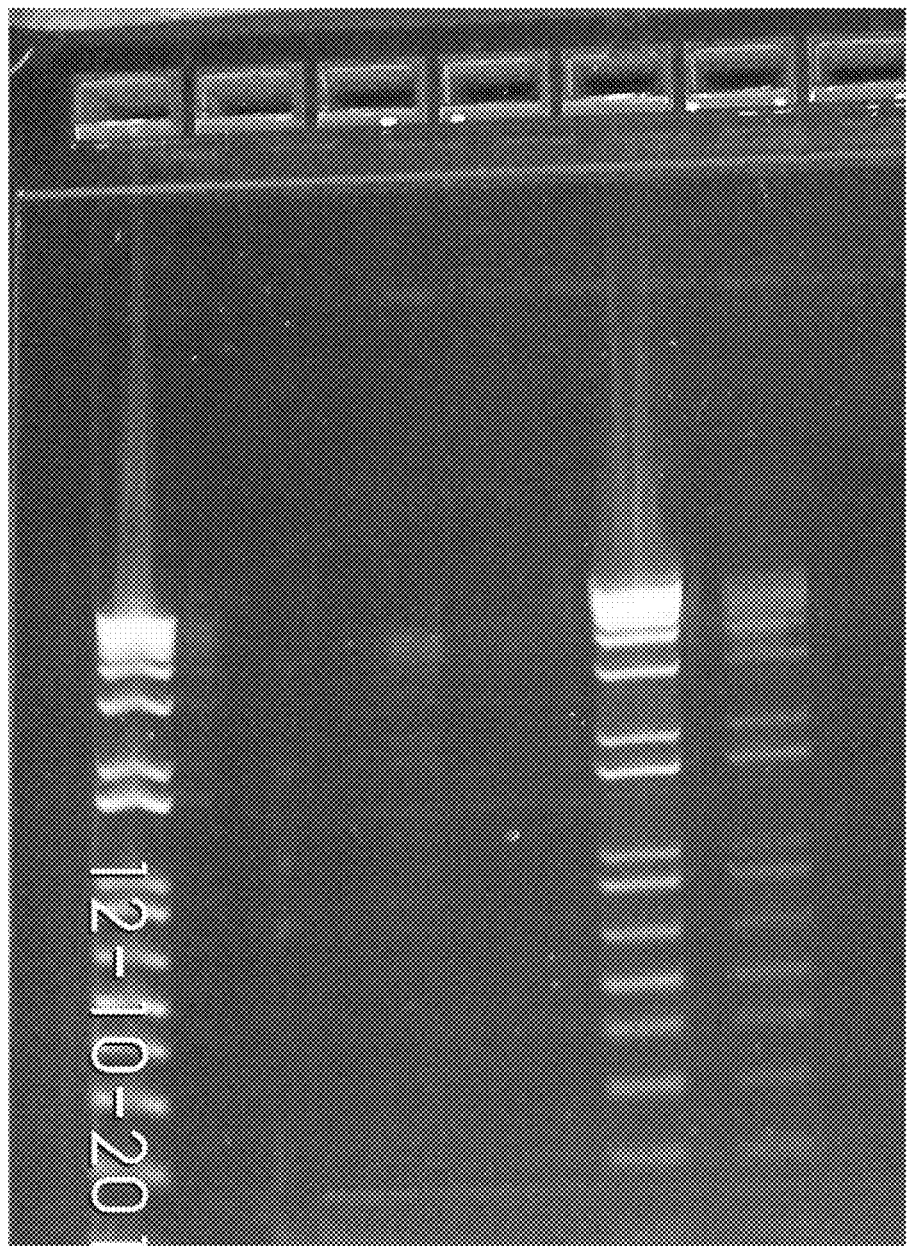
FIG. 9 shows the results of 1% agarose gel electrophoresis of plasma of the patient diagnosed with odontogenic-related sepsis prior to and following the volume adsorption test. Lane 1 is plasma of the patient with odontogenic-related sepsis following incubation with ethanolamine Sepharose FF control; lane 2 is distilled water blank line; lane 3 is plasma of the patient with odontogenic-related sepsis following incubation with H1.3 affinity matrix; lane 4 is distilled water blank line; lane 5 is plasma of the patient with odontogenic-related sepsis following incubation with PDAM; lane 6 is plasma of the patient with odontogenic-related sepsis following incubation with PLLAM.

It appears that poly-L-lysine affinity matrix (PLLAM), PAMAM dendrimer affinity matrix (PDAM) and histone H1 affinity matrix have equal capacity to remove model cfDNA from model plasma enriched with cfDNA, but histone H1 affinity matrix is significantly superior in removing cfDNA from patient plasma. This finding was confirmed by electrophoretic analysis of the samples (see FIGS. 8 and 9).

The volume adsorption test of model plasma enriched with cfDNA with poly-L-lysine affinity matrix (PLLAM), PAMAM dendrimer affinity matrix (PDAM) and histone H1 affinity matrix yielded almost the same electrophoretic picture with marginal cfDNA content.

The volume adsorption test of patient plasma with PLLAM, PDAM and hi stone H1 affinity matrix yielded a different electrophoretic picture with marginal cfDNA content following incubation with histone H1 affinity matrix but meaningful cfDNA content following incubation with PLLAM affinity matrix and PDAM affinity matrix.

Example 22: Model for Evaluating the Effects of a Use of Apheresis Device(s) on Adoptive T-Cell Therapies To establish a model to evaluate the effects of use of apheresis device(s) of the present disclosure on adoptive T-cell therapies, a total of 12 female Oncopig cancer model pigs are used. For the study design, a first group of Oncopigs (n=6) receiving a 3-day sequential infusion of ascending doses of MM25b mouse DNase I mut_P2A_H3scFvCAR T cells combined with treatment comprising application of apheresis device(s) disclosed herein (e.g., apheresis device(s) configured to remove neutrophil extracellular traps [NETs]) is compared to a second group of Oncopigs (n=6) receiving a 3-day sequential infusion of ascending doses of MM25b mouse DNase I mut_P2A_H3scFvCAR T cells alone. The endpoints for evaluation are determined as the pharmacokinetic and functional activity of CAR-T cells in the blood of the Oncopig; drug limit toxicity (DLT) and adverse events (AE); and tumor histology and immunogram.

For the Oncopig cancer model, all research procedures are conducted in compliance with the Guide for the Care and Use of Laboratory Animals. 12 female Oncopigs (obtained from the Sus Clinicals) are transgenic pigs with Cre-recombinase-inducible heterozygous $TP53R^{167H}$ and $KRAS^{G12D}$ mutations. R167H is a dominant-negative mutation of the TP53 tumor suppressor gene, and G12D is an activating mutation of the KRAS oncogene (see, e.g., Overgaard et al., Front. Immunol., June 2018, vol. 9, art. 1301).

Animals are maintained in pens with aspen-chip contact bedding (PWI Industries Canada, Quebec, Canada), fed a grower chow (#5081, PMI, St Louis, MO), and provided water ad libitum. Animal room temperature is 21.5±1° C., relative humidity is 30%-70%, and light: dark photoperiod is 12:12 hours. All procedures and imaging are performed under general anesthesia, with peri-operative analgesia.

Tumor induction is performed when the pigs are 12-22 weeks old. An 18-gauge core biopsy of the pancreas is obtained under CT guidance, using co-axial technique (Temno Evolution, Merit Medical, South Jordan, UT). $TP53^{R167H}$ and $KRAS^{G12D}$ expression is induced by incubating the core biopsy with an adenoviral vector carrying the Cre recombinase gene ($10^9$ pfu Ad5CMVCre-eGFP, University of Iowa Viral Vector Core) for 20 minutes at room temperature, in phosphate-buffered saline (PBS) containing 15 mM calcium chloride (total fluid volume of 1 ml). Gelatin sponge (Gelfoam, Pfizer) is then added using a 3-way stopcock, and the mixture (virus, core biopsy, gelatin) is injected percutaneously back into the duodenal or splenic lobe of the pancreas, through the biopsy needle, which is kept in place after the biopsy. As pigs possess a ring-shaped pancreas with 3 lobes: duodenal, splenic, and connecting, the duodenal lobe may be referred to herein as the "head" of the pancreas, and the splenic lobe as the "tail."

Figure 14:
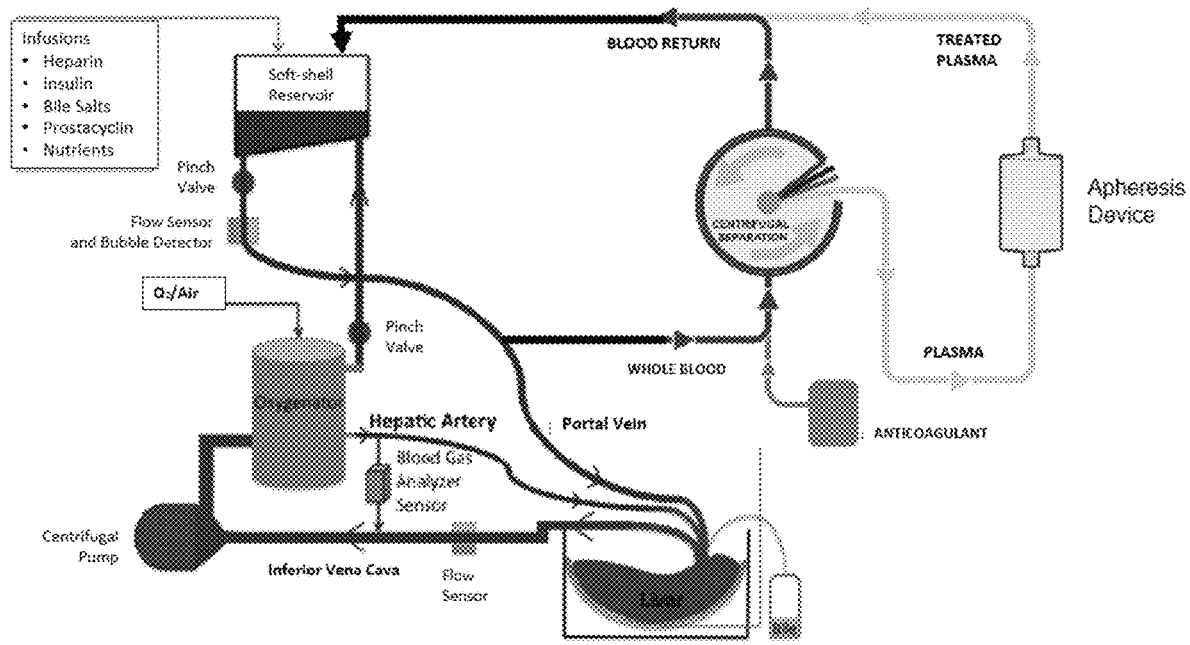
FIG. 14 shows the experimental setup for evaluating the effects of the use of NucleoCapture device(s) (H1.3 histone affinity matrix) for preserving organ transplant during ex vivo perfusion of pig livers subjected to Metra normothermic machine perfusion. The circuit of Terumo Spectra Optia system is integrated into the portal vein line of OrganOx Metra® perfusion device for machine-based perfusion of livers. Group SCS: 3 livers subjected to 6 hours of cold storage followed by 6 hours of reperfusion with allogeneic porcine blood; Group NMP: 3 livers subjected to 6 hours of Metra normothermic machine perfusion with autologous blood followed by 6 hours of reperfusion with allogeneic porcine blood; Group NMP_NC: 3 livers subjected to 6 hours of Metra normothermic machine perfusion with Metra perfusion solution and use of apheresis device(s) of the present invention during NMP stage followed by 6 hours of reperfusion with allogeneic porcine blood; Group RP_NC: 3 livers subjected to 6 hours of Metra normothermic machine perfusion with Metra perfusion solution followed by 6 hours of reperfusion with allogeneic porcine blood solution and use of apheresis device(s) during reperfusion stage.

Example 23: Evaluation of the Effects of Using Apheresis Device(s) to Preserve Organ Transplant During Ex Vivo Perfusion To establish a model to evaluate the effects of using apheresis device(s) of the present disclosure to preserve organ transplant during ex vivo perfusion, a total of 12 pig livers were used in an established abbatoir porcine model of donation after circulatory death (DCD). Livers subjected to Metra normothermic machine perfusion (NMP) were combined with the use of apheresis device(s) disclosed herein according to the experimental setup shown in FIG. 14. Group SCS: three livers subjected to 4-5 hours of ice box cold storage followed by 6 hours of reperfusion with allogeneic whole porcine blood. This group represents the current standard of care in clinical organ transplantation. Group NMP: three livers subjected to 4-5 hours of cold storage followed by Metra normothermic machine perfusion for 6 hours with Metra perfusion solution (autologous leukodepleted blood cell fraction mixed with crystalloid solution, hematocrit 40%). The liver was then flushed with cold University of Wisconsin solution (UW) and this was followed by 6 hours of normothermic machine reperfusion with allogeneic porcine whole blood to simulate clinical liver reperfusion injury; Group NC_NMP: three livers subjected to 4-5 hours of cold storage followed by 6 hours of Metra normothermic machine perfusion with Metra perfusion solution and concurrent use of NucleoCapture apheresis device(s) (H1.3 histone affinity matrix) of the present disclosure (see Example 26) during the initial NMP stage followed by 6 hours of reperfusion with allogeneic porcine whole blood; Group NMP_NC: three livers subjected to 4-5 hours of cold storage followed by 6 hours of Metra normothermic machine perfusion with Metra perfusion solution followed by 6 hours of normothemic machine reperfusion with allogeneic porcine whole blood and concurrent use of NucleoCapture apheresis device(s) during the reperfusion stage.

The primary endpoint for evaluation was the level of lactate in perfusate. Lactate is widely accepted as a critical marker to assess liver viability during NMP (see, e.g., Nostedt et al., PLoS ONE, 2019, 148):e0220786). Lactate in the perfusate is used to evaluate the severity of hypoxia-induced hepatocyte dysfunction. cfDNA in perfusate was quantified using Nu.Q® H3.1 assay (see, e.g., Dolan et al., BMC Veterinary Research, 2021, vol. 17, art. 276).

For the liver setup for perfusion, the suprahepatic inferior vena cava (IVC) was prepared first by excising attached diaphragmatic tissue and oversewing the orifices of the phrenic veins, and was then closed using a linear vascular stapler (Covidien, Hampshire, UK). The infrahepatic IVC was cannulated (28F Sorin, Gloucester, UK). The hepatic hilum was dissected, taking care to ligate all tributaries. Cannulae were secured in the portal vein (24F Sorin), celiac artery (10F Sorin), and common bile duct (12-18Fr Summit Medical, Cheltenham, UK). The liver was flushed with 500 mL colloid solution (Gelofusine®, B Braun, South Yorkshire, UK) to remove preservation solution, and then transferred to the perfusion device.

Figure 10:
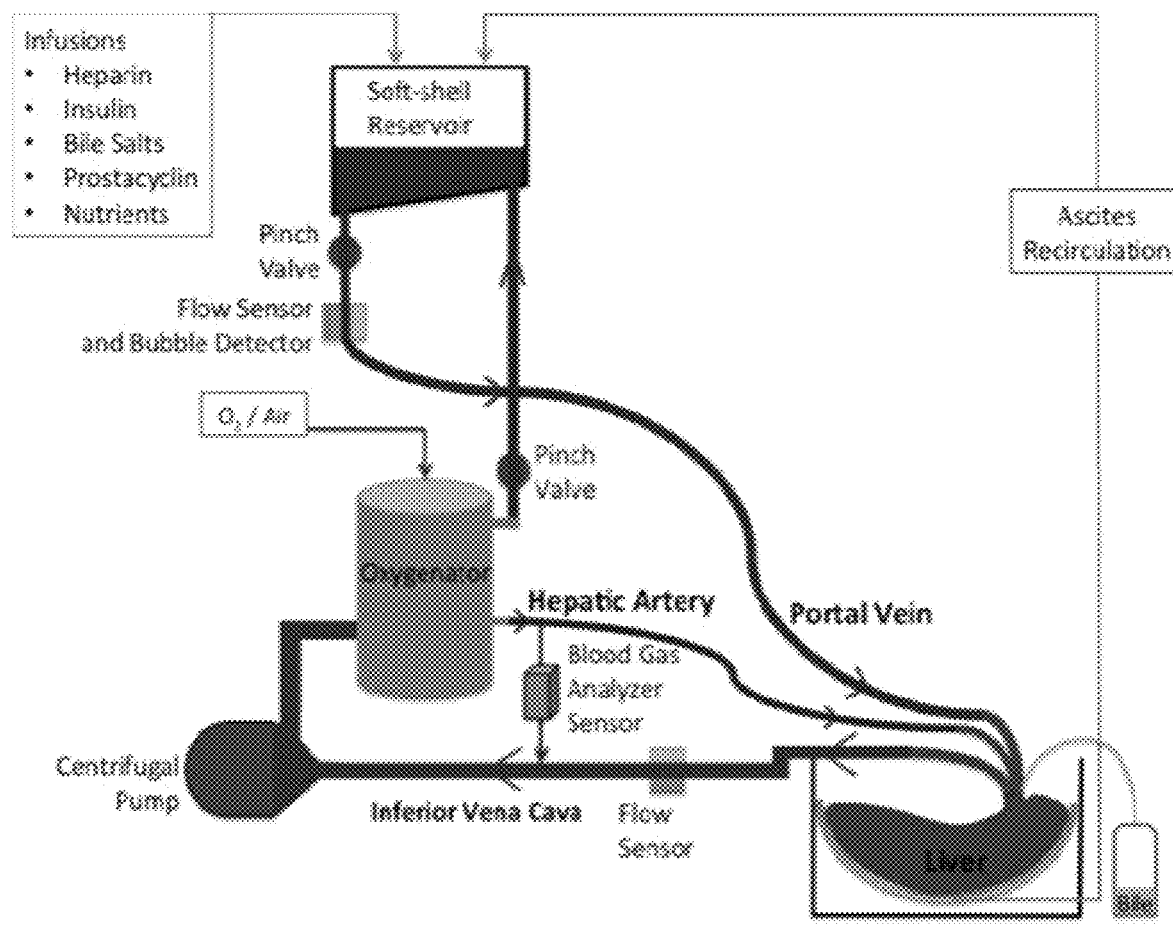
FIG. 10 shows an exemplary schematic representation of an OrganOx Metra® perfusion circuit.

The OrganOx Metra® perfusion device (OrganOx Limited, UK), as exemplified in FIG. 10, was used for machine-based perfusion of livers. OrganOx Metra® provides automated pumping, oxygen/air delivery, and heat exchange, in order to maintain the perfusate at normal temperature, within physiological ranges for $pO_2$, $pCO_2$, pH, and at physiological pressures in the vascular inflows and outflow of the liver (hepatic artery pressure 60 to 75 mmHg; IVC pressure (1 to 2 mmHg). The portal pressure did not require monitoring as it was effectively fixed by the height of the portal venous reservoir, and portal flow was continuously measured. Hemodynamic parameters and blood gas data were continuously recorded during preservation. Cannulation of the bile duct enables collection and automated monitoring of hourly bile production. The machine also continuously infused (i) bile salt (sodium taurocholate, New Zealand Pharmaceuticals, Palmerston North, New Zealand); (ii) insulin (Actrapid®, Novo Nordisk, West Sussex, UK); (iii) heparin (CP Pharmaceuticals, Wrexham, UK); (iv) prostacyclin (Flolan®, Glaxo, Middlesex, UK). A variable rate infusion of glucose and amino acids (Nutriflex, B Braun, Shef-field, UK) was regulated by 4-hourly manually inputted glucose levels.

The device was primed with three units of packed red blood cells, sourced from the donor, and one unit of colloid solution (Gelofusine®, B Braun), with addition of calcium gluconate (B Braun), heparin (CP Pharmaceuticals), cefuroxime (GSK), and 30 mL of sodium bicarbonate (B Braun). During priming, the perfusate was allowed to reach operating conditions: temperature (37° C.); $pO_2$ (12 kPa); $pCO_2$ (5 kPa); and pH (pH 7.35). The cannulated organ was then connected, and blood flow started. Once perfusion was established, minor bleeding points were controlled surgically, and the liver container was then closed.

The graphs representing the lactate levels in the perfusate during initial perfusion and reperfusion stage in 4 experimental groups are presented in FIGS. 15A-B. The graph representing cfDNA content (in ng/ml as measured by the Nu.Q® H3.1 assay) in perfusate during NMP stage is presented in FIG. 15C (mean values with SEM bars shown). The graph representing cfDNA content (ng/ml) in circuit during reperfusion stage is presented in FIG. 15D.

The data demonstrate that the use of apheresis device(s) disclosed herein significantly decrease level of cfDNA in an extracorporeal circuit when the device is used either in initial NMP or in reperfusion phase.

It follows from the reduced lactate levels that the use of apheresis device(s) disclosed herein significantly protects liver during the NMP phase and almost completely prevents reperfusion liver injury which constitutes the main source of morbidity and mortality after orthotopic liver transplantation (OLT).

Figure 11:
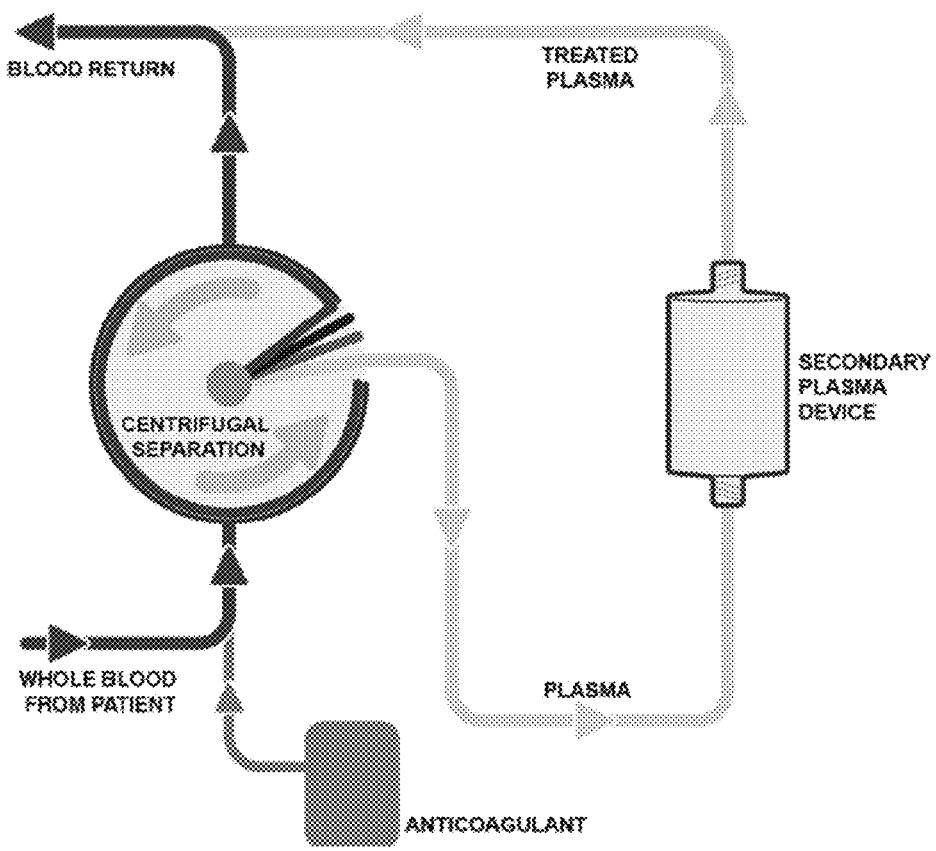
FIG. 11 shows an exemplary schematic representation of an extracorporeal circuit comprising an apheresis device. The apheresis device may comprise affinity matrices that may be placed in various affinity columns. As an example, such column(s) may be used as an additional plasma device in an extracorporeal circuit, e.g., a plasma circuit that may comprise a commercially available Terumo Spectra Optia Apheresis system (SPO, Terumo BCT, Lakewood, CO, USA). In certain aspects, column(s) disclosed herein may be integrated into the extracorporeal circuit downstream from where the plasma is separated into the secondary plasma device position of the circuit, as shown.

Example 24: Apheresis Columns for Use in Extracorporeal Circuits to Preserve Organ Transplant During Ex Vivo Perfusion In this study, the apheresis column(s) of the present disclosure including, for example, apheresis device(s) configured to remove neutrophil extracellular traps (NETs) (e.g., NucleoCapture device as described in Example 26), comprise a plasma device in an extracorporeal circuit, such as that exemplified in FIG. 11. The extracorporeal plasma circuit may additionally comprise, e.g., a commercially available Terumo Spectra Optia system (SPO, Terumo BCT, Lakewood, CO, USA). The apheresis column(s) can be integrated into the extracorporeal circuit, for example, downstream from where the plasma may be separated, and into the Secondary Plasma Device (SPD) position of the circuit. The circuit of Terumo Spectra Optia system is integrated into the portal vein line of the OrganOx Metra® perfusion device for machine-based perfusion of livers. Capture of NETs during ex vivo transplant storage and reperfusion using extracorporeal circuits leads to superior organ utilization and improves clinical outcomes (see Example 26). Alternatively, the apheresis column described in Example 25 can be integrated directly into the blood circuit of the OrganOx Metra® or any other organ support system without concomitant use of a plasma separation machine.

Example 25: Plasma-Filter Type Hollow-Fiber Affinity Cartridge for Use in Whole Blood Circuit The histone H1.3 affinity matrix was prepared as specified in Example 1. 50 mL of histone H1 affinity matrix was loaded into the plasma compartment of a commercial Plasmaflo filter 80W/L (Asahi Kasei Medical Co., Ltd., Japan) which contains a plasma separation membrane of 0.5 µm pore size (FIG. 13). After the filling of the plasma compartment of the filter with of histone H1 affinity matrix the inlet and outlet ports of plasma compartment were stopped tightly.

Figure 12:
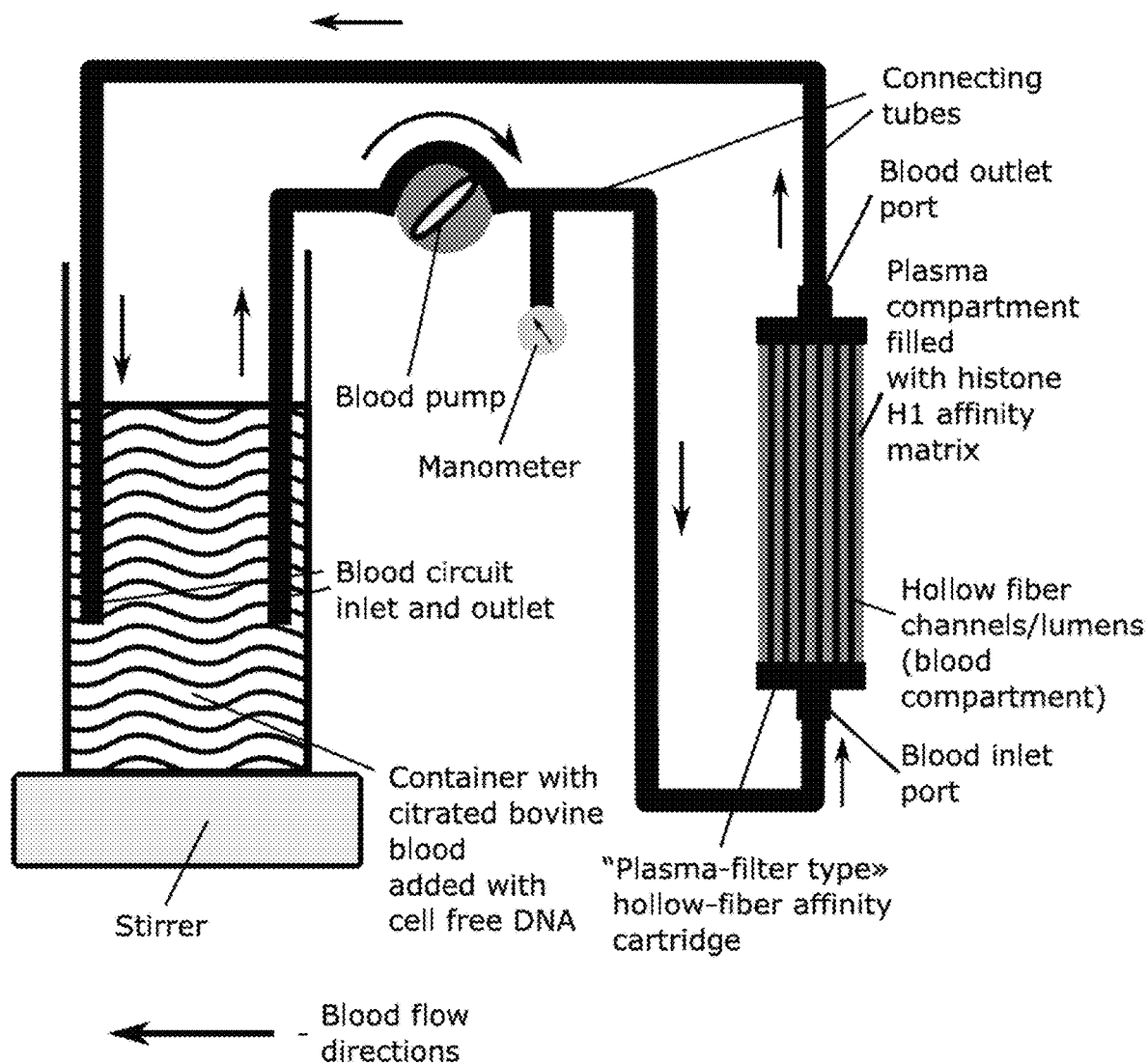
FIG. 12 shows ex vivo hemoperfusion circuit formed by connecting the prepared "plasma-filter type" hollow-fiber histone H1 affinity cartridge via blood inlet and outlet ports, correspondingly, to a polyvinylchloride tube and a peristaltic pump. The inlet and outlet of the blood circuit are fixed to opposing sides of a container. Blood samples are collected from inlet and outlet blood at different time points during a perfusion cycle.

Ex vivo hemoperfusion was performed through a circuit formed by connecting the prepared "plasma-filter type" hollow-fiber affinity cartridge via blood inlet and outlet ports, correspondingly, to a polyvinylchloride tube and a peristaltic pump. The inlet and outlet of the blood circuit were fixed to opposing sides of a container with 450 ml of fresh citrated (ACD) whole bovine blood added with of Salmon sperm DNA (Sigma) up to the concentration of 20

μg/mL, as a model analogue of blood cfDNA. The solutions were stirred (190 r/min) continuously throughout the experiments (see FIG. 12). A perfusion through the circuit was performed at a flow rate of 100 mL/min and blood samples were collected from inlet and outlet blood at different time points during a 200 min perfusion cycle. Inlet pressure was 30 mmHg upon start of the procedure and 40 mmHg by the end of the procedure. The blood samples were analyzed for cfDNA content using Qubit® 3.0 Fluorometer and Qubit™ dsDNA assays (both of Thermo Fisher Scientific) according to the manufacturer's instructions.

The content of cfDNA in blood during the perfusion is represented in the diagram shown in FIG. 16.

Thus, an apheresis column, i.e., "plasma-filter type" hollow-fiber affinity cartridge for use in a whole blood circuit efficiently selectively captured cfDNA from blood (as evidenced by the difference in cfDNA content in inlet and outlet blood) without capturing other blood components, and almost completely eliminated cfDNA from blood by the end of the perfusion session.

Example 26: Model for Evaluation of the Effects of Using Different Apheresis Devices on Blood cfDNA Levels in Large Animals The performance of apheresis column(s) of the present disclosure to eliminate cfDNA (cfDNA) from blood during extracorporeal procedure was studied in a porcine model of septic shock. This study included healthy Swedish landrace breed piglets. Ethical approval was obtained from the Animal Ethics Committee in Uppsala, Sweden. The study was conducted in accordance with the Guide for the Care and Use of Laboratory Animals and was reported in compliance with the ARRIVE guidelines. A schematic of the study protocol is provided below.

| E. coli i.v. infusion | | | | | | | | |
|---|---|---|---|---|---|---|---|---|
| | | | | Apheresis | | | | |
| Time | 0 h | 1 h | 2 h | 3 h | 4 h | 5 h | 6 h | 7 h |
| Sampling | x | x | x | x | x | x | x | x |

A. Apheresis Column for Use in Plasma Circuit Containing H1.3 Affinity Matrix (NucleoCapture Device)

The human recombinant histone protein H1.3 was produced by fermentation of E. coli B121(DE3)pEGT1/H1.3. The histone H1.3 protein was isolated from disintegrated bacterial cells by extraction. Purification was carried out in three successive stages of chromatography including cation-exchange, reverse phase and gel-permeation. Cross-linked agarose beads were activated with 0.4% sodium metaperiodate for 2 hrs. After washing with water for injection and a 0.2 M borate buffer, the suspension activated agarose beads were incubated with ligand solution for 2.5 hours. Once the immobilization was complete, the solution with unbound ligand was removed and the suspension of the beads was washed with a 0.2 M borate buffer. The remaining activity of the beads was blocked for 15 min with 0.3% sodium borohydride. The suspension of the agarose beads bind histone protein H1.3 and was washed several times with water and 0.9% sodium chloride injections. The sterile suspension of beads with immobilized ligand was filled into the column by aseptic processing.

The column housing measures 135.0±5.0×61.5±1.0 mm and weighs 265±6 g. The volume of the column is 150±2 ml and the volume of the matrix is 100±10 ml. The housing has two filters that provide free flow of fluid and plasma through the column and keep the matrix inside. The threaded caps on both sides of the housing have fittings with standard Luer-Lock connectors for connection to the extracorporeal lines of a plasma separator (see FIG. 17).

The standard Luer-Lock connectors ensure that the column is compatible with the most widely used plasma separators. The lines to the plasma separation equipment can have connectors of two different diameters. If the column cannot be directly connected to the plasma line, the adapter that is provided with the column must be used.

20 animals aged weighing between 41.9-50.7 kg were considered to be randomly assigned (2:1:1) to one of three groups; NucleoCapture device treatment (n=10); Sham A column treatment (n=5) and Sham B column treatment. (n=5).

The Escherichia coli strain B09-11822 (serotype O rough: K1:H7; Statens Seruminstitut, Copenhagen, Denmark), a serum resistant, clinical isolate was used. Before the experiment, the bacteria are grown to logarithmic growth phase in lysogeny broth medium. At 0 hour, an infusion of 8.62±0.19 $\log_{10}$ colony forming units in 20 mL normal saline is started at a constant infusion rate for 3 hours via a central venous catheter. The columns (Device, Sham A and Sham B, accordingly) were used in the plasma circuit of the commercial Terumo Spectra Optia system (SPO, Terumo BCT, Lakewood, CO, USA) which is developed and approved for cytopheresis, plasmapheresis and plasmasorption in the human clinical setting.

Plasma samples were sampled at 3, 4, 5, 6, and 7 hours from the plasma circuit inlet (prior to passage through the NucleoCapture or sham column) and outlet (after passage through the NucleoCapture or sham column). Quantity of cfDNA were assayed using quantitative qRT-PCR with two different genomic primers (HK2 and β-globulin) and two ELISA assays: Nu.Q™ H3 Assay Kit, a sandwich ELISA designed for quantification of circulating nucleosomes via detection of canonical H3.1 (VolitionRx) and by H3R8cit Assay, a sandwich ELISA designed for quantification of circulating nucleosomes via detection of citrullinated histone H3.1 (VolitionRx).

NucleoCapture columns showed a prominent ability to bind plasma cfDNA and NETs. Analysis of concentrations of the genomic cfDNA (qPCR) and surrogate indicators of NETs (plasma canonical and citrullinated histones H3) in plasma sampled before and after its passage through the NucleoCapture column at different time points showed that a single pass of plasma through NucleoCapture resulted in removal of 83-100% of cfDNA/NETs at various time-points (see Tables 11 and 12).

Analysis of plasma samples with the High Sensitivity DNA assay on a Bioanalyzer system before and after its passage through the NucleoCapture column indicates peaks corresponding to all types of cfDNA completely disappeared after a single pass of plasma through NucleoCapture column (FIG. 18A—plasma prior to passage through NucleoCapture column (cfDNA of various molecular weight present in plasma); FIG. 18B—plasma after passage through Nucleo-Capture column (no cfDNA detected)).

TABLE 11

Levels of cfDNA measured with qPCR in PRE- and POST- column plasma samples, ng × mL$^{-1}$,
Mean (SD); Changes of the analytes concentration, % recalculated on the basis of individual data.

| | | Analyte | | | | | |
|---|---|---|---|---|---|---|---|
| | | Genomic cfDNA level measured with qPCR (HK2) | | Genomic cfDNA level measured with qPCR (β-globulin) | | Mitochondrial cfDNA level measured with qPCR (NADH6) | |
| Time point | Group | Nucleo | Sham (A + B) | Nucleo | Sham (A + B) | Nucleo | Sham (A + B) |
| 3 h | N | 9 | 9 | 9 | 9 | 9 | 9 |
| | PRE | 3.5 (1.92) | 4.0 (2.43) | 2.8 (1.53) | 4.1 (2.45) | 1.8 (0.59) | 1.5 (0.69) |
| | POST | 1.1 (3.02) | 4.8 (2.67) | 0.1 (0.07) | 4.0 (1.73) | 1.3 (0.74) | 1.7 (0.73) |
| Change, % | | −64.5 (103.33)** | 41.4 (86.93) | −97.9 (2.93)* | −9.6 (41.31) | −24.9 (46.38) | 37.9 (75.56) |
| 4 h | N | 9 | 9 | 9 | 9 | 9 | 9 |
| | PRE | 5.6 (3.48) | 8.2 (3.71) | 5.0 (3.27) | 6.5 (2.04) | 2.0 (1.03) | 1.4 (0.69) |
| | POST | 0.2 (0.31) | 9.9 (5.13) | 0.2 (0.22) | 7.7 (3.79) | 1.1 (0.29) | 1.4 (0.57) |
| Change, % | | −95.7 (4.21)* | 33.3 (64.78) | −95.7 (3.16)* | 16.0 (22.73) | −31.0 (33.19) | −6.6 (31.75) |
| 5 h | N | 9 | 9 | 9 | 9 | 9 | 9 |
| | PRE | 7.1 (6.13) | 12.0 (4.69) | 5.4 (3.87) | 9.6 (4.27) | 1.2 (0.39) | 1.6 (0.66) |
| | POST | 0.0 (0.04) | 12.9 (7.11) | 0.1 (0.04) | 9.0 (4.27) | 0.3 (0.15) | 1.4 (0.46) |
| Change, % | | −99.9 (0.24)* | 5.7 (23.41) | −97.9 (2.57)* | 6.5 (13.30) | −72.4 (14.27)* | −0.2 (40.14) |
| 6 h | N | 9 | 7 | 9 | 7 | 9 | 7 |
| | PRE | 8.5 (7.24) | 18.7 (8.32) | 5.2 (3.58) | 11.8 (3.09) | 1.4 (0.68) | 1.6 (0.71) |
| | POST | 0.1 (0.07) | 15.8 (5.45) | 0.1 (0.06) | 12.3 (5.70) | 0.8 (0.33) | 1.4 (0.41) |
| Change, % | | −98.5 (1.65)** | −5.6 (38.37) | −96.9 (3.62)* | 3.9 (29.29) | −31.8 (42.50) | −0.6 (35.37) |
| 7 h | N | 9 | 7 | 9 | 7 | 9 | 7 |
| | PRE | 5.9 (6.36) | 21.1 (13.67) | 3.7 (4.10) | 14.5 (5.85) | 1.1 (0.48) | 1.7 (1.38) |
| | POST | 0.5 (1.02) | 20.6 (15.25) | 0.1 (0.12) | 13.7 (6.54) | 1.1 (0.5) | 1.4 (0.63) |
| Change, % | | −47.6 (123.61)** | −1.5 (32.77) | −85.8 (35.30)** | 7.8 (25.67) | −89.1 (281.89) | −6.9 (76.43) |

TABLE 12

Levels of H3 and CitH3 in PRE- and POST- column plasma samples, ng × mL$^{-1}$, Mean (SD); Changes of the analytes concentration, %

| | | Analyte | | | | | |
|---|---|---|---|---|---|---|---|
| | | Canonical H3 level (NuQ kit) | | CitH3 measured ([H3R8cit] ELISA) | | CitH3 level ([H3PanCit] ELISA) | |
| Time point | Group | Nucleo | Sham (A + B) | Nucleo | Sham (A + B) | Nucleo | Sham (A + B) |
| 3 h | N | 9 | 9 | 9 | 9 | 9 | 9 |
| | PRE | 65.7 (25.53) | 82.9 (38.61) | 5.7 (2.5) | 4.8 (1.56) | 6.6 (3.47) | 5.1 (1.14) |
| | POST | 2.2 (0.66) | 80.1 (39.65) | 0.1 (0.12) | 4.5 (1.55) | 1.1 (0.48) | 4.9 (1.03) |
| Reduction. % | | −96.0 (2.29)* | −4.6 (15.69) | −97.5 (1.59)* | 6.9 (13.14) | −79.0 (14.21)* | 1.8 (15.49) |
| 4 h | N | 9 | 9 | 9 | 9 | 9 | 9 |
| | PRE | 98.8 (54.14) | 152.8 (48.36) | 10.6 (6.91) | 10.3 (4.89) | 10.6 (6.59) | 10.2 (7.8) |
| | POST | 3.1 (1.62) | 148.3 (44.6) | 0.2 (0.22) | 10 (4.19) | 1.2 (0.55) | 10 (6.91) |
| Reduction. % | | −96.0 (2.59)* | −2.5 (8.94) | −97.5 (1.65)* | 0.2 (17.02) | −86.7 (6.40)* | 1.1 (12.79) |
| 5 h | N | 9 | 7 | 9 | 7 | 9 | 7 |
| | PRE | 121.3 (93.69) | 230.8 (99.47) | 14.3 (13.72) | 14.3 (6.8) | 13.0 (9.39) | 12.5 (7.96) |
| | POST | 1.7 (93.69) | 232.8 (76.94) | 0.1 (0.04) | 14.9 (7.43) | 0.7 (0.29) | 13 (9.27) |
| Reduction. % | | −97.7 (1.95)* | 4.4 (15.15) | −99.0 (1.14)* | −3.5 (16.59) | −91.7 (6.60)* | −0.3 (14.62) |
| 6 h | N | 9 | 7 | 9 | 7 | 9 | 7 |
| | PRE | 123.1 (85.31) | 298.2 (103.5) | 12.9 (11.15) | 14.4 (6.74) | 12.0 (7.72) | 12.1 (7.33) |
| | POST | 2 (1.18) | 303 (99.24) | 0.1 (0.11) | 15.4 (7.09) | 0.8 (0.33) | 12.9 (7.67) |
| Reduction. % | | −97.8 (1.72)* | 3.3 (12.25) | −99.0 (0.96)* | −7.9 (14.58) | −91.1 (7.39)* | −7.0 (11.57) |
| 7 h | N | 9 | 7 | 9 | 7 | 9 | 7 |
| | PRE | 143.0 (138.97) | 368.0 (153.94) | 12.4 (11.33) | 15.9 (8.78) | 10.3 (7.22) | 11.8 (8.98) |
| | POST | 2.4 (2.08) | 378.0 (143.6) | 0.1 (0.1) | 16.9 (9.21) | 0.7 (0.47) | 13.3 (11.43) |
| Reduction. % | | −98.0 (1.33)* | 5.8 (16.17) | −99.1 (0.79)* | −13.3 (24.66) | −90.3 (7.29)* | −9.7 (19.95) |

Example 27: Generation of cfDNA in Isolated Organ Perfusion Systems

It is known that the majority (up to 90%) of cfDNA in systemic blood is generated by blood cells and in particular by neutrophils, which are the most prevalent blood cell fraction. (see, e.g., Lui Y Y, Chik K W, Chiu R W, Ho C Y, Lam C W, Lo Y M. Predominant hematopoietic origin of cell-free DNA in plasma and serum after sex-mismatched bone marrow transplantation. Clin Chem. 2002 March; 48(3):421-427). It is known that highest levels of cfDNA in blood so far were reported in patients with severe sepsis, septic shock and COVID-19 due to overactivation of the innate immune response and mobilization of neutrophils in these clinical settings. When measured with the Nu.Q® H3.1 assay the maximum reported cfDNA level was 24 000 ng/ml in septic shock patients with median cfDNA levels of 1000 ng/ml in cohort of sepsis patients and 2700 ng/ml cfDNA in cohort of COVID-19 patients.

We have studied cfDNA levels in liver perfusate using porcine after cardiac death (DCI)) liver model (WIT=<30 mins, CIT 4-5 hours). After procurement, flushing and static cold storage in UW®solution for transport, livers were prepared on the back bench and fully cannulated. N=9 livers were perfused on the OrganOx Metra® device as standard, with the perfusate composed of autologous leukodepleted blood for 6 hours. cfDNA level was quantified hourly in perfusion solution using Nu.Q® H3.1 assay. The data is presented in FIG. 19.

Surprisingly, despite the fact that the perfusion solution was leukocyte free, there was a substantial growth of cfDNA quantity in perfusate with levels approaching 80 000 ng/ml by 6 hours of perfusion. This is a very high cfDNA level as it is 50-100 fold higher than cfDNA level in blood of patients with severe COVID-19 sepsis. Thus, even a modest removal of one or more cell free DNA (cfDNA) types selected from nucleosome-bound cfDNA, exosome-bound cfDNA, and unbound cfDNA from an organ perfusion solution, wherein said organ is perfused extracorporeally can provide extraordinary benefit for donor organ health.

Example 28: Preparation of Affinity Matrixes for Apheresis of Organ Perfusion Solution 4FF-H1.3 matrix. Human recombinant histone protein H1.3 was produced by fermentation of *E. coli* B121(DE3) pEGT1/H1.3. The protein was isolated from disintegrated bacterial cells by extraction. Purification was carried out in three successive stages of chromatography including cation-exchange, reverse phase and gel-permeation. Cross-linked agarose beads were activated with 0.4% sodium metaperiodate for 2 hrs. After washing with water for injection and a 0.2 M borate buffer, the suspension of activated agarose beads was incubated with H1.3 solution for 2.5 hours. Once the immobilization was complete, the solution with unbound ligand was removed and the suspension of the beads was washed with a 0.2 M borate buffer. The remaining activity of the beads was blocked for 15 min with 0.3% sodium borohydride. The suspension was washed several times with 0.9% sodium chloride.

4FF-anti 113.1 IgG matrix. Antibody against histone H3.1 was obtained from Merck Millipore (MABE952). Anti H3.1 antibody tightly binds the nucleosome core particle and therefore can capture nucleosomes and chromatin. 5 mL of highly cross-linked N-hydroxysuccinimide (NETS) activated 4% agarose, beads (NETS-activated Sepharose 4 Fast Flow, GE Healthcare Life Sciences) were used. The activated matrix was washed twice with cold (2-4° C.) coupling buffer (0.2 M NaHCO$_3$, 0.5 M NaCl, pH 8.3). 1000 µg of anti H3.1 antibodies were dialyzed against coupling buffer and then coupled according to the manufacturer's procedure to NETS activated Sepharose. Three cycles of washing with coupling buffer followed by 0.1 M acetate buffer (pH 4.0) were used to remove the excess of unbound anti H3.1.

4FF-HMBG1 matrix. Recombinant human HMGB1 protein was obtained from Abcam (ab167718). Cross-linked agarose beads were activated with 0.4% sodium metaperiodate for 2 hrs. After washing with water for injection and a 0.2 M borate buffer, the suspension of activated agarose beads was incubated with H1.3 solution for 2.5 hours. Once the immobilization was complete, the solution with unbound HMBG1 was removed and the suspension of the beads was washed with a 0.2 M borate buffer. The remaining activity of the beads was blocked for 15 min with 0.3% sodium borohydride. The suspension was washed several times with 0.9% sodium chloride.

PDAM matrix. PAMAM dendrimer affinity matrix (PDAM) was prepared as follows. Cellulose beads (Macroporous Bead Cellulose MT 500, particle size 100-250 Iontosorb, Czech Republic) were washed twice with 98% ethanol and distilled water. 1 gram of the beads was incubated with a mixture of 1.0 ml (±)-Epichlorohydrin (Sigma-Aldrich) and 3.0 ml of 2.5 M NaOH. The activating reaction was performed at 40° C. for 2.5 h in a shaker. Activated beads were washed thoroughly with distilled water. The epoxy content of the resins was determined as about 0.31 mmol/g of dry beads by titration of sodium thiosulfate with hydrogen chloride. 4.0 ml of prepared wet activated cellulose beads was suspended with 9.0 ml of 20% solution of amino terminated (—NH$_2$) PAMAM dendrimer (ethylenediamine core, generation 3.0, Sigma-Aldrich) solution and shaken at 24° C. for 5 h. After the modification, unreacted PAMAM was removed by washing with distilled water and the remaining unconverted epoxy groups on the beads were blocked by reacting with ethylamine. The functionalized affinity matrix was then washed with 0.1 M phosphate buffer and MilliQ water.

GNA matrix. 2 mL (1 volume) of Lectin from *Galanthus nivalis* (snowdrop), i.e., GNA (Sigma-Aldrich) solution at a concentration of 10 mg/mL in 0.1M NaHCO$_3$, pH 9.5 was added to 2 mL (1 volume) of CNBr activated agarose beads (Cyanogen bromide-activated-Sepharose 6 MB, 6% agarose, 200-300 µm diameter macrobeads, Sigma-Aldrich) and allowed to react overnight in the cold at pH 7.4-8.0. When the reaction was complete, the lectin coupled agarose was washed extensively with sterile cold phosphate buffered saline (PBS) at pH 7.2-7.4.

Heparin matrix composed of 6% cross-linked agarose beads, functionalized with porcine heparin was purchased from Cytiva (Heparin Sepharose CL-6B). WB-200 4-Methoxybenzaldehyde modified cationic agarose matrix was purchased from Pocard Ltd (Moscow, RF). Polymyxin B-agarose matrix composed of cross-linked 4% beaded agarose with Polymyxin attached through an amino group, with a 1-atom spacer was purchased from Sigma (Sigma Prod. No. P1411).

Example 29: Apheresis of Organ Perfusion Solution with Matrixes Containing Different DNA Binding Polymers To assess the ability of different matrixes to deplete cfDNA from organ perfusate, the perfusion solution samples sampled from circuit of OrganOx Metra® device at 3 hours of NMP (porcine liver perfusion with the perfusate composed of autologous leukodepleted blood cell fraction mixed with crystalloid solution; hematocrit 40%; N=3) were incubated with 10% v/v of different matrixes for 60 min at 37° C. with gentle rotation. Following incubation, the matrixes were pelleted by centrifugation (400 g, 5 min), perfusate was collected, aliquoted and stored at −20° C. until further quantification of cfDNA using Nu.Q® H3.1 assay according to manufacturer's instructions. Table 13, below, shows quantity of cfDNA in perfusate before and after batch chromatography with matrixes based on different DNA binding polymers.

TABLE 13

Quantity of cfDNA in perfusate before and after batch chromatography with matrixes based on different DNA binding polymers.

|  | cfDNA quantity; Nu · Q ™ H3 Assay; ng/ml | | |
| --- | --- | --- | --- |
|  | Sample 1 | Sample 2 | Sample 3 |
| Perfusate before incubation | 92466 | 73536 | 87643 |
| Perfusate after incubation with: | | | |
| 4FF-H1.3 matrix | 10246 | 11030 | 15157 |
| 4FF-anti H3.1 IgG | 38835 | 24266 | 29798 |
| 4FF-HMBG1 | 19417 | 21325 | 28045 |
| CL-6B-heparin | 28658 | 25002 | 35993 |
| WB-200 4-Methoxybenzaldehyde modified | 27740 | 23531 | 28045 |
| WB-200 4-Methoxybenzaldehyde modified + CL-6B-heparin; 50% v/v | 11095 | 13971 | 7011 |
| PDAM | 20342 | 18384 | 21910 |
| GNA | 27739 | 18913 | 24540 |
| Polymyxin B | 32363 | 23531 | 21910 |
| Sepharose 4FF (negative control) | 90692 | 71329 | 85451 |

As shown in Table 13, while certain matrixes have high potency to remove cfDNA from blood and plasma samples (i.e., H1.3 histone matrix, HMBG1 based matrix, anti-histone antibody matrix, PDAM matrix), some others (i.e., 4-methoxybenzaldehyde modified agarose matrix, polysaccharide (heparin based) matrix, GNA based matrix, Polymyxin B based matrix) are much less potent to remove cfDNA from blood and plasma samples. The present inventors therefore hypothesized that components of plasma may inhibit binding of cfDNA to certain classes of DNA binding polymers.

In order to prove the hypothesis, the effect of human plasma on DNA binding capacity of 4-Methoxybenzaldehyde modified agarose matrix, heparin matrix, GNA matrix and Polymyxin B matrix was tested. Perfusion solution samples were diluted with human plasma 50% v/v and tested in batch chromatography experiment as specified above. Table 14, below, shows quantity of cfDNA in perfusate diluted with human plasma before and after batch chromatography with matrixes.

TABLE 14

Quantity of cfDNA in perfusate diluted with human plasma before and after batch chromatography with matrixes.

|  | Sample 1 | Sample 2 | Sample 3 |
|  | cfDNA quantity; Nu.Q ™ H3 Assay; ng/ml | | |
| --- | --- | --- | --- |
| Perfusate before incubation | 47035 | 37023 | 43978 |
| Perfusate after incubation with: | | | |
| CL-6B - heparin | 32424 | 24805 | 34302 |
| WB-200 4-Methoxybenzaldehyde modified | 35276 | 28877 | 32103 |
| GNA | 39979 | 29988 | 34742 |
| Polymyxin B | 39039 | 26877 | 30784 |
| Sepharose 4FF (negative control) | 44918 | 34801 | 43098 |

The data in Table 14 show that plasma inhibits DNA binding capacity of 4-Methoxybenzaldehyde modified agarose matrix, heparin matrix, GNA matrix and Polymyxin B matrix more than 2-fold.

Another unexpected finding was that a combination of two DNA binding polymers, can provide synergy to capture and remove cfDNA. Methoxybenzaldehyde modified agarose is a functionalized cationic polysaccharide which binds DNA via charge-based interactions with negatively charged sugar phosphate DNA backbone while heparin binds to nucleosomes through interaction with the cationic tails of hi stones. Data from Table 13 show superior binding efficiency of 50% v/v mixture of 4-Methoxybenzaldehyde modified agarose and CL-6B—heparin Sepharose versus any of those matrixes taken alone. Thus, combinations of DNA binding polymer matrixes wherein two different DNA binding mechanisms are involved provide substantial synergy to capture and remove cfDNA for the combined matrix.

Based on the provided data, all of the DNA binding polymers specified above, alone or in combination, can be used for efficient removal of cfDNA from an organ perfusion solution, wherein said organ is perfused extracorporeally.

Example 30: Evaluation of the Effects of Using Apheresis Device(s) to Preserve Organ Transplant During Ex Vivo Perfusion in EVLP Model Ex vivo lung perfusion (EVLP) is a novel approach for improvement of quality of previously unacceptable donor lungs and has been used in the successful transplant of lungs maintained on the EVLP system.

We have studied the effect of NucleoCapture device in a porcine gastric acid-induced ARDS model comparing a non-treated group (Lungs with gastric acid-induced ARDS receiving EVLP without NucleoCapture apheresis, n=6) and a treated group (Lungs with gastric acid-induced ARDS receiving EVLP+NucleoCapture apheresis, n=6)

A total of 12 pigs with a mean weight of 50 kg were premedicated with xylazine (Rompun® vet. 20 10 mg/ml; Bayer AG, Leverkusen, Germany; 2 mg/kg) and ketamine (Ketaminol® vet. 100 mg/ml; 11Farmaceutici Gellini S.p.A., Aprilia, Italy; 20 mg/kg). A peripheral intravenous (IV) line was inserted in the earlobe, and a urinary catheter was inserted in the bladder. General anesthesia was accomplished with ketamine (Ketaminol® vet), midazolam (Midazolam Panpharma®, Oslo, Norway) and fentanyl (Leptanal®, Lilly, France) infusions. Mechanical ventilation was established using a Siemens-Elema ventilator (Servo 900C, Siemens, Solna, Sweden). The animals were intubated with a 7.5 size endotracheal tube. Ventilation was adjusted to maintain carbon dioxide levels ($PaCO_2$) between 33-41 mmHg. Tidal volume (Vt) was kept at 6-8 ml/kg. A pulmonary artery catheter (Swan-Ganz CCOmbo V and Introflex, Edwards Lifesciences Services GmbH, Unterschleissheim, Germany) was inserted in the right internal jugular vein and an arterial line (Secalon-TTM, Merit Medical Ireland Ltd, Galway, Ireland) was placed in the right common carotid artery. FIG. 20 shows the overview of the experimental setup. Dihydrostreptomycinsulfate (0.1 ml/kg) (Boehringer Ingelheim Animal Health Nordics A/S, Copenhagen, Denmark) was given subcutaneously before initiation of surgery in all animals.

Induction of ARDS using porcine gastric acid was used to induce an ARDS according to the Berlin criteria. Gastric acid was instilled bronchoscopically into all four lung quadrants. All animals developed hemodynamic instability and required continuous infusion of norepinephrine (40 µg/ml, 0.05-2 µg/kg/min) (Pfizer AB, Sollentuna, Sweden). Fluid loss was compensated with Ringer's acetate (Baxter Medical AB, Kista, Sweden) in all animals. The different ARDS stages were defined according to the Berlin definition using the $PaO_2/FiO_2$ ratio. Mild ARDS was defined as a ratio between 201-300 mmHg, moderate ARDS between 101-200 mmHg, and severe ARDS as <100 mmHg. Animals were confirmed as having ARDS following two separate arterial blood gases falling within the Berlin definition's $PaO_2/FiO_2$ range within a 15-minute interval.

After confirmation of ARDS according to the Berlin definition with two blood gas values 15 minutes apart, a median sternotomy was performed. The pulmonary artery was cannulated via the right ventricle with a 28 F cannula secured by a purse string suture placed in the outflow tract of the pulmonary artery. A clamp was put on the superior vena cava, the inferior vena cava, and on the ascending aorta. The left atrium and inferior vena cava were opened. The lungs were perfused antegradely with 4 L of cold Perfadex® PLUS solution (XVIVO perfusion, Gothenburg, Sweden) distributed at a low perfusion pressure (<20 mmHg). The lungs were harvested en bloc in a standard fashion. The lungs were immersed in cold Perfadex® solution and put in cold storage at 4° C. for 2 hours.

EVLP was performed using Vivoline LS1 (XVIVO perfusion, Gothenburg, Sweden) and the Toronto protocol with a target perfusion of 40% of cardiac output, a tidal volume of 7 ml/kg body weight of the donor, respiratory rate (RR) of 7, 5 cm $H_2O$ PEEP and 21% FiO2 for 4 hours. The system was primed with Steen™ Solution (XVIVO perfusion, Gothenburg, Sweden) and with red blood cells from the donor animal, drawn prior to gastric acid treatment, to reach a hematocrit level of 15-20% in the EVLP circuit. If the perfusate level dropped below 300 ml in the reservoir, additional Steen solution (XVIVO Perfusion) was added. EVLP physiology was recorded hourly during the 4-hour perfusion period.

NucleoCapture apheresis during EVLP

During EVLP, in the NucleoCapture group, the circuit was attached via a veno-venous shunt to a Terumo Optia Spectra apheresis machine containing the NucleoCapture column in the Secondary Plasma Device configuration, aiming to treat 40-60 ml/min of plasma through the column for 4 h.

$PaO_2/FiO_2$ ratio is the ratio of arterial oxygen partial pressure ($PaO_2$ in mmHg) to fractional inspired oxygen ($FiO_2$ expressed as a fraction). P/F ratio is a main clinical indicator of lung functionality. A donor arterial $PO_2/FiO_2$ (P/F ratio) of less than the 300 threshold would frequently result in either exclusion of the donor or placement of the lungs on ex vivo lung perfusion (EVLP). The effect of NucleoCapture apheresis on the outcome of the EVLP procedure measured as final $PO_2/FiO_2$ ratio is presented in FIG. 21.

Thus, NucleoCapture apheresis substantially improves the outcome of EVLP procedure as measured with $PO_2/FiO_2$ ratio.

Macroscopic appearance of lungs treated with EVLP without NucleoCapture apheresis and lungs treated with EVLP and NucleoCapture apheresis are presented in FIG. 22.

Poor lung quality and persistent damage are evident in lungs treated with EVLP without NucleoCapture apheresis while macroscopic appearance of lungs treated with NucleoCapture apheresis was almost close to normal. Finally, only 1 from 6 lungs treated with EVLP alone was qualified as transplantable, while 5 out of 6 lungs treated with EVLP and NucleoCapture apheresis were qualified as transplantable by certified transplant surgeon.

Thus, NucleoCapture apheresis substantially improve organ transplantability when combined with EVLP procedure.

Example 31: Liver Perfusion with Plasma-Filter Type Hollow-Fiber Affinity Cartridge The effect of plasma-filter type hollow-fiber affinity cartridge manufactured as specified in Example 25 on the outcome of liver normothermic machine perfusion (NMP) with the OrganOx Metra® device was analyzed. A porcine DCD liver model was employed, (WIT=<30 mins, CIT 4-5 hours). After procurement, flushing and static cold storage in UW®solution for transport, livers were prepared on the back bench and fully cannulated. N=3 livers were perfused on the OrganOx Metra® device, with the perfusate composed of autologous leukodepleted blood cell fraction mixed with crystalloid solution, hematocrit 40%, for 12 hours. Following a period of preservation, livers underwent allogenic whole blood reperfusion with ABO compatible blood, simulating transplantation for another 12 hours. We employed the plasma-filter type hollow-fiber affinity cartridge directly integrated into the OrganOx Metra® circuit. The primary endpoint for evaluation was the level of arterial lactate. Lactate has been widely accepted as a critical marker to assess liver viability during NMP (see, e.g., Nostedt et al., PLoS ONE, 2019, 14(8):e0220786). Lactate in the perfusate is used to evaluate the severity of hypoxia-induced hepatocyte dysfunction. The data on lactate quantification over NMP and reperfusion phases are presented in Table 15, below.

TABLE 15

| | Lactate in the perfusate; mmol/L | | | | | | | |
|---|---|---|---|---|---|---|---|---|
| | NMP Perfusion | | | | Reperfusion | | | |
| | 4 h | 6 h | 10 h | 12 h | 4 h | 6 h | 9 h | 12 h |
| Liver 1 | — | 1.2 | — | 0.8 | — | 0.5 | 0.5 | 0.5 |
| Liver 2 | 0.7 | 0.6 | 0.8 | 1.1 | 1.1 | 0.8 | 0.8 | 0.9 |
| Liver 3* | 10.4 | 10.7 | 7.1 | 5.3 | 3.9 | 4.3 | 3.2 | 2.7 |

*DCD liver used in experiment was twice the size of livers 1 and 2 (2.3 kg vs 1.3 kg) and was substantially more injured at the starting point.

Thus, the use of a hollow-fiber type plasma filter with DNA binding matrix placed outside the hollow fibres in the extraluminal space provides surprisingly strong protection of the liver, as evidenced by very low lactate levels during the initial NMP stage and almost complete prevention of the liver from reperfusion injury, which constitutes the main source of morbidity and mortality after orthotopic liver transplantation (OLT). Importantly, such a device is integrated directly into the blood circuit of the OrganOx Metra®

Example 32: Removal of Cell Free DNA from Lung Tissue with NucleoCapture Apheresis During EVLP Tissue samples from porcine lungs treated with NucleoCapture apheresis during ex vivo lung perfusion (EVLP) as described in Example 30 were analyzed as follows: baseline lung biopsies were taken from the right lobe before gastric juice administration through a thoracotomy. Biopsies were also taken just before lung harvest after confirmed ARDS. When the lung was connected to EVLP, biopsies were taken at the end of EVLP procedure. Biopsies were fixed in 10% neutral buffered formalin solution (Sigma Aldrich, Germany) at 4° C. overnight and embedded in paraffin. 4 µm sections were cut and after de-paraffinization, the sections were stained as specified in FIG. 23.

Figure 23A:
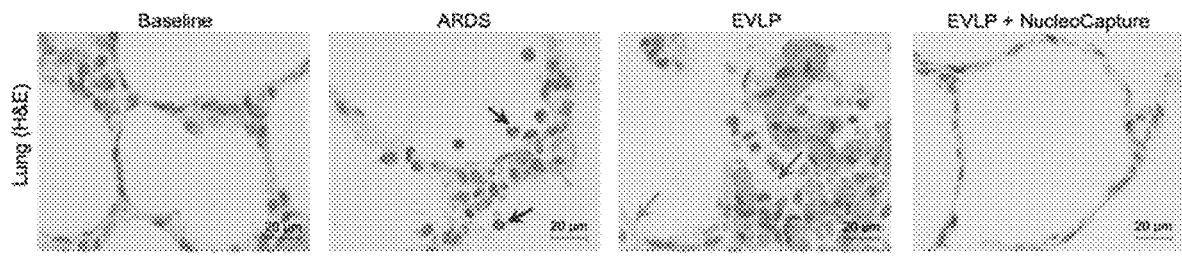
Figure 23B:
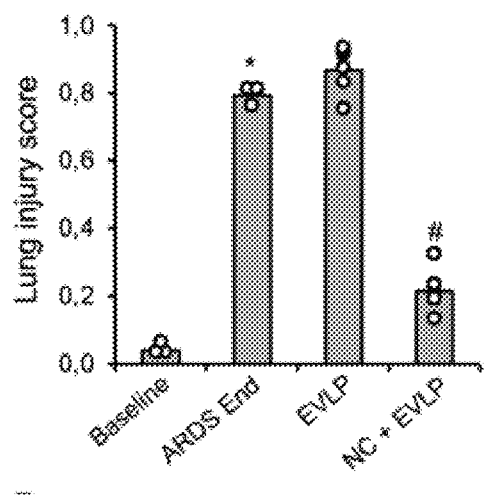

FIG. 23A shows typical images of lung sections stained with haematoxylin and eosin (H&E). Arrows indicate alveolar neutrophils, interstitial neutrophils, hyaline membrane, proteinaceous debris, light septal thickening NETs. Mean±SE lung injury score is represented in FIG. 23B for the different groups. Independent T-test, *P<0.001 compared with baseline, #P<0.01 compared with EVLP alone. It is evident that removal of cfDNA from the EVLP circuit almost entirely cures ARDS driven lung tissue damage.

A consistent finding in ARDS is the deposition of fibrin in the air spaces and lung parenchyma (see, e.g., Whyte et al., J Thromb Haemost, 2020, 18(7):1548-1555).

Figure 23C:
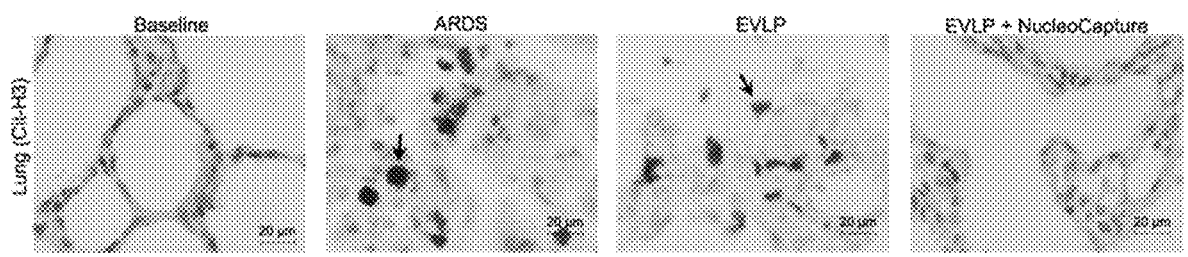
Figure 23D:
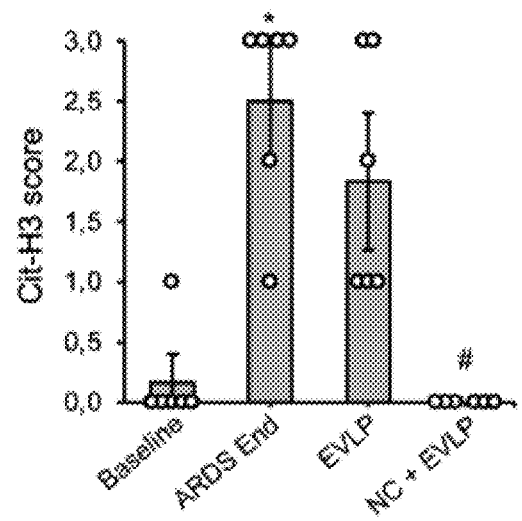
Figure 23E:
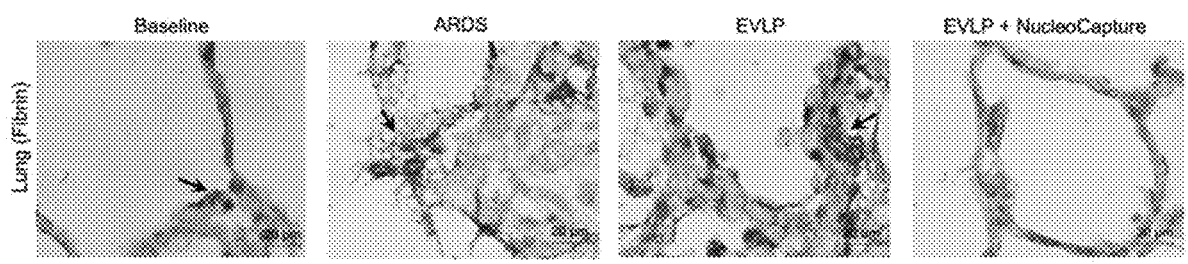
Figure 23F:
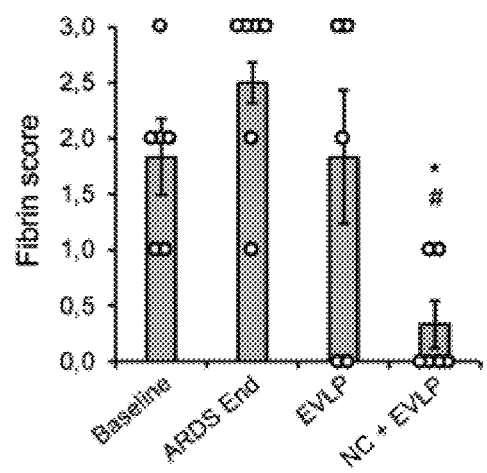

FIG. 23E shows typical lung section images with anti-fibrin immunohistochemistry stain. Black arrows indicate fibrin deposition. Mean±SE Fibrin deposition score is represented in FIG. 23F. Independent t-test, *P<0.01 compared with baseline, #P<0.001 compared with ARDS. It is evident that removal of cfDNA from EVLP circuit almost entirely prevents fibrin deposition in lung tissue.

Citrullinated histone H3 (Cit-H3) is the specific marker for Neutrophil Extracellular Traps (NETs) (see, e.g., Mauracher et al., J Thromb Haemost, 2018, 16(3):508-518). FIG. 23C shows typical lung section images with anti-citrullinated histone H3 (Cit-H3) for NETs. Black arrows indicate NETs. Mean±SE NET formation score is represented in FIG. 23D. Independent t-test, *P<0.001 compared with baseline, #P<0.001 compared with EVLP alone.

It is evident that significant quantities of cfDNA in the form of NETs are deposited in perialveolar tissue in lungs from animals with developed ARDS. Highly unexpectedly, the data herein show that removal of cfDNA (NETs) from perfusate using the NucleoCapture apheresis device of the present invention leads to almost complete disappearance of cfDNA deposits from tissue. As demonstrated herein, selective removal of high molecular weight biologic byproducts from circulation leads to the complete disappearance of pathological tissue deposits of the same byproduct.

Thus, removal of one or more cfDNA types selected from nucleosome-bound cfDNA, exosome-bound cfDNA, and unbound cfDNA from an organ perfusion solution, wherein said organ is perfused extracorporeally using the apheresis device of the present disclosure can provide extraordinary benefit for donor organ health.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate and are provided for description.

Patents, patent applications, publications, product descriptions, and protocols are cited throughout this application, the disclosures of which are incorporated herein by reference in their entireties for all purposes.

---

List of Sequences

```
SEQ ID NO: 1 Human histone H1.3
MMSETAPLAPTIPAPAEKTPVKKKAKKAGATAGKRKASGPPVSELITKAVAASKERSGV
SLAALKKALAAAGYDVEKNNSRIKLGLKSLVSKGTLVQTKGTGASGSFKLNKKAASGE
GKPKAKKAGAAKPRKPAGAAKKPKKVAGAATPKKSIKKTPKKVKKPATAAGTKKVAK
SAKKVKTPQPKKAAKSPAKAKAPKPKAAKPKSGKPKVTKAKKAAPKKK SEQ ID NO: 2 Human histone H1.0
TENSTSAPAAKPKRAKASKKSTDHPKYSDMIVAAIQAEKNRAGSSRQSIQKYIKSHYKV
GENADSQIKLSIKRLVTTGVLKQTKGVGASGSFRLAKSDEPKKSVAFKKTKKEIKKVAT
PKKASKPKKAASKAPTKKPKATPVKKAKKKLAATPKKAKKPKTVKAKPVKASKPKKA
KPVKPKAKSSAKRAGKKK SEQ ID NO: 3 Histone H5 of Anser anser (Western greylag goose), UniProt P02258
TDSPIPAPAPAAKPKRARAPRKPASHPTYSEMIAAAIRADKSRGGSSRQSIQKYVKSHYK
VGQHADLQIKLAIRRLLTTGVLKQTKGVGASGSFRLAKGDKAKRSPAGRKKKKAARK
STSPKKAARPRKARSPAKKPKAAARKARKKSRASPKKAKKPKTVKAKSLKTSKPKKAR
RSKPRAKSGARKSPKKK SEQ ID NO: 4 Histone H5 of Gallus callus UniProt P02259
MTESLVLSPAPAKPKRVKASRRSASHPTYSEMIAAAIRAEKSRGGSSRQSIQKYIKSHYK
VGHNADLQIKLSIRRLLAAGVLKQTKGVGASGSFRLAKSDKAKRSPGKKKKAVRRSTSP
KKAARPRKARSPAKKPKATARKARKKSRASPKKAKKPKTVKAKSRKASKAKKVKRSK
PRAKSGARKSPKKK SEQ ID NO: 5 Human histone H1.0, UniProt P07305
MTENSTSAPAAKPKRAKASKKSTDHPKYSDMIVAAIQAEKNRAGSSRQSIQKYIKSHYK
VGENADSQIKLSIKRLVTTGVLKQTKGVGASGSFRLAKSDEPKKSVAFKKTKKEIKKVA
TPKKASKPKKAASKAPTKKPKATPVKKAKKKLAATPKKAKKPKTVKAKPVKASKPKK
AKPVKPKAKSSAKRAGKKK
```

-continued

List of Sequences

SEQ ID NO: 6 Human histone H1.1, UniProt Q02539
MSETVPPAPAASAAPEKPLAGKKAKKPAKAAAASKKKPAGPSVSELIVQAASSSKERGG
VSLAALKKALAAAGYDVEKNNSRIKLGIKSLVSKGTLVQTKGTGASGSFKLNKKASSVE
TKPGASKVATKTKATGASKKLKKATGASKKSVKTPKKAKKPAATRKSSKNPKKPKTV
KPKKVAKSPAKAKAVKPKAAKARVTKPKTAKPKKAAPKKK SEQ ID NO: 7 Human histone H1.2, UniProt P16403
MSETAPAAPAAAPPAEKAPVKKKAAKKAGGTPRKASGPPVSELITKAVAASKERSGVSL
AALKKALAAAGYDVEKNNSRIKLGLKSLVSKGTLVQTKGTGASGSFKLNKKAASGEAK
PKVKKAGGTKPKKPVGAAKKPKKAAGGATPKKSAKKTPKKAKKPAAATVTKKVAKSP
KKAKVAKPKKAAKSAAKAVKPKAAKPKVVKPKKAAPKKK SEQ ID NO: 8 Human histone H1.4, UniProt P10412
MSETAPAAPAAPAPAEKTPVKKKARKSAGAAKRKASGPPVSELITKAVAASKERSGVSL
AALKKALAAAGYDVEKNNSRIKLGLKSLVSKGTLVQTKGTGASGSFKLNKKAASGEAK
PKAKKAGAAKAKKPAGAAKKPKKATGAATPKKSAKKTPKKAKKPAAAAGAKKAKSP
KKAKAAKPKKAPKSPAKAKAVKPKAAKPKTAKPKAAKPKKAAAKKK SEO ID NO: 9 Human histone H1.5, UniProt Q14529
MSETAPAETATPAPVEKSPAKKKATKKAAGAGAAKRKATGPPVSELITKAVAASKERN
GLSLAALKKALAAGGYDVEKNNSRIKLGLKSLVSKGTLVQTKGTGASGSFKLNKKAAS
GEAKPKAKKAGAAKAKKPAGATPKKAKKAAGAKKAVKKTPKKAKKPAAAGVKKVA
KSPKKAKAAAKPKKATKSPAKPKAVKPKAAKPKAAKPKAAKPKAAKAKKAAAKKK SEP ID NO: 10 Human histone H1.7 (Hit), UniProt P22492
MSETVPAASASAGVAAMEKLPTKKRGRKPAGLISASRKVPNLSVSKLITEALSVSQERV
GMSLVALKKALAAAGYDVEKNNSRIKLSLKSLVNKGILVQTRGTGASGSFKLVIPK
STRSKAKKSVSAKTKKLVLSRDSKSPKTAKTNKRAKKPRATTPKTVRSGRKAKGAKGK
QQQKSPVKARASKSKLTQHHEVNVRKATSKK SEP ID NO: 11 Human recombinant H1.0 histone
TENSTSAPAAKPKRAKASKKSTDHPKYSDMIVAAIQAEKNRAGSSRQSIQKYIKSHYKV
GENADSQIKLSIKRLVTTGVLKQTKGVGASGSFRLAKSDEPKKSVAFKKTKKEIKKVAT
PKKASKPKKAASKAPTKKPKATPVKKAKKKLAATPKKAKKPKTVKAKPVKASKPKKA
KPVKPKAKSSAKRAGKKK SEP ID NO: 12 Recombinant histone HEX of *Caenorhabditis elegans*
MSETVPAASASAGVAAMEKLPTKKRGRKPAGLISASRKVPNLSVSKLITEALSVSQERV
GMSLVALKKALAAAGYDVEKNNSRIKLSLKSLVNKGILVQTRGTGASGSFKLSKKVIPK
STRSKAKKSVSAKTKKLVLSRDSKSPKTAKTNKRAKKPRATTPKTVRSGRKAKGAKGK
QQQKSPVKARASKSKLTQHHEVNVRKATSKK SEQ ID NO: 13 Recombinant human histone H1.4 (HIST1H1E)
SETAPAAPAAPAPAEKTPVKKKARKSAGAAKRKASGPPVSELITKAVAASKERSGVSLA
ALKKALAAAGYDVEKNNSRIKLGLKSLVSKGTLVQTKGTGASGSFKLNKKAASGEAKP
KAKKAGAAKAKKPAGAAKKPKKATGAATPKKSAKKTPKKAKKPAAAAGAKKAKSPK
KAKAAKPKKAPKSPAKAKAVKPKAAKPKTAKPKAAKPKKAAAKKK

SEP ID NO: 14 5'-TCCTACGGGAGGCAGCAGT-3'

SEP ID NO: 15 5'-GGACTACCAGGGTATCTAATCCTGTT-3'

SEP ID NO: 16 (6-FAM)-5'-CGTATTACCGCGGCTGCTGGCAC-3'-(TAMRA)

The invention claimed is:

1. A method of reducing the level of cell-free DNA (cfDNA) in a perfused organ, the method comprising:
   (a) performing an apheresis procedure comprising the diversion of a perfusion solution from the perfused organ into a device to produce the perfusion solution with reduced levels of the cfDNA; and
   (b) returning the perfusion solution with reduced levels of cfDNA into the perfused organ, wherein the apheresis procedure reduces the level of one or more cfDNA selected from nucleosome-bound cfDNA, exosome-bound cfDNA, and unbound cfDNA in the perfusion solution,
   wherein the perfusion solution comprises a cell free artificial perfusion solution or a mixture of an artificial perfusion solution and erythrocytes, and
   wherein the device is configured to perform apheresis of an organ perfusion solution comprising one or more affinity matrices, wherein said one or more affinity matrices are capable of capturing one or more cfDNA selected from nucleosome-bound cfDNA, exosome-bound cfDNA, and unbound cfDNA from the organ perfusion solution, wherein said organ is perfused extracorporeally or in an anatomical cavity, and wherein at least one of said one or more affinity matrices comprises a DNA binding polymer, a DNA binding protein, an anti-histone antibody, an anti-nucleosome antibody, a DNA intercalating agent, an anti-DNA antibody, a lectin, or any combination thereof.

2. A method of reducing an unfavorable transplantation outcome induced by ischemia-reperfusion injury in a subject upon placement of a perfused organ transplant into said subject, the method comprising the following steps performed prior to placing the organ into the subject:
   (a) performing an apheresis procedure comprising the diversion of a perfusion solution from the perfused organ into a device to produce the perfusion solution with reduced levels of the cell-free DNA (cfDNA); and
   (b) returning the perfusion solution with reduced levels of cfDNA into the perfused organ, wherein the apheresis procedure reduces the level of one or more cfDNA selected from nucleosome-bound cfDNA, exosome-bound cfDNA, and unbound cfDNA in the perfusion solution,
   wherein the perfusion solution comprises a cell free artificial perfusion solution or a mixture of an artificial perfusion solution and erythrocytes, and
   wherein the device is configured to perform apheresis of an organ perfusion solution comprising one or more affinity matrices, wherein said one or more affinity matrices are capable of capturing one or more cfDNA selected from nucleosome-bound cfDNA, exosome-bound cfDNA, and unbound cfDNA from the organ perfusion solution, wherein said organ is perfused extracorporeally or in an anatomical cavity, and wherein at least one of said one or more affinity matrices comprises a DNA binding polymer, a DNA binding protein, an anti-histone antibody, an anti-nucleosome antibody, a DNA intercalating agent, an anti-DNA antibody, a lectin, or any combination thereof.

3. The method of claim 1, wherein the unbound cfDNA comprises double stranded DNA (dsDNA), single stranded DNA (ssDNA) and oligonucleotides.

4. The method of claim 1, wherein the perfused organ is selected from liver, lung, kidney, pancreas, and heart.

5. The method of claim 1, wherein the perfusion solution comprises a mixture of an artificial perfusion solution and erythrocytes.

6. The method of claim 1, wherein the perfusion solution comprises a cell free artificial perfusion solution.

7. The method of claim 2, wherein the unbound cfDNA comprises double stranded DNA (dsDNA), single stranded DNA (ssDNA) and oligonucleotides.

8. The method of claim 2, wherein the perfused organ is selected from liver, lung, kidney, pancreas, and heart.

9. The method of claim 2, wherein the perfusion solution comprises a mixture of an artificial perfusion solution and erythrocytes.

10. The method of claim 2, wherein the perfusion solution comprises a cell free artificial perfusion solution.

11. The method of claim 1, wherein at least one of said one or more affinity matrices comprises a DNA binding protein.

12. The method of claim 11, wherein the DNA binding protein is a histone.

13. The method of claim 12, wherein the histone is a linker histone.

14. The method of claim 13, wherein the linker histone is selected from an H1.0 linker histone, an H1.1 linker histone, an H1.2 linker histone, an H1.3 linker histone, an H1.4 linker histone, an H1.5 linker histone, and H1.7 linker histone.

15. The method of claim 13, wherein the linker histone comprises an amino acid sequence which is at least 70% identical to the sequence selected from:

```
                                           (SEQ ID NO: 1)
MMSETAPLAPTIPAPAEKTPVKKKAKKAGATAGKRKASGPPVSELITK

AVAASKERSGVSLAALKKALAAAGYDVEKNNSRIKLGLKSLVSKGTLV

QTKGTGASGSFKLNKKAASGEGKPKAKKAGAAKPRKPAGAAKKPKKVA

GAATPKKSIKKTPKKVKKPATAAGTKKVAKSAKKVKTPQPKKAAKSPA

KAKAPKPKAAKPKSGKPKVTKAKKAAPKKK;

(SEQ ID NO: 2)
TENSTSAPAAKPKRAKASKKSTDHPKYSDMIVAAIQAEKNRAGSSRQS

IQKYIKSHYKVGENADSQIKLSIKRLVTTGVLKQTKGVGASGSFRLAK

SDEPKKSVAFKKTKKEIKKVATPKKASKPKKAASKAPTKKPKATPVKK

AKKKLAATPKKAKKPKTVKAKPVKASKPKKAKPVKPKAKSSAKRAGKK

K;

(SEQ ID NO: 3)
TDSPIPAPAPAAKPKRARAPRKPASHPTYSEMIAAAIRADKSRGGSSR

QSIQKYVKSHYKVGQHADLQIKLAIRRLLTTGVLKQTKGVGASGSFRL

AKGDKAKRSPAGRKKKKAARKSTSPKKAARPRKARSPAKKPKAAARK

ARKKSRASPKKAKKPKTVKAKSLKTSKPKKARRSKPRAKSGARKSPKK

K;
and (SEQ ID NO: 4)
MTESLVLSPAPAKPKRVKASRRSASHPTYSEMIAAAIRAEKSRGGSSR

QSIQKYIKSHYKVGHNADLQIKLSIRRLLAAGVLKQTKGVGASGSFRL

AKSDKAKRSPGKKKKAVRRSTSPKKAARPRKARSPAKKPKATARKARK

KSRASPKKAKKPKTVKAKSRKASKAKKVKRSKPRAKSGARKSPKKK.
```

16. The method of claim 1, wherein the device comprises two or more different affinity matrices arranged within one device.

17. The method of claim 2, wherein at least one of said one or more affinity matrices comprises a DNA binding protein.

18. The method of claim 17, wherein the DNA binding protein is a histone.

19. The method of claim 18, wherein the histone is a linker histone.

20. The method of claim 19, wherein the linker histone is selected from an H1.0 linker histone, an H1.1 linker histone, an H1.2 linker histone, an H1.3 linker histone, an H1.4 linker histone, an H1.5 linker histone, and H1.7 linker histone.

21. The method of claim 19, wherein the linker histone comprises an amino acid sequence which is at least 70% identical to the sequence selected from:

```
                                           (SEQ ID NO: 1)
MMSETAPLAPTIPAPAEKTPVKKKAKKAGATAGKRKASGPPVSELITK

AVAASKERSGVSLAALKKALAAAGYDVEKNNSRIKLGLKSLVSKGTLV

QTKGTGASGSFKLNKKAASGEGKPKAKKAGAAKPRKPAGAAKKPKKVA

GAATPKKSIKKTPKKVKKPATAAGTKKVAKSAKKVKTPQPKKAAKSPA

KAKAPKPKAAKPKSGKPKVTKAKKAAPKKK;

(SEQ ID NO: 2)
TENSTSAPAAKPKRAKASKKSTDHPKYSDMIVAAIQAEKNRAGSSRQS

IQKYIKSHYKVGENADSQIKLSIKRLVTTGVLKQTKGVGASGSFRLAK

SDEPKKSVAFKKTKKEIKKVATPKKASKPKKAASKAPTKKPKATPVKK

AKKKLAATPKKAKKPKTVKAKPVKASKPKKAKPVKPKAKSSAKRAGKK

K;

(SEQ ID NO: 3)
TDSPIPAPAPAAKPKRARAPRKPASHPTYSEMIAAAIRADKSRGGSSR

QSIQKYVKSHYKVGQHADLQIKLAIRRLLTTGVLKQTKGVGASGSFRL

AKGDKAKRSPAGRKKKKAARKSTSPKKAARPRKARSPAKKPKAAARK

ARKKSRASPKKAKKPKTVKAKSLKTSKPKKARRSKPRAKSGARKSPKK

K;
and (SEQ ID NO: 4)
MTESLVLSPAPAKPKRVKASRRSASHPTYSEMIAAAIRAEKSRGGSSR

QSIQKYIKSHYKVGHNADLQIKLSIRRLLAAGVLKQTKGVGASGSFRL

AKSDKAKRSPGKKKKAVRRSTSPKKAARPRKARSPAKKPKATARKARK

KSRASPKKAKKPKTVKAKSRKASKAKKVKRSKPRAKSGARKSPKKK.
```

22. The method of claim 2, wherein the device comprises two or more different affinity matrices arranged within one device.

* * * * *